US011851415B2

(12) United States Patent
Tegen et al.

(10) Patent No.: US 11,851,415 B2
(45) Date of Patent: Dec. 26, 2023

(54) CONTINUOUS ISOLATION OF CANNABIDIOL AND CANNABINOIDS AND CONVERSION OF CANNABIDIOL TO DELTA 8-TETRAHYDROCANNABINOL AND DELTA 9-TETRAHYDROCANNABINOL

(71) Applicant: Cleen Technology Inc., Tukwila, WA (US)

(72) Inventors: Mark G. Tegen, Seattle, WA (US); Joon Cho, Wilsonville, OR (US)

(73) Assignee: Cleen Technology Inc., Tukwila, WA (US)

( * ) Notice: Subject to any disclaimer, the term of this patent is extended or adjusted under 35 U.S.C. 154(b) by 142 days.

(21) Appl. No.: 16/840,247

(22) Filed: Apr. 3, 2020

(65) Prior Publication Data

US 2020/0255389 A1 Aug. 13, 2020

Related U.S. Application Data

(60) Continuation-in-part of application No. 16/672,047, filed on Nov. 1, 2019, which is a division of application No. 16/388,182, filed on Apr. 18, 2019, now Pat. No. 11,192,870, which is a continuation of application No. PCT/US2019/021138, filed on Mar. 7, 2019.

(60) Provisional application No. 62/715,545, filed on Aug. 7, 2018, provisional application No. 62/697,920, filed on Jul. 13, 2018, provisional application No. 62/697,923, filed on Jul. 13, 2018, provisional application No. 62/697,926, filed on Jul. 13, 2018, provisional application No. 62/639,608, filed on Mar. 7, 2018.

(51) Int. Cl.
*C07D 301/32* (2006.01)
*C07D 311/86* (2006.01)
*C07D 311/80* (2006.01)

(52) U.S. Cl.
CPC .......... *C07D 301/32* (2013.01); *C07D 311/86* (2013.01)

(58) Field of Classification Search
CPC .... C07D 301/32; C07D 311/86; C07D 311/80
See application file for complete search history.

(56) References Cited

U.S. PATENT DOCUMENTS

| | | |
|---|---|---|
| 4,116,979 A | 9/1978 | Razdan et al. |
| 5,342,971 A | 8/1994 | Herlt et al. |
| 6,365,416 B1 | 4/2002 | Elsohly et al. |
| 6,403,126 B1 | 6/2002 | Webster et al. |
| 6,730,519 B2 | 5/2004 | Elsohly et al. |
| 7,399,872 B2 * | 7/2008 | Webster ............... C07D 311/80 549/390 |
| 7,674,922 B2 | 3/2010 | Burdick et al. |
| 8,106,244 B2 | 1/2012 | Burdick et al. |
| 10,189,762 B1 | 1/2019 | Oroskar et al. |
| 11,192,870 B2 | 12/2021 | Tegen et al. |
| 2003/0017216 A1 | 1/2003 | Schmidt et al. |
| 2004/0143126 A1 | 7/2004 | Webster et al. |
| 2005/0266108 A1 | 12/2005 | Flockhart et al. |
| 2010/0298579 A1 * | 11/2010 | Steup .................. A61P 43/00 568/329 |
| 2016/0184261 A1 | 6/2016 | Gutman et al. |
| 2017/0333503 A1 | 11/2017 | Ayres |
| 2018/0036278 A1 | 2/2018 | Rutz |

FOREIGN PATENT DOCUMENTS

| | | | |
|---|---|---|---|
| CN | 102151259 A | 8/2011 | |
| CN | 1997636 B | 9/2011 | |
| CN | 106831353 A | 6/2017 | |
| CN | 107011125 A | 8/2017 | |
| DE | 102005028937.1 B4 | 7/2009 | |
| WO | 20160135346 A1 | 9/2016 | |
| WO | 2017194173 A1 | 11/2017 | |
| WO | WO-2017194173 A1 * | 11/2017 | ........... B01D 15/185 |
| WO | 20170214529 A1 | 12/2017 | |

OTHER PUBLICATIONS

Cox, G., "Chromatography, Preparative." Kirk-Othmer Encyclopedia of Chemical Technology (2000): 1-30.*
Gaoni, Y.,"Isolation and structure of. Delta.+-tetrahydrocannabinol and other neutral cannabinoids from hashish." Journal of the American Chemical Society 93.1 (1971): 217-224.*
Hanuš, L. O., "Phytocannabinoids: a unified critical inventory." Natural product reports 33.12 (2016): 1357-1392.*
Patel, B., "Qualitative and quantitative measurement of cannabinoids in cannabis using modified HPLC/DAD method." Journal of Pharmaceutical and Biomedical Analysis 146 (2017): 15-23.*
Petcoff, D.G., "Marihuana: identification of cannabinoids by centrifugal chromatography." Science 173.3999 (1971): 824-826.*

(Continued)

*Primary Examiner* — John M Mauro
(74) *Attorney, Agent, or Firm* — Dorsey & Whitney LLP

(57) ABSTRACT

In alternative embodiments, provided are processes for obtaining or purifying a substantially pure $\Delta^8$tetrahydrocannabinol ($\Delta^8$THC) and/or $\Delta^9$tetrahydrocannabinol ($\Delta^9$THC) and optionally a plurality of cannabinoids or terpenes from a natural or a synthetic source, wherein the natural or the synthetic source comprises a cannabidiol (CBD) and optionally a plurality of cannabinoids or terpenes. Also provided are processes comprising the continuous isolation and purification of cannabinoids or terpenes, and further isomerization of the purified cannabidiol to $\Delta^8$tetrahydrocannabinol ($\Delta^8$THC) and $\Delta^9$tetrahydrocannabinol ($\Delta^9$THC). In alternative embodiments, provided are processes for converting $\Delta 8$-THC into $\Delta^9$-THC. In alternative embodiments, provided are processes for the industrial scale continuous isolation and purification of cannabinoids and further isomerization of the purified cannabidiol to $\Delta^9$-THC.

17 Claims, 2 Drawing Sheets

(56) References Cited

OTHER PUBLICATIONS

Shah, V. J., Synthesis of cannabidiol stereoisomers and analogs as potential anticonvulsant agents. The University of Arizona, 1988.*

Taylor, E. C., "Active constituents of hashish. Synthesis of dl-Δ6-3,4-trans-tetrahydrocannabinol." Journal of the American Chemical Society 88.2 (1966): 367-369.*

Extended European Search Report (EESR) for EP19764235.8, dated Jan. 14, 2022.

ISR/WO dated May 13, 2019 for PCT Application No. PCT/US2019/021138.

Abrams, Donald, "Cannabis in Pain and Palliative Care", The Pain Practitioner, vol. 20, No. 4, Winter 2010, 5 pages.

Gaoni, Y., et al., "Hashish—VII: The Isomerization of Cannabidiol to Tetrahydrocannabinols", Tetrahedron, vol. 22, Oct. 1965, 8 pages.

Kong, et al., "An Automatic System For Multidimensional Integrated Protein Chromatography", Journal of Chromatography A, 1217, Sep. 2010, 6898-6904.

McGrew, et al., "Kinetic Versus Thermodynamic Control: An organic chemistry experiment", Journal of Chemical Education, vol. 48, No. 6, Jun. 1971.

Poole, C.F., "Chromatography, Liquid", Kirk-Othmer Encyclopedia of Chemical Technology, 2013, 39 pages.

Razdan, Raj K., "Structure-Activity Relationships In Cannabinoids", Pharmacological Reviews, vol. 38, No. 2, Aug. 1986, 75 pages.

Wang, et al., "Quantitative Determination of Δ9-THC, CBG, CBD, Their Acid Pre-Cursors and Five Other Neutral Cannabinoids By UHPLC-UV-MS", Planta Medica, Mar. 2018.

* cited by examiner

CONTINUOUS ISOLATION OF CANNABIDIOL AND CANNABINOIDS AND CONVERSION OF CANNABIDIOL TO DELTA 8-TETRAHYDROCANNABINOL AND DELTA 9-TETRAHYDROCANNABINOL

RELATED APPLICATIONS

This application is a continuation-in-art (CIP) patent application under 35 U.S.C. § 120, which claims benefit of priority to U.S. Ser. No. 16/672,047, filed Nov. 1, 2019, which is a divisional patent application under 35 U.S.C. § 120, claiming benefit of priority to U.S. patent application Ser. No. 16/388,182, filed Apr. 18, 2019, which continuation of Patent Convention Treaty (PCT) International Application serial number PCT/US2019/021138, filed Mar. 7, 2019, which claims the benefit of priority under 35 U.S.C. § 119(e) of U.S. Provisional Patent Application Ser. No. (USSN) U.S. Ser. No. 62/639,608, filed Mar. 7, 2018; U.S. Ser. No. 62/697,920, filed Jul. 13, 2018; U.S. Ser. No. 62/697,926, filed Jul. 13, 2018; U.S. Ser. No. 62/697,923, filed Jul. 13, 2018; and U.S. Ser. No. 62/715,545, filed Aug. 7, 2018. The aforementioned applications are expressly incorporated herein by reference in its entirety and for all purposes.

FIELD OF THE INVENTION

This invention generally relates to the industrial scale processing and purification of cannabinoids. In alternative embodiments, provided are processes for obtaining or purifying a substantially pure $\Delta^8$tetrahydrocannabinol ($\Delta^8$THC) and/or $\Delta^9$tetrahydrocannabinol ($\Delta^9$THC) and optionally a plurality of cannabinoids or terpenes from a natural or a synthetic source, wherein the natural or the synthetic source comprises a cannabidiol (CBD) and optionally a plurality of cannabinoids or terpenes. Also provided are processes comprising the continuous isolation and purification of cannabinoids and further isomerization of the purified cannabidiol to $\Delta^8$-tetrahydrocannabinol ($\Delta^8$-THC) and $\Delta^9$-tetrahydrocannabinol ($\Delta^9$-THC). In alternative embodiments, provided are processes for converting $\Delta^8$-THC into $\Delta^9$-THC. In alternative embodiments, provided are processes for the industrial scale continuous isolation and purification of cannabinoids and further isomerization of the purified cannabidiol to $\Delta^9$-THC.

BACKGROUND

Cannabinoids are a class of diverse chemical compounds that acts on cannabinoid receptors in cells that alter neurotransmitter release in the brain. They are of great value in pharmaceutical applications. Ligands for these receptor proteins include the endocannabinoids (produced naturally in the body by animals) and the phytocannabinoids (found in hemp, *Cannabis* and some other plants). Among these cannanbinoids is cannabidiol (CBD) widely considered to have a range of potential medical applications including treatment of Dravet syndrome, a rare form of epilepsy that is difficult to treat that begins in infancy. Another cannabinoid is $\Delta^9$tetrahydrocannabinol ($\Delta^9$THC) that acts as an appetite stimulant for people with AIDS and antiemetic for people receiving chemotherapy.

Tetrahydrocannabinol (THC) is the principal psychoactive constituent of cannabis. Natural phytocannabinoids sources such as hemp and *Cannabis* contain at least 113 different cannabinoids. Currently mixtures comprising terpenes, lipids, waxes, chlorophyll and other plant matter, including cannabinoids, are extracted in mass using polar solvent extraction, nonpolar solvent extraction or mixtures thereof and then physically separated using multiple steps including distillation, chromatography, winterization or combinations of these processes.

Recently, public interest in *Cannabis* as medicine has been growing, based in no small part on the fact that *Cannabis* has long been considered to have medicinal properties, ranging from treatment of cramps, migraines, convulsions, appetite stimulation and attenuation of nausea and vomiting. In fact, a report issued by the National Academy of Sciences' Institute of Medicine indicated that the active components of *Cannabis* appear to be useful in treating pain, nausea, AIDS-related weight loss or "wasting", muscle spasms in multiple sclerosis as well as other problems. Advocates of medical marijuana argue that *Cannabis* is also useful for glaucoma, Parkinson's disease, Huntington's disease, migraines, epilepsy and Alzheimer's disease.

Marijuana refers to varieties of *Cannabis* having a high content of $\Delta^9$-tetrahydrocannabinol ($\Delta^9$-THC), which is the psychoactive ingredient of marijuana, whereas industrial hemp refers to varieties of the *Cannabis* plant that have a low content of $\Delta^9$-THC.

Furthermore, $\Delta^9$-THC is only one of a family of about 60 bi- and tri-cyclic compounds named cannabinoids. For example, $\Delta^8$-THC is a double bond isomer of $\Delta^9$-THC and is a minor constituent of most varieties of *Cannabis* (see, e.g., Hollister and Gillespie, 1972, Clin Pharmacol Ther 14: 353). The major chemical difference between the two compounds is that $\Delta^9$-THC can be oxidized to cannabinol whereas $\Delta^8$-THC does not and is in fact very stable. $\Delta^8$-THC, for the most part, produces similar psychometric effects as does $\Delta^9$-THC, but is generally considered to be 50% less potent than $\Delta^9$-THC and has been shown in some cases to be 3-10 times less potent. $\Delta^8$-THC has also been shown to be more (200%) effective an anti-emetic than $\Delta^9$-THC and has been used as an anti-emetic in children, based on the belief that the side effects of $\Delta^9$-THC and $\Delta^8$-THC, such as anxiety and dysphoria, are more prevalent in adults than children (Abrahamov et al, 1995, Life Sciences 56: 2097-2102). On the other hand, CBD has no activity on its own when administered to humans. It is of note that CBD is typically about 2% (0.54%) dry weight of hemp chaff, $\Delta^8$-THC is approximately 0.2% (0.05-0.5%) dry weight and $\Delta^9$-THC is approximately 0.1% (0.05-0.3%).

The large variety of cannabinoids and other plant matter present in extracts makes it difficult to separate the cannabinoids from each other as well as from the non-cannabinoid plant matter and achieve a high enough purity level to meet pharmaceutical or analytical requirements. Separations can be achieved using various techniques including such as distillation which subjects the cannabinoid rich mixture of heat history which can degrade the cannabinoids. For separations that do not subject the cannabinoids to heat history chromatography is applied however the current state of the art is to apply these techniques in a non-continuous method which severely limits the scale and efficiency of the separation methodology.

There remains a need for a method that is simple, efficient and continuous process to first generate purified cannabidiol and combined with a simple, efficient method to convert cannabidiol into a mixture of $\Delta^8$THC and $\Delta^9$-THC. Clearly, as the cannabinoids are of potential medicinal value, improved methods of both isolating CBD and converting CBD to $\Delta^8$-THC and $\Delta^9$-THC are needed.

SUMMARY

Chapt. I

In alternative embodiments, provided are processes and methods for purifying cannabinoids and converting cannabidiol to $\Delta^8$-tetrahydrocannabinol ($\Delta^8$THC) and $\Delta^9$-tetrahydrocannabinol ($\Delta^9$THC). In alternative embodiments, provided are processes for converting $\Delta$8-THC to $\Delta^9$-THC.

In alternative embodiments, provided are processes and methods for obtaining or purifying a substantially pure $\Delta^9$ THC from a natural or a synthetic source, wherein optionally the natural source comprises a plant or a microbial material, or a material derived from a plant source, comprising:

(a) obtaining or being provided a first extract, aliquot or sample of the natural or synthetic source comprising a cannabidiol (CBD) and/or $\Delta^9$ THC and/or $\Delta^8$THC and/or a plurality of cannabinoids or terpenes from the natural or the synthetic source;

(b) dissolving the first extract aliquot or sample in a first solvent, or diluting the first extract aliquot or sample in a first solvent;

(c) loading the solvent-dissolved or diluted first extract aliquot or sample onto a first chromatography column, wherein optionally the chromatography column is a normal phase chromatography column, an ion exchange chromatography column, or a reverse phase chromatography column, wherein the $\Delta^9$ THC and/or $\Delta^8$THC and/or plurality of cannabinoids or terpenes are reversibly bound to the first chromatography column, wherein optionally some of or substantially most of the extract aliquot or sample material not reversibly bound to the first column at the first station is removed with a first wash solution before the column is moved to a next or a second station;

(d) eluting the $\Delta^9$ THC and/or $\Delta^8$THC and/or plurality of cannabinoids or terpenes off the first chromatography column with an elution solvent mixture, wherein optionally the eluting is a gradient elution;

(e) collecting or isolating the $\Delta^9$ THC and/or $\Delta^8$THC and/or plurality of cannabinoids or terpenes from said elution solvent mixture, wherein optionally the elution is by a gradient elution process and the $\Delta^9$ THC and/or $\Delta^8$THC and/or plurality of cannabinoids or terpenes are separately collected in different or separate gradient elution fractions, wherein optionally, if the elution is by a gradient elution process using normal phase column chromatography: in a first gradient polar compounds and some or substantially most of the cannabinol (CBN), cannabigerol (CBG), cannabichromene (CBC) are eluted off the column; in a second gradient solvent remaining cannabidiol (CBD) is eluted off the column; in a third gradient a CBD/tetrahydrocannabinol (THC) mix is first eluted and then remaining THC is eluted off the column; in a fourth gradient remaining cannabinoids are eluted off the column, wherein optionally the remaining cannabinoids comprise CBC, CBG, CBN; and, in a fifth gradient solvent all remaining polar compounds are eluted off the column, wherein the remaining polar compounds comprises cannabidiolic acid (CBDA) and tetrahydrocannabinolic acid (THCA), and optionally, if the elution is by a gradient elution process using reverse phase column chromatography, the gradient elution:

begins with an 80:20 or a 70:30 methanol to water elution solution or equivalent, which elutes off the column some or substantially most of the polar compounds, wherein optionally the polar compounds comprise CBDA and/or TGCA;

then the gradient elution moves to an 85:15 or an 80:20 methanol to water elution solvent or equivalent, which elutes off the column some or substantially most of the CBD;

then the gradient elution moves to a 90:10 methanol to water elution solution or equivalent, which initially elutes off the column a mix of the remaining CBD and THC, and finally elutes off the column THC; and finally the gradient elution moves to a 100% methanol elution solution, which removes a mix of remaining cannabinoids comprising CBC, CBG, CBN;

(f) adding a second solvent of opposite polarity (to the elution solvent mixture) to said elution solvent mixture;

(g) removing all or substantially most of the second solvent, thereby leaving a first extract comprising a plurality of cannabinoids or terpenes comprising the $\Delta^9$ THC and/or $\Delta^8$THC and/or plurality of cannabinoids or terpenes, wherein optionally the plurality of cannabinoids comprise CBC, CBG, CBN;

(h) dissolving the first extract comprising the plurality of cannabinoids or terpenes in a first reaction solvent;

(i) adding a catalyst to the first extract comprising the plurality of cannabinoids or terpenes and the first reaction solvent, wherein the catalyst can be added before, simultaneous with or after addition of the first reaction solvent to the extract comprising the plurality of cannabinoids or terpenes; and (j) reacting the first extract comprising the plurality of cannabinoids or terpenes, the catalyst and the first reaction solvent, wherein optionally the reaction converts $\Delta$8-THC to $\Delta^9$-THC;

(k) adding a neutralizing agent;

(l) removing of the catalyst and the neutralizing agent to generate a first reaction product;

(m) optionally adding a second reaction solvent to the first reaction product;

(n) optionally removing all or substantially most of the second reaction solvent, thereby leaving a second extract comprising a plurality of cannabinoids or terpenes;

(o) adding a stabilization agent to the second extract;

(p) adding an elimination agent to the second extract;

(q) removing (or removing of substantially all) of the stabilization agent and the elimination agent, thereby leaving a third extract;

(r) and if the second reaction solvent is not removed in step (n), adding a third solvent of opposite polarity to the third extract;

(s) removing the second reaction solvent, if present (if not removed in step (n)), and removing all or substantially most of the third solvent of opposite polarity, if added, thereby leaving a fourth extract;

(t) dissolving third or the fourth extract in a second solvent, wherein optionally the second solvent is the same or substantially the same as the first solvent;

(u) loading the dissolved third or the fourth extract onto a second chromatography column, wherein optionally the chromatography column is a normal phase chromatography column or a reverse phase chromatography column, wherein the plurality of cannabinoids or terpenes are reversibly bound to the second chromatography column, and optionally the second chromatography column is the same as the first chromatography column;

(v) eluting the dissolved third or the fourth extract from the second column with an elution solution, wherein optionally the elution is by a gradient elution process and the $\Delta^9$ THC and/or $\Delta^8$ THC and/or plurality of cannabinoids or terpenes are separately collected in different or separate gradient elution fractions;

(w) optionally collecting the plurality of cannabinoids or terpenes from the elution solution, and/or removing all or substantially most of the elution solvent, thereby obtaining or purifying a substantially pure plurality of cannabinoids or terpenes, wherein optionally the plurality of cannabinoids comprises $\Delta^9$ THC and/or $\Delta^8$ THC.

In alternative embodiments, the CBD content of the first extract, aliquot or sample material is greater than about 25%, 50%, 75%, 90% or 95% by weight, or is between about 5% and 95% by weight, by weight of the material.

In alternative embodiments, the first solvent and/or the second solvent comprises methanol, propanol, ethanol, isobutanol, butanol, isopropanol, tetrahydrofuran, chloroform, acetone, hexane, methylene dichloride, and/or dichloroethane; and optionally the first solvent and/or the second solvent comprises chloroform, methylene dichloride and methanol, propanol and/or ethanol.

In alternative embodiments, the chromatography column, e.g., a normal phase chromatography column, ion exchange column or reverse phase column, comprises a silica gel, an alumina or an ion exchange material, and optionally the ion exchange column comprises an anion exchange material.

In alternative embodiments, the elution solution comprises or is a solvent, and the solvent comprises a one or a mixture of: ethylene dichloride; chloroform; or methylene dichloride; and alcohol comprising methanol, ethanol, propanol or butanol or a mixture thereof; an acid comprising acetic acid, formic acid, oxalic acid, glycolic acid or a mixture thereof; and/or, ammonium hydroxide. In alternative embodiments, the elution solvent is or comprises a dichloromethane, dichloroethane, or chloroform and methanol or ethanol.

In alternative embodiments, the first reaction solvent comprises ethylene dichloride, chloroform, methylene dichloride, toluene, xylene, benzene, hexane and/or pentane, or mixtures thereof.

In alternative embodiments, the catalyst is or comprises a Lewis acid or a non-oxidizing acid catalyst. In alternative embodiments, the catalyst comprises p-toluenesulfonic acid.

In alternative embodiments, the neutralizing agent is or comprises an alkali. In alternative embodiments, the neutralizing agent is or comprises sodium bicarbonate, sodium carbonate, calcium hydroxide or ammonium hydroxide.

In alternative embodiments, the stabilization agent is or comprises zinc chloride or methylene chloride.

In alternative embodiments, the second reaction solvent comprises dimethyl sulfoxide, water, dimethylformamide, methanol, ethylene dichloride, chloroform, propanol, ethanol, isobutanol, formamide, methylene dichloride, butanol, isopropanol, tetrahydrofuran, dioxane, benzene, toluene and/or xylene or a mixture thereof. In alternative embodiments, the second reaction solvent comprises chloroform, hexane, dichloromethane, dichloroethane, benzene or toluene or a mixture thereof.

In alternative embodiments, the elimination agent is or comprises a strong base; and optionally the strong base comprises: lithium hydroxide (LiOH), sodium hydroxide (NaOH), potassium hydroxide (KOH), rubidium hydroxide (RbOH), cesium hydroxide (CsOH), magnesium hydroxide (Mg(OH)$_2$), calcium hydroxide (Ca(OH)$_2$), strontium hydroxide Sr(OH)$_2$, barium hydroxide Ba(OH)$_2$), potassium hydride and/or sodium hydride, potassium tert-pentoxide, organic superbases, bispidines, multicyclic polyamines, organometallic compounds of reactive metals, wherein optionally the reactive metals comprise organolithium, organo-magnesium, lithium diisopropylamide, n-butyl lithium and potassium tert-butoxide, sodium methoxide, or sodium ethoxide. In alternative embodiments, the elimination agent is or comprises potassium tert-pentoxide, lithium diisopropylamide and/or potassium tert-butoxide.

In alternative embodiments, the elution solvent is or comprises a solvent or mixture of solvents, e.g., as described in the Examples.

In alternative embodiments, the extract is filtered before being loaded on to the column, and optionally the extract is mixed with silica, diatomaceous earth (DE), bentonite clay (BC), or equivalents, or mixtures thereof, before filtering, and optionally the extract is chilled before being mixed with the silica, DE, BC or equivalents or is chilled before being filtered.

In alternative embodiments, the microbial material comprises or is derived from a bacterium, an algal cell, a lichen or a yeast, or a recombinant bacterium, lichen, algal cell or yeast cell.

In alternative embodiments, the plant or starting material comprises or is derived from a botanical drug substance, including hemp or a cannabis plant, wherein optionally the cannabis plant is a *Cannabis sativa*, a *Cannabis* chemovar, or variants thereof, or a decarboxylated *Cannabis* plant material. In alternative embodiments, the plant or starting material comprises oils or extracts from a trichome or a trichome fraction of a pubescent plant, or an algae or a lichen; and optionally the oils or extracts are from the plant or microbial material by: washing, contacting or exposing the trichome or trichome fraction, or the pubescent plant, algae or lichen, with: at least one non-polar, organic solvent; at least one polar, organic solvent; or, a mix of at least one non-polar, organic solvent with (and) at least one polar, organic solvent.

Chapt. II

In alternative embodiments, provided are methods of or processes for purifying a cannabinoid to substantially pure $\Delta^9$tetrahydrocannabinol ($\Delta^9$-THC) from a natural or a synthetic source, wherein optionally the natural source comprises a plant or microbial material, or a material derived from a plant or a microbial source.

In one embodiment, the method comprises:

a. providing or having provided a first extract, aliquot or sample of the natural or synthetic source comprising at least one of cannabidiol (CBD), $\Delta^9$ THC, $\Delta^8$ THC, and plurality of cannabinoids or terpenes from the natural or the synthetic source, optionally a plant material;

b. providing or having provided a continuous chromatography apparatus or device comprising a plurality of stations and a plurality of chromatography columns, wherein optionally the plurality of stations and the plurality of chromatography columns comprise at least 2, 3, 4, 5, 6, 7, or 8 or more, or between about 3 and 30, stations and/or chromatography columns;

c. introducing or loading the first extract, aliquot or sample into a first column at a first station, wherein the CBD, $\Delta^9$ THC, and $\Delta^8$ THC and plurality of cannabinoids or terpenes reversibly bind to the first column, wherein optionally some of or substantially most of the first extract material not reversibly bound to the first column at the first station is removed with a first wash solution before the column is moved to a next or a second station;

d. moving the first column to a second station, wherein after the first column is moved to the second station a next or second column is introduced into the first station;

e. eluting the extract from the first chromatography column with a first elution solvent at the second station, wherein optionally the eluting is a gradient elution;

f. collecting the first elution fractions from the first column at the second station;

g. removing all or substantially most of the first elution solution from the first elution fractions to produce a first purified extract substantially free of CBD, $\Delta^9$ THC, and $\Delta^8$ THC;

h. optionally repeating steps d to g on the first column with at least one additional elution solvent, wherein the at least one additional elution solvent produces a second purified extract substantially free of CBD, $\Delta^9$ THC, and $\Delta^8$ THC;

i. when the first column is moved to the next, or second, station, introducing a next or second column into the first station, and the extract, aliquot or sample is introduced or loading into the next or second column at the first station;

j. moving the second column to the next or second station after the first column is moved to a next or third station;

k. eluting the extract from the first column with a second elution solvent at the next or second station, wherein optionally the elution is by a gradient elution process and the CBD, $\Delta^9$ THC, and $\Delta^8$ THC and plurality of cannabinoids or terpenes are separately collected in different or separate gradient elution fractions wherein optionally, if the elution is by a gradient elution process: in a first gradient solvent non-polar compounds and terpenes are eluted off the column; in a second gradient solvent cannabidiol (CBD) is eluted off the column; in a third gradient solvent a CBD/tetrahydrocannabinol (THC) mix is first eluted and then remaining THC is eluted off the column; in a fourth gradient minor cannabinoids are eluted off the column, wherein optionally the minor cannabinoids comprise CBC, CBG, CBN; and, in a fifth gradient solvent all remaining polar compounds are eluted off the column, wherein the remaining polar compounds comprises cannabidiolic acid (CBDA) and tetrahydrocannabinolic acid (THCA);

l. collecting the second elution fractions from the first chromatography column at the second station;

m. removing all or substantially most of the second elution solvent from the second elution fractions to produce a second purified extract (or a third purified extract if step h is completed) comprising at least about 75% of the CBD, $\Delta^9$ THC, and $\Delta^8$ THC from the first extract, or between about 60% and 90% of CBD, $\Delta^9$ THC, and $\Delta^8$ THC, or between about 50% and 95% of CBD, $\Delta^9$ THC, and $\Delta^8$ THC, and optionally the gradient elution:

begins with an 80:20 or a 70:30 methanol to water elution solution or equivalent, which elutes off the column some or substantially most of the cannabidiolic acid (CBDA) and tetrahydrocannabinolic acid (THCA) and polar terpenes;

then the gradient elution moves to an 85:15 an 80:20 methanol to water elution solvent or equivalent, which elutes off the column some or substantially most of the CBD;

then the gradient elution moves to a 90:10 methanol to water elution solution or equivalent, which initially elutes off the column a mix of the remaining CBD and THC, and finally elutes off the column THC; and finally the gradient elution moves to a 100% methanol elution solution, which removes a mix of remaining cannabinoids comprising CBC, CBG, CBN;

n. optionally repeating steps j to m on the first column with at least one second additional elution solution;

o. optionally repeating steps i to m with at least one additional column;

p. optionally mixing the second purified extract with a reaction mixture comprising a reaction solvent and a catalyst, wherein the reaction mixture comprises an aqueous phase and an organic phase;

q. optionally separating the mixture into an aqueous phase and an organic phase (separating the aqueous phase and the organic phase): and r. optionally recovering the organic phase to obtain the substantially pure $\Delta^9$-THC.

In some embodiments, the method further comprises: adding a neutralizing agent to the reaction mixture; and removing all or substantially most of the catalyst and the neutralizing agent before separating the reaction mixture.

In some embodiments, the method further comprises: adding at least one of a stabilization agent and an elimination agent to the reaction mixture; and removing all or substantially most of the at least one of the stabilization agents and the elimination agent before separating the reaction mixture.

In some embodiments, the extract, aliquot or sample comprises at least 25% by weight CBD, or between about 10% to 40% by weight CBD, or between about 5% to 50% by weight CBD.

In some embodiments, at least one of the first elution solvent, the additional elution solvent, the second elution solvent, and the second additional elution solvent comprises methanol, ethanol, propanol, butanol, chloroform, dichloromethane, dichloroethane, acetic acid, formic acid, oxalic acid, glycolic acid, ammonium hydroxide, or combinations thereof.

In some embodiments, the reaction solvent comprises ethylene dichloride, chloroform, methylene dichloride, toluene, xylene, benzene, hexane, pentane, ethyl acetate, propyl acetate, butyl acetate, anisole, cymene, p-cymene, limonene, cumene, carvacrol, terpineol, pinene, linalool, terpinene, citral or combinations thereof.

In some embodiments, the catalyst comprises a Lewis acid or a non-oxidizing acid. In some embodiments, the catalyst comprises p-toluenesulfonic acid In some embodiments, the neutralizing agent comprises an alkali. In some embodiments, the neutralizing agent comprises sodium bicarbonate, sodium carbonate, calcium hydroxide, or ammonium hydroxide, or combinations thereof.

In some embodiments, the stabilization agent is or comprises zinc chloride or methylene chloride, or combinations thereof.

In some embodiments, the method further comprises: adding a second reaction solvent to the organic phase after the mixture is separated.

In some embodiments, the second reaction solvent comprises dimethyl sulfoxide, pyridine, dimethylformamide, methanol, ethylene dichloride, chloroform, propanol, ethanol, isobutanol, formamide, methylene dichloride, butanol, isopropanol, tetrahydrofuran, dioxane, benzene, toluene, xylene, or combinations thereof.

In some embodiments, the elimination agent comprises lithium hydroxide (LiOH), sodium hydroxide (NaOH), potassium hydroxide (KOH), rubidium hydroxide (RbOH), cesium hydroxide (CsOH), magnesium hydroxide ($Mg(OH)_2$), calcium hydroxide ($Ca(OH)_2$), strontium hydroxide $Sr(OH)_2$), barium hydroxide $Ba(OH)_2$), potassium hydride and/or sodium hydride, potassium tert-pentoxide, organic superbases, bispidines, multicyclic polyamines, or organometallic compounds of reactive metals, wherein optionally the reactive metals comprise organolithium, organomagnesium, lithium diisopropylamide, n-butyl lithium and potassium tert-butoxide, sodium methoxide, or sodium ethoxide, lithium nitride, potassium hydride, sodium hydride, or combinations thereof.

In some embodiments, the method further comprises: dissolving, filtering and/or diluting the extract, aliquot or sample in a first solvent before introducing or loading the extract, aliquot or sample into the first chromatography column, or the column at the first station, which can be a second, third, fourth etc. chromatography column.

In some embodiments, the first solvent comprises methanol, ethanol, propanol, isobutanol, butanol, isopropanol, tetrahydrofuran, chloroform, methylene dichloride, dichloroethane, or combinations thereof.

In some embodiments, the method further comprises: filtering the extract, sample or aliquot to remove all or substantially most of the solids and color bodies in the natural or synthetic material before introducing or loading the extract, aliquot or sample into the first column, or any additional column at the first station.

In some embodiments, at least one of the first chromatography column, the second chromatography column, or the at least one additional chromatography column comprises a normal phase chromatography column, a reverse phase chromatography column, or an ion exchange chromatography column.

In some embodiments, the method further comprises measuring the amount of $\Delta^9$-THC, or plurality of cannabinoids or terpenes, in the organic phase.

In some embodiments, the first and second elution solutions are different.

In some embodiments, there are at least 4 columns, at least four elution solvents, and at least four purified extracts, or between about 3 and 30 elution solvents and purified extracts. In some embodiments, the at least four elution solvents are different.

In alternative embodiments, methods and processes comprise a continuous column chromatography process for isolating and/or modifying cannabidiol (CBD) and/or $\Delta^9$ THC and/or $\Delta^8$THC and/or plurality of cannabinoids or terpenes, comprising:

(a) at a first station, loading onto a first column the extract, aliquot or sample of the natural or synthetic source comprising a cannabidiol (CBD) and/or $\Delta^9$ THC and/or $\Delta^8$THC and/or plurality of cannabinoids or terpenes from the natural or the synthetic source, and then moving the first column to a second station;

(b) at the second station, introducing into the first column an elution solvent comprising an 80:20 or a 70:30 methanol to water elution solution or equivalent, which elutes off the first column some or substantially most of the polar compounds and terpenes comprising cannabidiolic acid (CBDA) and tetrahydrocannabinolic acid (THCA), and then moving the first column to a third station;

(c) at the third station, introducing into the first column an elution solvent comprising an 85:15 or an 80:20 methanol to water elution solvent or equivalent, which elutes off the first column some or substantially most of the CBD, and then moving the first column to a fourth station;

(d) at the fourth station, introducing into the first column an elution solvent comprising a 90:10 methanol to water elution solution or equivalent, which elutes off the first column the minor CBD, and some THC, and finally elutes off the column more or substantially most of the THC, then moving the first column to a fifth station;

(e) at the fifth station, introducing into the first column an elution solution comprising a 100% methanol elution solution, which removes a mix of remaining cannabinoids comprising CBC, CBG, CBN, then moving the first column to a sixth station;

(f) at the sixth station, introducing into the first column an elution solution comprising dichloromethane (DCM), chloroform or equivalent to remove or elute off the non-polar compounds reversibly bound to the column, wherein optionally the non-polar compounds comprise cannabidiol (CBD), cannabinol (CBN), cannabigerol (CBG), cannabichromene (CBC), cannabidivarol (CBDV), tetrahydrocannabidiol (THCBD), tetrahydrocannabigerol (THCBG), tetrahydrocannabichromene (THCBC), or tetrahydrocannabidivarol (THCBDV), then moving the first column to a seventh station or back to the first station; and (g) introducing into the first column an 80:20 or a 70:30 methanol to water elution solution or equivalent either at the seventh station or the first station in an amount sufficient to remove all or substantially most of the dichloromethane (DCM), chloroform or equivalent, and if the 80:20 or the 70:30 methanol to water elution solvent or equivalent is introduced at the seventh station, after remove all or substantially most of the dichloromethane (DCM), chloroform or equivalent the first column is moved back to the first station;

wherein one or several fractions are collected at each station, or at least at the first to fifth stations or first to sixth stations.

In alternative embodiments, the method or processes further comprise mixing the isolated cannabidiol (CBD) and/or $\Delta^9$ THC and/or $\Delta^8$THC and/or plurality of cannabinoid fractions or terpenes with a reaction solvent and a catalyst, for example, for converting cannabidiol (CBD) to $\Delta^8$-THC and/or $\Delta^9$-THC, or for converting $\Delta^8$-THC to $\Delta^9$-THC.

In alternative embodiments, provided are methods of purifying a cannabinoid to substantially pure $\Delta^9$-THC from a natural or a synthetic source, e.g., a plant or a microbial material, comprising:

a. providing an extract, aliquot or sample of the natural or synthetic source comprising at least one of cannabidiol (CBD), $\Delta^9$ THC, THC, and plurality of cannabinoids or terpenes from the natural or a synthetic source, wherein the natural or a synthetic source comprises a plant or a microbial material;

b. loading the CBD-, $\Delta^9$ THC-, $\Delta^8$ THC-comprising extract, aliquot or sample on a chromatography column, wherein optionally the chromatography column is a normal phase chromatography column, an ion exchange chromatography column, or a reverse phase chromatography column, and eluting the column with a first elution solution so that all or substantially most of the CBD, $\Delta^9$ THC, $\Delta^8$ THC remains in (or reversibly bound to) the column and the all or substantially most of the remaining natural or synthetic, optionally plant or microbial, material is eluted out of the column;

c. collecting the eluted material and removing all or substantially most of the first elution solution, wherein the first elution solution is substantially free of CBD, $\Delta^9$ THC, $\Delta^8$ THC;

d. eluting some or substantially most of the CBD, $\Delta^9$ THC and/or $\Delta^8$THC from the column with a second elution solution, wherein optionally between about 50% and 99% of the CBD, $\Delta^9$ THC and/or $\Delta^8$THC is eluted from the column, and collecting the CBD, $\Delta^9$ THC, $\Delta^8$ THC, or collecting the CBD, $\Delta^9$ THC, $\Delta^8$ THC elution fractions, wherein one or multiple fractions are collected, and optionally the CBD, $\Delta^9$ THC, $\Delta^8$ THC are collected in separate elution fractions, and removing all or substantially most of the second elution solution, wherein optionally the elution of step (d) is by a gradient elution process, and optionally the elution is by a gradient elution process and the $\Delta^9$ THC and/or $\Delta^8$THC and/or plurality of cannabinoids or terpenes are separately collected in different or separate gradient elution fractions, wherein optionally, if the elution is by a gradient elution process: in a first gradient solvent non-polar compounds and terpenes are eluted off the column; in a second gradient solvent cannabidiol (CBD) is eluted off the column; in a third gradient a CBD/tetrahydrocannabinol (THC) mix is first eluted and then remaining THC is eluted off the column; in a fourth gradient minor cannabinoids are eluted off the column, wherein optionally the minor cannabinoids comprise CBC, CBG, CBN; and, in a fifth gradient solvent all remaining polar compounds are eluted off the column, wherein the remaining polar compounds comprises cannabidiolic acid (CBDA) and tetrahydrocannabinolic acid (THCA);

e. loading the collected CBD, $\Delta^9$ THC, $\Delta^8$ THC on a second chromatography column and eluting the CBD from the second column with a third elution solution (the $\Delta^9$ THC and $\Delta^8$ THC stay on the second column), collecting the second eluted material containing (or comprising) the CBD, and removing all or substantially most of the third elution solvent;

f. eluting the $\Delta^9$ THC and $\Delta^8$ THC from the second column with a fourth elution solution, collecting the fraction, and removing all or substantially most of the fourth elution solution;

g. adding the CBD from the second column to a reaction solvent and adding a catalyst forming a reaction mixture, wherein the reaction mixture comprises an aqueous phase and an organic phase.

In some embodiments, steps b to d are continuously repeated and wherein steps e to g are continuously repeated.

In some embodiments, the method further comprises: adding a neutralizing agent to the mixture; and removing all or substantially most of the catalyst and the neutralizing agent before separating the mixture, and optionally separating the aqueous phase from the organic phase.

In some embodiments, the method further comprises: adding at least one of a stabilization agent and an elimination agent to the mixture; and removing all or substantially most of the at least one of the stabilization agent and the elimination agent before separating the mixture.

In some embodiments, the extract comprises at least 25% CBD by weight, or between about 10% to 40% CBD by weight, or between about 5% to 50% CBD by weight, by weight.

In some embodiments, at least one of the first elution solvent, the second elution solvent, the third elution solvent, and the fourth additional elution solvent comprises methanol, ethanol, propanol, butanol, chloroform, dichloromethane, dichloroethane, acetic acid, formic acid, oxalic acid, glycolic acid, ammonium hydroxide, water, or combinations thereof.

In some embodiments, the reaction solvent comprises ethylene dichloride, chloroform, methylene dichloride, toluene, xylene, benzene, hexane, pentane, ethyl acetate, propyl acetate, butyl acetate, anisole, cymene, p-cymene, limonene, cumene, carvacrol, terpineol, pinene, linalool, terpinene, citral or combinations thereof.

In some embodiments, the catalyst comprises a Lewis acid or a non-oxidizing acid. In some embodiments, the catalyst comprises p-toluenesulfonic acid In some embodiments, the neutralizing agent comprises an alkali. In some embodiments, the neutralizing agent comprises sodium bicarbonate, sodium carbonate, calcium hydroxide or ammonium hydroxide.

In some embodiments, the stabilization agent is or comprises zinc chloride or methylene chloride.

In some embodiments, the method further comprises: adding a second reaction solvent to the organic phase after the mixture is separated.

In some embodiments, the second reaction solvent comprises dimethyl sulfoxide, pyridine, water, dimethylformamide, methanol, ethylene dichloride, chloroform, propanol, ethanol, isobutanol, formamide, methylene dichloride, butanol, isopropanol, tetrahydrofuran, dioxane, benzene, toluene, xylene, or combinations thereof.

In some embodiments, the elimination agent comprises lithium hydroxide (LiOH), sodium hydroxide (NaOH), potassium hydroxide (KOH), rubidium hydroxide (RbOH), cesium hydroxide (CsOH), magnesium hydroxide $(Mg(OH)_2)$, calcium hydroxide $(Ca(OH)_2)$, strontium hydroxide $Sr(OH)_2)$, barium hydroxide $Ba(OH)_2)$, potassium hydride and/or sodium hydride, potassium tert-pentoxide, organic superbases, bispidines, multicyclic polyamines, organometallic compounds of reactive metals, wherein optionally the reactive metals comprise organolithium, organomagnesium, lithium diisopropylamide, sodium methoxide, or sodium ethoxide, or combinations thereof.

In some embodiments, the method further comprises: dissolving, diluting and/or filtering the extract, aliquot or sample comprising the natural or synthetic material in a first solvent before introducing or loading the extract, aliquot or sample into the first column, or before the initial loading of the second or additional columns.

In some embodiments, the first solvent comprises methanol, ethanol, propanol, isobutanol, butanol, isopropanol, tetrahydrofuran, chloroform, methylene dichloride, dichloroethane, water, or combinations thereof.

In some embodiments, the method further comprises: filtering the extract, aliquot or sample comprising the natural or synthetic material to remove all or substantially most of the material's solids and color bodies before introducing or loading the extract, aliquot or sample into the first column, or before the initial loading of the extract, aliquot or sample in the second or additional columns.

In some embodiments, at least one of the columns, or the first and/or the second column comprises a normal phase chromatography column, a reverse phase chromatography column, or an ion exchange chromatography column. In alternative embodiments, all of the columns are the same (e.g., all are normal phase chromatography columns or reverse phase chromatography columns), or the columns differ (e.g., some are normal phase chromatography columns and some are reverse phase chromatography columns or ion exchange chromatography columns).

In some embodiments, the method further comprising measuring the amount of $\Delta^9$-THC, or plurality of cannabinoids or terpenes, in the organic phase.

In some embodiments, the first, second, third, and fourth elution solutions are different.

In alternative embodiments, the natural or synthetic material, or the extract, aliquot or sample, is filtered before being loaded on to the column, and optionally the natural or synthetic material, or the extract, aliquot or sample, is mixed with silica, diatomaceous earth (DE), bentonite clay (BC), or equivalents, or mixtures thereof, before filtering, and optionally the natural or synthetic material, or the extract, aliquot or sample, is chilled before being mixed with the silica, DE, BC or equivalents or is chilled before being filtered.

In alternative embodiments, the microbial material comprises or is derived from a bacterium, an algal cell, a lichen or a yeast, or a recombinant bacterium, algal cell, lichen or yeast cell. In alternative embodiments, the plant material comprises or is derived from a botanical drug substance, including a hemp or a cannabis plant, wherein optionally the cannabis plant is a *Cannabis sativa*, a *Cannabis* chemovar, or variants thereof, or a decarboxylated *Cannabis* plant material. In alternative embodiments, the plant or starting material comprises oils or extracts from a trichome or a trichome fraction of a pubescent plant, or an algae or a lichen; and optionally the oils or extracts are from the plant or microbial material by: washing, contacting or exposing the trichome or trichome fraction, or the pubescent plant, algae or lichen, with: at least one non-polar, organic solvent; at least one polar, organic solvent; or, a mix of at least one non-polar, organic solvent with (and) at least one polar, organic solvent.

Chapt. III In alternative embodiments, provided are methods of and processes for isolating or purifying a cannabinoid or a substantially pure $\Delta^8$-THC from a natural or a synthetic source, e.g., a plant or a microbial material.

In one embodiment, the method comprises:
a. providing an extract, aliquot or sample of the natural or synthetic source comprising at least one of: cannabidiol (CBD), $\Delta^9$ THC, $\Delta^8$ THC, and plurality of cannabinoids or terpenes from the natural or a synthetic source, wherein the natural source comprises a plant or a microbial material;
b. providing a continuous chromatography apparatus comprising a plurality of stations and a plurality of chromatography columns, wherein optionally the plurality of stations and the plurality of chromatography columns comprise at least 2, 3, 4, 5, 6, 7, or 8 or more, or between about 3 and 30, stations and/or chromatography columns; c. introducing or loading the extract, aliquot or sample of the natural or synthetic source into a first column at a first station, wherein CBD, $\Delta^9$ THC, and $\Delta^8$ THC reversibly binds to the first column;
d. moving the first column to a next or second station;
e. eluting the extract from the first chromatography column with a first elution solvent at the next or second station, wherein the first elution solvent does not elute the CBD, $\Delta^9$ THC, and $\Delta^8$ THC from the first column;
f. collecting the first elution fractions from the first column;
g. removing all or substantially most of the first elution solution from the first elution fractions to produce a first purified extract substantially free of CBD, $\Delta^9$ THC, and $\Delta^8$ THC;
h. optionally repeating steps d to g with at least one additional first elution solution;
i. when the first column is moved to the next or second station, introducing or loading the extract into a next or second column at the first station;
j. moving the second column to the next or second station after the first column has been moved to a next or third station;
k. eluting the extract, or material reversibly bound to the first column with a second elution solution at the next or second station to generate one or more second elution fractions, wherein optionally the second elution solution comprises an organic solvent; l. collecting the second elution fractions from the second chromatography column at the second station;
m. removing all or substantially most of the second elution solution from the second elution fractions to produce a second purified extract comprising at least about 75% of CBD, $\Delta^9$ THC, and $\Delta^8$ THC, or between about 60% and 90% of CBD, $\Delta^9$ THC, and $\Delta^8$ THC, or between about 50% and 95% of CBD, $\Delta^9$ THC, and $\Delta^8$ THC, wherein optionally the elution is by a gradient elution process and the $\Delta^9$ THC and/or $\Delta^8$THC and/or plurality of cannabinoids or terpenes are separately collected in different or separate gradient elution fractions, wherein optionally, if the elution is by a gradient elution process: in a first gradient solvent non-polar compounds and terpenes are eluted off the column; in a second gradient solvent cannabidiol (CBD) is eluted off the column; in a third gradient a CBD/tetrahydrocannabinol (THC) mix is first eluted and then remaining THC is eluted off the column; in a fourth gradient remaining cannabinoids are eluted off the column, wherein optionally the remaining cannabinoids comprise CBC, CBG, CBN; and, in a fifth gradient solvent all remaining polar compounds are eluted off the column, wherein the remaining polar compounds comprises cannabidiolic acid (CBDA) and tetrahydrocannabinolic acid (THCA);
n. optionally repeating steps j to m with at least one second additional elution solution;
o. optionally repeating steps i to m with at least one additional column; p. recovering the second purified extract, or recovering the gradient elution fraction, comprising a substantially pure CBD and the organic solvent, wherein optionally if a gradient elution is used the CBD is in one or more elution fractions separate from one or more of the plurality of cannabinoids or terpenes or polar compounds;
q. optionally removing all or substantially most of the organic solvent if an organic solvent is used in the gradient elution fraction;
r. optionally adding a second organic solvent to the second purified extract; s. adding at least one catalyst to the organic phase under an inert atmosphere to catalyze the conversion of CBD to $\Delta^9$-THC and a second order reaction of $\Delta^9$-THC to $\Delta^8$-THC;
t. optionally controlling the reaction temperature to be in a range of between about $-10°$ C. to about $40°$ C. and measuring the rate of reaction by observing the conversion of CBD to $\Delta^9$-THC and second order reaction of $\Delta^9$-THC to $\Delta^8$-THC; u. adding a base to a first organic phase when the $\Delta^9$-THC has been substantially converted to $\Delta^8$-THC;
v. allowing the mixture to separate into an aqueous phase and a second organic phase; and w. recovering the second organic phase comprising the converted $\Delta^8$-THC.

In some embodiments, the method further comprises repeating steps s to w.

In some embodiments, the method further comprises: repeating steps c to m and wherein the extract, aliquot or sample of the natural or synthetic source in step c is replaced with the $\Delta^8$-THC as recovered in step w.

In some embodiments, the extract, aliquot or sample of the natural or synthetic source comprises at least 25% CBD by weight, or between about 10% to 40% CBD by weight, or between about 5% to 50% CBD by weight.

In some embodiments, at least one of the first elution solvent, the additional elution solvent, the second elution solvent, and the second additional elution solvent comprises methanol, ethanol, propanol, butanol, chloroform, dichloromethane, dichloroethane, acetic acid, formic acid, oxalic acid, glycolic acid, ammonium hydroxide, water, or combinations thereof.

In some embodiments, the catalyst comprises a Lewis acid or a non-oxidizing acid. In some embodiments, the catalyst comprises p-toluenesulfonic acid In some embodiments, the base comprises sodium bicarbonate.

In some embodiments, the method further comprises: dissolving, dissolving and/or diluting the extract, aliquot or sample of the natural or synthetic source in a first solvent before introducing or loading the extract, aliquot or sample of the natural or synthetic source into the first chromatography column, or loading the extract, aliquot or sample into the second or additional chromatography columns.

In some embodiments, the first solvent comprises methanol, ethanol, propanol, isobutanol, butanol, isopropanol, tetrahydrofuran, chloroform, methylene dichloride, dichloroethane, water, or combinations thereof.

In some embodiments, the method further comprises: filtering the extract, aliquot or sample of the natural or synthetic source to remove all or substantially most of the material's solids and color bodies before introducing or loading the extract, aliquot or sample of the natural or synthetic source into the first column, or before the initial loading of the extract, aliquot or sample in the second or additional columns.

In some embodiments, at least one of the first chromatography column, the second chromatography column, or the at least one additional chromatography column comprises a normal phase chromatography column, a reverse phase chromatography column, or an ion exchange chromatography column.

In some embodiments, at least one of the organic solvents and the second organic solvent comprises methanol, ethanol, propanol, isobutanol, butanol, isopropanol, tetrahydrofuran, chloroform, methylene dichloride, dichloroethane, water, or combinations thereof.

In some embodiments, the first and second elution solutions are different.

In some embodiments, there are at least 4 columns, at least four elution solutions, and at least four purified extracts.

In some embodiments, the at least four elution solvents are different.

In alternative embodiments, the natural or synthetic material, or the extract, aliquot or sample, is filtered before being loaded on to the column, and optionally the natural or synthetic material, or the extract, aliquot or sample, is mixed with silica, diatomaceous earth (DE), bentonite clay (BC), or equivalents, or mixtures thereof, before filtering, and optionally the natural or synthetic material, or the extract, aliquot or sample, is chilled before being mixed with the silica, DE, BC or equivalents or is chilled before being filtered.

In alternative embodiments, the microbial material comprises or is derived from a bacterium, an algal cell, a lichen or a yeast, or a recombinant bacterium, algal cell, lichen or yeast cell.

In alternative embodiments, the plant material comprises or is derived from a botanical drug substance, including a hemp or a cannabis plant, wherein optionally the cannabis plant is a *Cannabis sativa*, a *Cannabis* chemovar, or variants thereof, or a decarboxylated *Cannabis* plant material. In alternative embodiments, the plant or starting material comprises oils or extracts from a trichome or a trichome fraction of a pubescent plant, or an algae or a lichen; and optionally the oils or extracts are from the plant or microbial material by: washing, contacting or exposing the trichome or trichome fraction, or the pubescent plant, algae or lichen, with: at least one non-polar, organic solvent; at least one polar, organic solvent; or, a mix of at least one non-polar, organic solvent with (and) at least one polar, organic solvent.

Chapt. IV

In alternative embodiments, provided are methods of or processes for purifying cannabinoids from a natural or a synthetic source, e.g., a plant or a microbial material.

In one embodiment, the method comprises:

a. providing an extract, aliquot or sample comprising at least one of cannabidiol (CBD), $\Delta^9$ THC, $\Delta^8$ THC, and plurality of cannabinoids or terpenes from the natural or a synthetic source, wherein optionally the natural or a synthetic source comprises or is derived from a plant material;

b. providing a continuous chromatography apparatus comprising a plurality of stations and a plurality of chromatography columns, wherein optionally the plurality of stations and the plurality of chromatography columns comprise at least 2, 3, 4, 5, 6, 7, or 8 or more, or between about 3 and 30, stations and/or chromatography columns;

c. introducing or loading the extract, aliquot or sample into a first column at a first station;

d. moving the first column to a next or second station and a second column to the first station;

e. eluting the extract, aliquot or sample from the first chromatography column with a first elution solvent at the next or second station, wherein optionally the elution is by a gradient elution process and the $\Delta^9$ THC and/or $\Delta^8$THC and/or plurality of cannabinoids or terpenes are separately collected in different or separate gradient elution fractions, wherein optionally, if the elution is by a gradient elution process: in a first gradient solvent non-polar compounds and terpenes are eluted off the column; in a second gradient solvent cannabidiol (CBD) is eluted off the column; in a third gradient a CBD/tetrahydrocannabinol (THC) mix is first eluted and then remaining THC is eluted off the column; in a fourth gradient remaining cannabinoids are eluted off the column, wherein optionally the remaining cannabinoids comprise CBC, CBG, CBN; and, in a fifth gradient solvent all remaining polar compounds are eluted off the column, wherein the remaining polar compounds comprises cannabidiolic acid (CBDA) and tetrahydrocannabinolic acid (THCA);

f. collecting the first elution fractions from the first column at the second station;

g. removing all or substantially most of the first elution solution from the first elution fractions to produce a first purified extract, wherein optionally the first purified extract comprises THC, CBC, CBG, CBN, CBDA and/or THCA, and the THC, CBC, CBG, CBN, CBDA and/or THCA are eluted separately in different elution fractions to yield separate purified first extracts;

h. optionally repeating steps d to g with at least one additional first or plurality of elution solution(s);

i. when the first column is moved to the next or third station, the second column is moved to the second station where extract or reversibly bound material is eluted with the first elution solution, and another batch of the extract, aliquot or sample is introduced or loaded into a next or third column at the first station;

j. moving the second column to the next or second station;

k. eluting the extract from the second column with a first elution solution at the next or second station;

l. collecting the second elution fractions from the second column at the second station, wherein optionally the elution is by a gradient elution process and the $\Delta^9$ THC and/or $\Delta^8$THC and/or plurality of cannabinoids or terpenes are separately collected in different or separate gradient elution fractions, wherein optionally, if the elution is by a gradient elution process: in a first gradient solvent non-polar compounds and terpenes are eluted off the column; in a second gradient solvent cannabidiol (CBD) is eluted off the column; in a third gradient a CBD/tetrahydrocannabinol (THC) mix is first eluted and then remaining THC is eluted off the column; in a fourth gradient remaining cannabinoids are eluted off the column, wherein optionally the remaining cannabinoids comprise CBC, CBG, CBN; and, in a fifth gradient solvent all remaining polar compounds are eluted off the column, wherein the remaining polar compounds comprises cannabidiolic acid (CBDA) and tetrahydrocannabinolic acid (THCA);

m. removing all or substantially most of the second elution solution from the second elution fractions to produce a second purified extract;

n. optionally repeating steps j to m with at least one second additional elution solution; and o. optionally repeating steps i to m with at least one additional column.

In some embodiments, the extract comprises at least 25% CBD by weight, or between about 10% to 40% CBD by weight, or between about 5% to 50% CBD by weight.

In some embodiments, at least one of the first elution solution, the additional elution solution, the second elution solution, and the second additional elution solution comprises methanol, ethanol, propanol, butanol, chloroform, dichloromethane, dichloroethane, acetic acid, formic acid, oxalic acid, glycolic acid, ammonium hydroxide, water, or combinations thereof.

In some embodiments, the method further comprises: dissolving the extract in a first solvent before introducing the extract into the first chromatography column or the second chromatography column.

In some embodiments, the first solvent comprises methanol, ethanol, propanol, isobutanol, butanol, isopropanol, tetrahydrofuran, chloroform, methylene dichloride, dichloroethane, water, or combinations thereof.

In some embodiments, at least one of the first chromatography column, the second chromatography column, or the at least one additional chromatography column comprises a normal phase chromatography column, a reverse phase chromatography column, or an ion exchange chromatography column.

In some embodiments, the first and second elution solutions are different.

In some embodiments, there are at least 2, 3, 4, 5, 6, 7, or 8 or more columns, with at least 2, 3, 4, 5, 6, 7, or 8 or more corresponding elution solvents, and at least 2, 3, 4, 5, 6, 7, or 8 or more corresponding purified extracts.

In some embodiments, the at least 2, 3, 4, 5, 6, 7, or 8 or more elution solutions are different.

In some embodiments, the method further comprises measuring the amount of the cannabinoid in the first or second purified extract.

In alternative embodiments, the natural or synthetic material, or the extract, aliquot or sample, is filtered before being loaded on to the column, and optionally the natural or synthetic material, or the extract, aliquot or sample, is mixed with silica, diatomaceous earth (DE), bentonite clay (BC), or equivalents, or mixtures thereof, before filtering, and optionally the natural or synthetic material, or the extract, aliquot or sample, is chilled before being mixed with the silica, DE, BC or equivalents or is chilled before being filtered.

In alternative embodiments, the microbial material comprises or is derived from a bacterium, an algal cell, a lichen or a yeast, or a recombinant bacterium, algal cell, lichen or yeast cell.

In alternative embodiments, the plant material comprises or is derived from a botanical drug substance, including a hemp or a cannabis plant, wherein optionally the cannabis plant is a *Cannabis sativa*, a *Cannabis* chemovar, or variants thereof, or a decarboxylated *Cannabis* plant material. In alternative embodiments, the plant or starting material comprises oils or extracts from a trichome or a trichome fraction of a pubescent plant, or an algae or a lichen; and optionally the oils or extracts are from the plant or microbial material by: washing, contacting or exposing the trichome or trichome fraction, or the pubescent plant, algae or lichen, with: at least one non-polar, organic solvent; at least one polar, organic solvent; or, a mix of at least one non-polar, organic solvent with (and) at least one polar, organic solvent.

Chapt. V In alternative embodiments, provided are methods of and processes for purifying a cannabinoid from a natural or a synthetic source, e.g., a plant or a microbial material, to a purified mixture comprising $\Delta^8$tetrahydrocannabinol ($\Delta^8$-THC) and $\Delta^9$tetrahydrocannabinol ($\Delta^9$-THC).

In alternative embodiments, the method comprises:

a. providing an extract, aliquot or sample comprising at least one of cannabidiol (CBD), $\Delta^9$ THC, $\Delta^8$ THC, and plurality of cannabinoids or terpenes from the natural or a synthetic source, wherein optionally the natural or a synthetic source comprises or is derived from a plant or a microbial material;

b. providing a continuous chromatography apparatus comprising a plurality of stations and a plurality of chromatography columns, wherein optionally the plurality of stations and the plurality of chromatography columns comprise at least 2, 3, 4, 5, 6, 7, or 8 or more, or between about 3 and 30, stations and/or chromatography columns; c. introducing or loading the extract, aliquot or sample into a first column at a first station, wherein the at least one of cannabidiol (CBD), $\Delta^9$ THC, $\Delta^8$ THC, and plurality of cannabinoids or terpenes reversibly bind to the first column, wherein optionally some of or substantially most of the extract, aliquot or sample material not reversibly bound to the first column at the first station is removed with a first wash solution before the column is moved to a next or a second station; d. moving the first column to a next or a second station;

e. eluting the extract, aliquot or sample from the first chromatography column with a first elution solution at the next or second station, wherein the first elution solution does not elute the CBD, $\Delta^9$ THC and $\Delta^8$ THC, which remains on the first chromatography column;

f. collecting the first elution fractions from the first column;

g. removing all or substantially most of the first elution solution from the first elution fractions off the first column to produce a first purified extract substantially free of CBD, $\Delta^9$ THC, and $\Delta^8$ THC;

h. optionally repeating steps d to g with at least one additional elution solution off the first column;

i. when the first column is moved to the next or second station, a second column is introduced or moved into the first station where another batch of the extract, aliquot or sample is introduced or loaded;

j. moving the second column to the next or second station when the first column is moved to a third station;

k. eluting the extract or material reversibly bound on the first column (which comprises at least one of cannabidiol (CBD), $\Delta^9$ THC, $\Delta^8$ THC, and plurality of cannabinoids or terpenes) from the first column with a second elution solution at the next or second station, wherein optionally the elution using the second elution solution is by a gradient elution process and the $\Delta^9$ THC and/or $\Delta^8$THC and/or plurality of cannabinoids or terpenes are separately collected in different or separate gradient elution fractions, wherein optionally, if the elution is by a gradient elution process: in a first gradient solvent non-polar compounds and terpenes are eluted off the column; in a second gradient solvent cannabidiol (CBD) is eluted off the column; in a third gradient solvent a CBD/tetrahydrocannabinol (THC) mix is first eluted and then remaining THC is eluted off the column; in a fourth gradient remaining cannabinoids are eluted off the column, wherein optionally the remaining cannabinoids comprise CBC, CBG, CBN; and, in a fifth gradient solvent all remaining polar compounds are eluted off the column, wherein the remaining polar compounds comprises cannabidiolic acid (CBDA) and tetrahydrocannabinolic acid (THCA);

l. collecting second elution fractions from the first chromatography column;

m. removing all or substantially most of the second elution solution from the first elution fractions to produce a second purified extract comprising at least 75% of the total amount of CBD, $\Delta^9$ THC, and $\Delta^8$ THC, or between about 60% and 90% of CBD, $\Delta^9$ THC, and $\Delta^8$ THC, or between about 50% and 95% of CBD, $\Delta^9$ THC, and $\Delta^8$ THC;

n. optionally repeating steps j to m with at least one second additional elution solution;

o. optionally repeating steps i to m with at least one additional column;

p. mixing the second purified extract with a reaction mixture comprising an organic solvent and a catalyst;

q. reacting the mixture at a controlled temperature for a period of time, wherein optionally the period of time is between about 30 seconds and 30 minutes;

r. adding a base to the mixture;

s. separating the mixture into an aqueous phase and an organic phase, if an organic solvent is used:

t. loading the organic phase onto a normal phase chromatography column;

u. eluting the organic phase with a second organic solvent; and v. recovering a third purified extract comprising at least about 30%, 40%, 50% or 60% or more of $\Delta^8$-THC and $\Delta^9$-THC.

In some embodiments, the method further comprises repeating steps p to v.

In some embodiments, the base comprises an alkali metal hydrogen carbonate, an alkali metal carbonate, lithium hydroxide (LiOH), sodium hydroxide (NaOH), potassium hydroxide (KOH), rubidium hydroxide (RbOH), cesium hydroxide (CsOH), magnesium hydroxide (Mg(OH)), calcium hydroxide (Ca(OH)), strontium hydroxide (Sr(OH)), barium hydroxide (Ba(OH)).

In some embodiments, the controlled temperature is in a range of −10° C. to 40° C.

In some embodiments, the extract comprises at least 25% CBD by weight, or between about 10% to 40% CBD by weight, or between about 5% to 50% CBD by weight.

In some embodiments, at least one of the first elution solution, the additional elution solution, the second elution solution, and the second additional elution solution comprises methanol, ethanol, propanol, butanol, chloroform, dichloromethane, dichloroethane, acetic acid, formic acid, oxalic acid, glycolic acid, ammonium hydroxide, water, or combinations thereof.

In some embodiments, the organic solvent comprises ethylene dichloride, chloroform, methylene dichloride, toluene, xylene, benzene, hexane, pentane, or combinations thereof.

In some embodiments, the catalyst comprises a Lewis acid or a non-oxidizing acid. In some embodiments, the catalyst comprises p-toluenesulfonic acid In some embodiments, the method further comprises dissolving, diluting or filtering the extract, aliquot or sample of the natural or synthetic source in a first solvent before introducing or loading the extract, aliquot or sample of the natural or synthetic source into the first chromatography column, or the second or additional chromatography columns at the first station.

In some embodiments, the first solvent comprises methanol, ethanol, propanol, isobutanol, butanol, isopropanol, tetrahydrofuran, chloroform, methylene dichloride, dichloroethane, water, or combinations thereof.

In some embodiments, the method further comprises filtering the extract, aliquot or sample of the natural or synthetic source to remove all or substantially most of the material's solids and color bodies before introducing or loading the extract, aliquot or sample into the first column, or before the initial loading of the extract, aliquot or sample in the second or additional columns at the first station.

In some embodiments, at least one of the first chromatography column, the second chromatography column, or the at least one additional chromatography column comprises a normal phase chromatography column, a reverse phase chromatography column, or an ion exchange chromatography column.

In some embodiments, the method further comprises measuring the amount of $\Delta^9$-THC in the organic phase.

In some embodiments, the first and second elution solutions are different.

In some embodiments, there are at least 4 columns, at least four elution solutions, and at least four purified extracts.

In some embodiments, the at least four elution solutions are different.

In alternative embodiments, the natural or synthetic material, or the extract, aliquot or sample, is filtered before being loaded on to the column, and optionally the natural or synthetic material, or the extract, aliquot or sample, is mixed with silica, diatomaceous earth (DE), bentonite clay (BC), or equivalents, or mixtures thereof, before filtering, and optionally the natural or synthetic material, or the extract, aliquot or sample, is chilled before being mixed with the silica, DE, BC or equivalents or is chilled before being filtered.

In alternative embodiments, the microbial material comprises or is derived from a bacterium, an algal cell, a lichen or a yeast, or a recombinant bacterium, algal cell, lichen or yeast cell.

In alternative embodiments, the plant material comprises or is derived from a botanical drug substance, including a hemp or a cannabis plant, wherein optionally the cannabis plant is a *Cannabis sativa*, a *Cannabis* chemovar, or variants thereof, or a decarboxylated *Cannabis* plant material. In alternative embodiments, the plant or starting material comprises oils or extracts from a trichome or a trichome fraction of a pubescent plant, or an algae or a lichen; and optionally the oils or extracts are from the plant or microbial material by: washing, contacting or exposing the trichome or trichome fraction, or the pubescent plant, algae or lichen, with: at least one non-polar, organic solvent; at least one polar, organic solvent; or, a mix of at least one non-polar, organic solvent with (and) at least one polar, organic solvent.

Chapt. VI In alternative embodiments, provided are methods or processes for obtaining or purifying a substantially pure $\Delta^8$tetrahydrocannabinol ($\Delta^8$THC) and/or $\Delta^9$tetrahydrocannabinol ($\Delta^9$THC) and optionally a plurality of cannabinoids or terpenes from a natural or a synthetic source, wherein the natural or the synthetic source comprises a cannabidiol (CBD) and optionally a plurality of cannabinoids or terpenes, wherein optionally the natural source comprises a plant, an algal or a microbial material, or a material derived from a plant, lichen, algal, yeast or microbial material or source, and optionally the plurality of cannabinoids comprise tetrahydrocannabinol (THC), cannabinol (CBN), cannabigerol (CBG), cannabichromene (CBC), cannabidivarol (CBDV), tetrahydrocannabidiol (THCBD), tetrahydrocannabigerol (THCBG), tetrahydrocannabichromene (THCBC) or tetrahydrocannabidivarol (THCBDV) or a combination thereof, wherein the method comprises:

(a) obtaining, providing or being provided a first extract, aliquot or sample of the natural or synthetic source from the natural or the synthetic source;

(b) dissolving the first extract, aliquot or sample in a first reaction solvent;

(c) adding a catalyst to the first extract, aliquot or sample and the first reaction solvent to generate a first reaction mixture, wherein optionally the catalyst is added before, simultaneous with or after addition of the first reaction solvent to the first extract, aliquot or sample, thereby reacting: the first extract, aliquot or sample; the catalyst; and, the first reaction solvent, under reaction conditions comprising between about 5° C. to about 70° C., or between about 10° C. to about 60° C., for between about 1 to 30 hours (h), or 4 to 24 h, or 6 to 15 h, or about 8 h, wherein optionally reacting converts the CBD to a mixture comprising (unreacted) CBD, $\Delta$8-THC and $\Delta^9$-THC;

(d) adding a neutralizing agent to the first reaction mixture;

(e) removing the catalyst and the neutralizing agent (or substantially removing all or most of the catalyst and the neutralizing agent) from the first product mixture to generate a first reaction product, wherein optionally removing the catalyst and the neutralizing agent comprises adding a base, wherein optionally the base comprises NaHCO$_3$, wherein optionally the removing or substantially removing most or all of the catalyst comprising adding a NaHCO$_3$, and the NaHCO$_3$ and water create a salt of the catalyst that reports to the water phase and is decanted off;

and optionally adding a second reaction solvent to the first product mixture; and optionally removing all or substantially all or most of the first reaction solvent and the second reaction solvent, thereby leaving or generating a second product mixture comprising a (unreacted) CBD, $\Delta$8-THC and $\Delta^9$-THC, wherein optionally the first and/or second reaction solvent is removed or substantially removed by evaporation, optionally by rotary evaporation (rotovap), rising film or vertical long tube evaporator, or falling film evaporation, or the first and/or second reaction solvent is removed or substantially removed by a process comprising use of selective membranes, and optionally:

(i) adding a stabilization agent to the second product mixture;

(ii) adding an elimination agent to the second product mixture;

(iii) removing (or removing of substantially all or most of) of the stabilization agent and the elimination agent, thereby leaving or generating a third product mixture comprising a CBD, $\Delta$8-THC and $\Delta^9$-THC;

and optionally if the second reaction solvent is not removed in step (e), adding a third reaction solvent of opposite polarity to the second reaction solvent in the third product mixture;

(f) removing or substantially removing all or most of the second reaction solvent, if present (if not removed in step (e)), and removing all or substantially most or all of the third reaction solvent of opposite polarity, if added, thereby leaving a fourth product mixture comprising a (unreacted) CBD, $\Delta$8-THC and $\Delta^9$-THC, wherein optionally the first, second and/or the third reaction solvent are removed or substantially removed by evaporation, optionally by rotary evaporation (rotovap), rising film or vertical long tube evaporator, or falling film evaporation, or by a process comprising use of selective membranes, and optionally the fourth product mixture comprises less than about 10% unreacted CBD from the natural source or the synthetic source;

(g) dissolving, adding or mixing in the third or the fourth product mixture in (or adding the third or fourth product mixture to) a third reaction solvent, wherein optionally the third reaction solvent is the same or substantially the same as the first and/or the second solvent, wherein optionally the first, second and/or third reaction solvent is removed or substantially removed by evaporation, optionally by rotary evaporation (rotovap), rising film or vertical long tube evaporator, or falling film evaporation, to generate a fifth product mixture substantially lacking a solvent, or the first, second and/or third reaction solvent is removed or substantially removed by a process comprising use of selective membranes;

(h) loading the dissolved, added or mixed in the first, second, third or fourth product mixture (or mixture of the first, second, third or fourth product mixture and third reaction solvent) onto a first chromatography column, or if the first, second and/or third reaction solvent is removed or substantially removed (e.g, by evaporation or selective membrane), re-dissolving the fifth product mixture in a fourth reaction solvent and loading the fifth product mixture in the fourth reaction solvent into or onto the first chromatography column, wherein optionally the fourth reaction solvent is the same or substantially the same as the first, second and/or third solvent, and optionally the first chromatography column is a normal phase chromatography column or a reverse phase chromatography column, wherein the plurality of cannabinoids or terpenes are reversible bound to the first chromatography column; and (i) eluting the dissolved third or the fourth product mixture from the first column with a first elution solution, wherein optionally the elution with the first elution solution comprises use of a gradient elution process, and unreacted CBD, the $\Delta^9$ THC and/or the $\Delta^8$ THC and/or plurality of cannabinoids or terpenes are separately collected in different or separate gradient elution fractions, and optionally the elution conditions comprise use of between about 50:1 to 500:1 mobile phase eluent to product (or first extract, aliquot or sample) loaded on the chromatography column, and optionally individually or severally collecting the $\Delta^9$ THC and/or the $\Delta^8$ THC and/or the plurality of cannabinoids or terpenes from the first elution solution in separate gradient elution fractions, and optionally removing all or substantially most or all of the elution solvent before or after collecting the $\Delta^9$ THC and/or the $\Delta^8$ THC and/or the plurality of cannabinoids or terpenes from the first elution solution, wherein optionally the elution solvent is removed or substantially removed by evaporation, optionally by rotary evaporation (rotovap), rising film or vertical long tube evaporator, or falling film evaporation, or the elution solvent is removed or substantially removed by a process comprising use of selective membranes, to generate a fifth product mixture substantially lacking a solvent, thereby obtaining or purifying one or more chromatography elution fractions comprising at least one, or several, or a plurality of, substantially pure preparations or eluates of a plurality of cannabinoids or terpenes, wherein optionally the obtained or purified plurality of cannabinoids comprises, in one or separate chromatography elution fractions: unreacted cannabidiol (CBD); a mix of CBD and tetrahydrocannabinol (THC); $\Delta^9$ THC; $\Delta^8$ THC; $\Delta^9$ THC and $\Delta^8$ THC; tetrahydrocannabinol (THC); cannabinol (CBN); cannabigerol (CBG); cannabichromene (CBC); cannabidivarol (CBDV); tetrahydrocannabidiol (THCBD); tetrahydrocannabigerol (THCBG); tetrahydrocannabichromene (THCBC); and/or tetrahydrocannabidivarol (THCBDV).

For example, in alternative embodiments a reaction product is generated using a catalyst, then removing or substantially removing most or all of the catalyst by adding a baking soda (NaHCO$_3$) and water, and the NaHCO$_3$ and water create a salt of the catalyst that reports to the water phase, which is decanted off; and thereafter the solvent is removed, e.g., by evaporation or use of one or more selective membranes; and thereafter the reaction product is loaded on a chromatography column, e.g., a continuous chromatography system; and thereafter the reaction products or products are eluted, e.g., with an alcohol such as methanol and water. Use of continuous chromatography systems for the purification of reaction products is described herein.

In alternative embodiments of methods or process as provided herein:

the CBD content of the extract, aliquot or sample material is greater than about 15%, 20%, 25%, 50%, 75%, 90% or 99% by weight, or is between about 50% and 99% by weight, or is between about 20% and 95% by weight, of the extract, aliquot or sample material;

the first, second and/or third reaction solvent comprises anisole, p-cymene, methanol, propanol, ethanol, isobutanol, butanol, isopropanol, tetrahydrofuran, chloroform, acetone, hexane, methylene dichloride, dichloroethane, or equivalents thereof or a mixture or a combination thereof, and optionally the first, second and/or third reaction solvent comprises chloroform, methylene dichloride and methanol, propanol and/or ethanol;

the first chromatography column comprises a silica gel, an alumina or an ion exchange material, or the chromatography column is an ion exchange column, and optionally the ion exchange column comprises an anion exchange material or equivalents thereof, and optionally the first chromatography column is a normal phase chromatography column, an ion exchange column, a reverse phase column, or equivalents thereof;

the first elution solution comprises a solvent, and optionally the solvent in the first elution solution comprises a one or a mixture of: (a) ethylene dichloride, chloroform or methylene dichloride; and, an alcohol comprising methanol, ethanol, propanol or butanol or a mixture thereof; (b) an acid comprising acetic acid, formic acid, oxalic acid, glycolic acid or a mixture thereof; (c) ammonium hydroxide, (d) a dichloromethane, dichloroethane, or chloroform and methanol, or ethanol, or (e) any combination of (a) to (d);

the first reaction solvent comprises ethylene dichloride, chloroform, methylene dichloride, toluene, xylene, benzene, hexane, pentane, ethyl acetate, propyl acetate, butyl acetate, anisole, cymene, p-cymene, limonene, cumene, carvacrol, terpineol, pinene, linalool, terpinene, citral or a mixture or a combination thereof;

the catalyst is or comprises a Lewis acid or a non-oxidizing acid catalyst, and optionally the Lewis acid comprises BF$_3$Et$_2$O (boron trifluoride diethyl etherate), boron trifluoride or p-toluenesulfonic acid (PTSA or pTsOH) or tosylic acid (TsOH), and optionally the non-oxidizing acid catalyst comprises dilute hydrochloric acid or dilute sulfuric acid, wherein optionally a dilute acid is between about 30%, 20%, 10%, 5% or 1% and 0.1% acid by volume acid diluted in water;

the neutralizing agent is or comprises an alkali, or the neutralizing agent is or comprises sodium bicarbonate, sodium carbonate, calcium hydroxide or ammonium hydroxide or a mixture or a combination thereof;

the stabilization agent is or comprises zinc chloride or methylene chloride;

the second or third reaction solvent comprises dimethyl sulfoxide, water, dimethylformamide, methanol, saline, chloroform, propanol, ethanol, isobutanol, formamide, butanol, isopropanol, tetrahydrofuran, dioxane, benzene, toluene. xylene, ethylene dichloride, chloroform, methylene dichloride, toluene, xylene, benzene, hexane, pentane, ethyl acetate, propyl acetate, butyl acetate, anisole, cymene, p-cymene, limonene, cumene, carvacrol, terpineol, pinene, linalool, terpinene, citral or a mixture or a combination thereof, and optionally the second or third reaction solvent comprises chloroform, hexane, dichloromethane, dichloroethane, benzene or toluene or a mixture or a combination thereof;

the elimination agent is or comprises a strong base, and optionally the strong base comprises: lithium hydroxide (LiOH), sodium hydroxide (NaOH), potassium hydroxide (KOH), rubidium hydroxide (RbOH), cesium hydroxide (CsOH), magnesium hydroxide (Mg(OH)$_2$), calcium hydroxide (Ca(OH)$_2$), strontium hydroxide Sr(OH)$_2$), barium hydroxide Ba(OH)$_2$), potassium hydride and/or sodium hydride, potassium tert-pentoxide, organic superbases, bispidines, multicyclic polyamines, organometallic compounds of reactive metals, wherein optionally the reactive metals comprise organolithium, organo-magnesium, lithium diisopropylamide, n-butyl lithium and potassium tert-butoxide, sodium methoxide, or sodium ethoxide; and optionally the elimination agent is or comprises potassium tert-pentoxide, lithium diisopropylamide or potassium tert-butoxide or mixtures or combinations thereof;

the elution solution is or comprises a solvent or mixture of solvents;

the methods or processes further comprise filtering the extract, aliquot or sample before its being loaded on to the first chromatography column, wherein optionally the filtering comprises use of an about 10 to 500 um filter, and optionally the filter comprises filter paper or filter media, and optionally the extract, aliquot or sample is mixed with silica, diatomaceous earth (DE), bentonite clay (BC), or equivalents, or mixtures thereof, before the filtering, and optionally the extract, aliquot or sample is chilled before being mixed with the silica, DE, BC or equivalents or is chilled before the filtering; and/or the microbial, algal, a lichen or a yeast material comprises or is derived from a bacterium, an algae, a lichen or a yeast, or if or is derived from a recombinant bacterium, lichen, algal cell or yeast cell, or the plant material comprises or is derived from a botanical substance, and optionally the botanical drug substance comprises or is derived from: hemp or a cannabis plant, wherein optionally the cannabis plant is a *Cannabis sativa*, a *Cannabis* chemovar, or variants thereof, or a decarboxylated *Cannabis* plant material, and optionally the plant or starting material comprises oils or extracts from a trichome or a trichome fraction of a pubescent plant, or an algae or a lichen, and optionally the oils or extracts are from the plant or microbial material by: washing, contacting or exposing the trichome or trichome fraction, or the pubescent plant, algae or lichen, with: at least one non-polar, organic solvent; at least one polar, organic solvent; or, a mix of at least one non-polar, organic solvent with (and) at least one polar, organic solvent.

1. A method or process for obtaining or purifying a substantially pure $\Delta^8$-THC and $\Delta^9$ THC from a natural or a synthetic source, wherein the natural or a synthetic source comprises $\Delta^8$-THC and $\Delta^9$ THC and a plurality of cannabinoids or terpenes, wherein optionally the natural source comprises a plant, algal, yeast, lichen or a microbial material, or a material derived from a plant source or plant, algal, yeast, lichen or microbial material, comprising:

(a) obtaining or being provided a first extract, aliquot or sample of the natural or synthetic source, wherein the first extract, aliquot or sample comprises a cannabidiol (CBD) from the natural or the synthetic source;

(b) dissolving the first extract, aliquot or sample in a first reaction solvent;

(c) adding a catalyst to the first extract, aliquot or sample and the first reaction solvent to generate a first reaction mixture, wherein the optionally the catalyst is added before, simultaneous with or after addition of the first reaction solvent to the first extract, aliquot or sample;

(d) reacting the first extract, aliquot or sample, with the catalyst and the first reaction solvent, under reaction conditions comprising between about 5° C. to about 70° C., or between about 10° C. to about 60° C., for between about 1 to 30 hours (h), or 4 to 24 h, or 6 to 15 h, or about 8 h, wherein optionally the reacting converts the CBD to a mixture comprising (unreacted) CBD, $\Delta^8$-THC and $\Delta^9$-THC;

(e) adding a neutralizing agent to the first reaction mixture;

(f) removing or substantially removing most or all of the catalyst and the neutralizing agent from the first reaction mixture to generate a first reaction product, wherein optionally the removing or substantially removing most or all of the catalyst comprising adding a $NaHCO_3$, and the $NaHCO_3$ and water create a salt of the catalyst that reports to the water phase and is decanted off;

and optionally removing all or substantially most or all of the first reaction solvent, thereby leaving a first reaction product comprising (unreacted) CBD, $\Delta^8$-THC and $\Delta^9$-THC;

(h) dissolving the first reaction product in a second solvent, wherein optionally the second solvent is the same or substantially the same as the first solvent;

(i) loading the dissolved first reaction product onto a first chromatography column, wherein optionally the first chromatography column is a normal phase chromatography column or a reverse phase chromatography column, wherein the $\Delta^8$-THC and/or $\Delta^9$ THC and/or the plurality of cannabinoids or terpenes are reversibly bound to the first chromatography column; and (j) eluting the dissolved first reaction product from the first column with an or at least one elution solution, wherein optionally the eluting comprises use of a gradient elution process and the $\Delta^9$ THC and/or $\Delta^8$THC and/or the plurality of cannabinoids or terpenes are separately collected in different or separate gradient elution fractions, and optionally the eluting comprises use of an isocratic simulated moving bed (SMB) elution process and the $\Delta^9$ THC and/or $\Delta^8$THC and/or the plurality of cannabinoids or terpenes are separately collected in different or separate elution fractions, and optionally collecting the plurality of cannabinoids from the elution solution, and/or removing all or substantially most of the elution solvent, thereby obtaining or purifying a substantially pure $\Delta^9$ THC and/or $\Delta^8$THC or plurality of cannabinoids or terpenes, wherein optionally the plurality of cannabinoids comprises tetrahydrocannabinol (THC), cannabinol (CBN), cannabigerol (CBG), cannabichromene (CBC), cannabidivarol (CBDV), tetrahydrocannabidiol (THCBD), tetrahydrocannabigerol (THCBG), tetrahydrocannabichromene (THCBC) or tetrahydrocannabidivarol (THCBDV).

2. The method or process of claim 16, further comprising dissolving or mixing in or adding the substantially pure $\Delta^9$ THC and/or $\Delta^8$THC or plurality of cannabinoids or terpenes in a solvent to make a mixture of solvent and $\Delta^9$ THC and/or $\Delta^8$ THC or plurality of cannabinoids or terpenes, and loading the mixture onto a second chromatography column, wherein optionally the second chromatography column is the same column or the same type of column as the first chromatography column, and eluting the dissolved first reaction product from the first column with an elution solution, wherein optionally the eluting comprises use of a gradient elution process and the $\Delta^9$ THC and/or $\Delta^8$THC and/or the plurality of cannabinoids or terpenes are separately collected in different or separate gradient elution fractions, and optionally the eluting comprises use of an isocratic simulated moving bed (SMB) elution process and the $\Delta^9$ THC and/or $\Delta^8$ THC and/or the plurality of cannabinoids or terpenes are separately collected in different or separate elution fractions, and optionally collecting the plurality of cannabinoids or terpenes from the elution solution, and/or removing all or substantially most of the elution solvent, thereby obtaining or purifying a substantially pure $\Delta^9$ THC and/or $\Delta^8$ THC or plurality of cannabinoids or terpenes, wherein optionally the plurality of cannabinoids comprises tetrahydrocannabinol (THC), cannabinol (CBN), cannabigerol (CBG), cannabichromene (CBC), cannabidivarol (CBDV), tetrahydrocannabidiol (THCBD), tetrahydrocannabigerol (THCBG), tetrahydrocannabichromene (THCBC) or tetrahydrocannabidivarol (THCBDV).

In alternative embodiments, provided are methods or processes for making a $\Delta^9$tetrahydrocannabinol ($\Delta^9$THC) from cannabidiol (CBD), comprising:

(a) mixing a CBD isolate or a natural or a synthetic source comprising a cannabidiol (CBD) with a solvent (wherein optionally the solvent comprises chloroform, p-cymene or dichloromethane (DCM)) at a ratio of 0.25 to 0.5:1 mol, and a Lewis acid catalyst at between about 0.01 to 0.25 mol (wherein optionally the Lewis acid catalyst comprises PTSA), at about ambient temperature, or at a temperature of between about 5° C. to 60° C. temp, or at about 30° C. to 40° C., and at about ambient pressure, for between about 4 to 24 hours (h), or for about 6 to 10 h, or for 8 h, and allowing the reaction to proceed to generate a reaction product mixture comprising $\Delta^9$-THC and unreacted CBD, optionally the reaction is allowed to proceed only to the point where the ratio of $\Delta^9$-THC and CBD are approximately 50:50, or 30:70, or 70:30, or 20:80, or 80:20, or 90:10, or 10:90;

(b) adding a base or caustic, optionally $NaHCO_3$, to neutralize to neutralize the catalyst, and optionally also adding water to wash out the catalyst, and if water is added, decanting the water off;

(c) evaporating off substantially all or most of the solvent, optionally by rotary evaporation (rotovap), rising film or vertical long tube evaporator, or falling film evaporation or by a process comprising use of selective membranes;

(d) loading the reaction product mixture $\Delta^9$-THC:CBD mix into a continuous chromatography column or continuous chromatography column system, or the continuous chromatography column system comprises use of a normal phase, an ion exchange or a reverse phase resin, wherein optionally the continuous chromatography column is a normal phase, an ion exchange or a reverse phase resin, and optionally the continuous chromatography column is eluted with an eluent solution comprising a polar solvent or solvents (wherein optionally the polar solvent comprises water and/or an alcohol, wherein optionally the alcohol comprises methanol or ethanol) or equivalents, by running an isocratic gradient; and (e) collecting eluate (or elution) fractions which separately comprise substantially pure CBD, a CBD/THC mix and a THC-only comprising fraction.

In alternative embodiments, the CBD and/or the CBD/THC fractions are recycled back to the same continuous chromatography column, or another continuous chromatography column, or to a different chromatography column, or recycled to another process, for further purification.

The details of one or more exemplary embodiments of the invention are set forth in the accompanying drawings and the description below. Other features, objects, and advantages of embodiments as provided herein will be apparent from the description and drawings, and from the claims.

All publications, patents, patent applications cited herein are hereby expressly incorporated by reference for all purposes.

DESCRIPTION OF DRAWINGS

The drawings set forth herein are illustrative of exemplary embodiments provided herein and are not meant to limit the scope of the invention as encompassed by the claims.

Like reference symbols in the various drawings indicate like elements.

DETAILED DESCRIPTION

Chapter I

Figure 1:
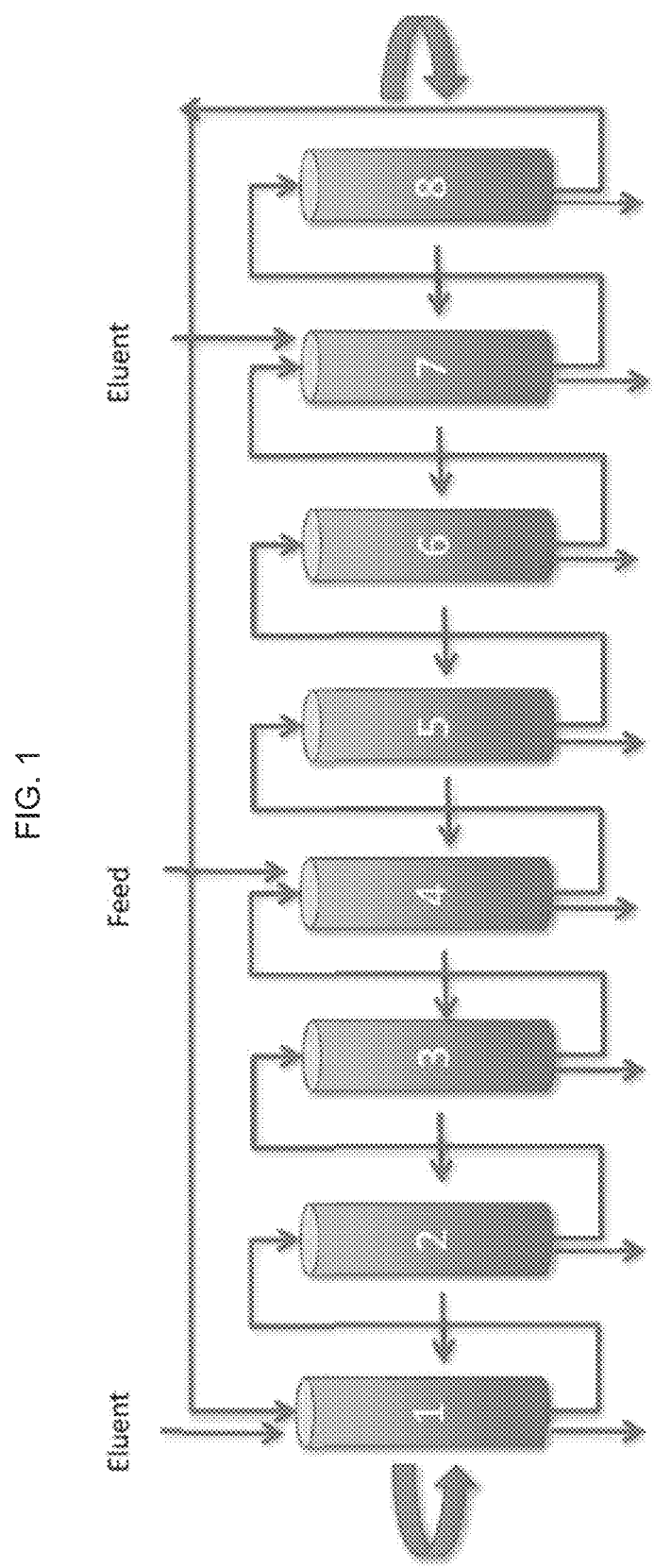
FIG. 1 schematically illustrates an exemplary method as provided herein using a continuous chromatography apparatus comprising a plurality of stations and a plurality of chromatography columns.

In alternative embodiments, provided are continuous isolation and purification processes for preparing a substantially pure cannabidiol or a product enriched in cannabidiol from natural or synthetic sources, including plant or microbial material extracts. In alternative embodiments, provided herein are improved methods for converting cannabidiol (CBD) to $\Delta^8$-THC and $\Delta^9$-THC, including a purification and conversion process based on a simple combination of continuous chromato-graphic gradient elutions and semi continuous isomerization reactions. This exemplary process is simple, efficient and economic.

In alternative embodiments, provided are methods of preparing cannabinoids in substantially pure form starting from plant extract material and conversion of the purified CBD to form both $\Delta^8$-THC and $\Delta^9$-THC and subsequent purification of the produced $\Delta^8$-tetrahydrocannabinol into $\Delta^9$-tetrahydrocannabinol using continuous chromatography.

In alternative embodiments, provided are processes for producing and isolating cannabinoids from cannabis and hemp extracts which contain cannabinoids in minute amounts. In alternative embodiments, provided are processes for producing and isolating cannabinoids from natural materials, including plant or plant extracts, microbes, or botanical drug substances, or synthetically and semi-synthetically prepared cannabinoid products, or from recombinantly engineered microbes, e.g., yeasts or bacteria recombinantly engineered to express one or more cannabinoids. In one embodiment, exemplary methods are inexpensive and provide specific cannabinoid concentrates (e.g., of CBD, $\Delta^8$-THC, $\Delta^9$-THC) of high purity.

In one embodiment, exemplary methods provide a simple and economical continuous process for separating and concentrating cannabinoids from solvent-extracted cannabinoid containing materials. In one embodiment, exemplary methods provide a method that first converts the substantially isolated CBD into a mixture of $\Delta^8$-THC and $\Delta^9$-THC, and then subsequently purifies and/or isolates the $\Delta^8$-THC and $\Delta^9$-THC. In alternative embodiments, the solvent-extracted cannabinoid containing materials are derived from synthetic or biological materials such as hemp and Cannabis or botanical drug substances, or from microbial materials; and the solvent extraction methods can be polar solvent extractions, nonpolar solvent extractions, or the solvent extraction methods can comprise use of super critical carbon dioxide or mixtures thereof. The solvent extraction methods can extract cannabinoids substantially from the synthetic or biological, e.g., plant, matter, along with other plant matter comprising lipids, waxes, monoterpenes, sesquiterpenes, hydrocarbons, alkaloids, flavonoids and chlorophylls.

In alternative embodiments, methods provided herein comprise subjecting cannabinoid containing solvent extract starting materials to a number of chromatographic resins in various contacting steps using various gradient elution solutions.

In alternative embodiments, the cannabinoids which can be fractionated and isolated using methods as provided herein, or which can be produced in reactions as provided herein, or from which the solvent extracts are derived can be from, or can comprise: $\Delta^8$tetrahydrocannabinol ($\Delta^8$ THC); $\Delta^9$tetrahydrocannabinol ($\Delta^9$ THC); cannabidiol (CBD); cannabinol (CBN); cannabigerol (CBG); cannabichromene (CBC); cannabidivarol (CBDV); tetrahydrocannabidiol (THCBD); tetrahydrocannabigerol (THCBG); tetrahydrocannabichromene (THCBC); tetrahydrocannabidivarol (THCBDV), or combinations thereof, including carboxylic acid precursors of the foregoing compounds and related naturally occurring compounds and their derivatives.

In alternative embodiments, provides are methods of preparing or obtaining a substantially pure cannabinoid or a product enriched in a given cannabinoid comprising:

(i) obtaining an extract or extract solution containing a cannabinoid or a cannabinoid acid from a synthetic or biological, e.g., plant, material;

(ii) optionally filtering the extract of step (i) to remove all or substantially all solids and color bodies;

(iii) removing the extract solvent (as an extract fraction);

(iv) continuously loading of an amount of extract solution over a defined time increment over multiple stationary phase resins columns such as a normal phase, reverse phase and/or ion exchange chromatographic resin, e.g., at first station;

(v) continuously eluting the extract solution using multiple defined gradient elution solutions at specific time increments and volumes, e.g., at a second station;

(vi) continuously collecting the gradient elution fractions;

(vii) removing of the gradient elution solution from the produced fractions to generate a substantially purified extract;

(viii) optionally loading of specific first gradient elution fractions on a reverse phase, ion exchange or normal chromatographic resin;

(ix) continuously eluting the first gradient elution fractions with a second gradient elution solvent; and, (x) removing of the second gradient elution solvent from the produced fractions to produce a purified extract.

In alternative embodiments, the methods further comprise:

a step (xi): loading of first and second gradient elution solvents onto an ion exchange chromatographic resin;

a step (xii): eluting an extract solution from the ion exchange chromatographic resin of step (x) using a gradient solvent and collecting the gradient elution fractions; and (xiii) removing the gradient elution solvent from the produced fractions of step (xii) to produce purified and substantially purified extract.

In alternative embodiments, provided are methods of substantially converting CBD to $\Delta^8$ THC and $\Delta^9$-THC comprising:

(a) providing a reaction mixture comprising a catalyst in an organic solvent;

(b) adding CBD material, e.g., a CBD purified or isolated using steps (vi) and steps (xiii), above;

(c) mixing said reaction mixture;

(d) reacting mixture for a period of time at a controlled temperature;

(e) adding a base to the reaction mixture;

(f) allowing the mixture to separate into an aqueous phase and an organic phase;

(g) removing the organic phase; and, (h) loading the organic phase onto a normal phase chromatography column (i) eluting the organic phase with an organic solvent and recovering substantially pure CBD, $\Delta^8$ THC and $\Delta^9$ THC optionally, repeating steps (a) through (i).

In alternative embodiments, a "substantially pure" preparation of cannabinoid is defined as a preparation having a chromatographic purity (of the desired cannabinoid or cannabinoid acid) of greater than about 75%, or greater than about 96%, or greater than about 97%, or greater than about 98%, or greater than about 99%, or greater than about 99.5%, or between about 70% and 99.9%, as determined by area normalization of an HPLC profile.

In alternative embodiments, the term "product enriched in a given cannabinoid" encompasses preparations having at least about 50%, or greater than about 75%, or greater than about 90%, 95% or 98%, or between about 50% and 99.9%, chromatographic purity, for the desired cannabinoid.

In alternative embodiments, the term "about" is within 20% of the stated value, or 19%, or 18%, or 17%, or 16%, or 15%, or 14%, or 13%, or 12%, or 11%, or 10%, or 9%, or 8%, or 7%, or 6%, or 5%, or 4%, or 3%, or 2%, or 1%, or 0.5%, or 0.1%, or 0.05%, or 0.01%, or is between 20% and 0.01% of the stated value.

In alternative embodiments, a non-purified, or non-substantially purified, product can comprise a greater proportion of impurities, non-target materials and/or plurality of cannabinoids or terpenes than a "substantially pure" preparation. The cannabinoid can be (e.g., a cannabinoid purified or isolated by, or made by a reaction of, a method as provided herein can be): $\Delta^8$-tetrahydrocannabinol ($\Delta^8$-THC); $\Delta^9$-tetrahydrocannabinol ($\Delta^9$-THC); cannabidiol (CBD); cannabinol (CBN); cannabigerol (CBG); cannabichromene (CBC); cannabidivarol (CBDV); tetra-hydrocannabidiol (THCBD); tetra-hydrocannabigerol (THCBG); tetra-hydrocannabichromene (THCBC); or, tetra-hydrocannabidivarol (THCBDV); a carboxylic acid precursor of the foregoing compounds; and related naturally occurring compounds and their derivatives.

In alternative embodiments, the term "cannabinoids", e.g., a cannabinoid purified or isolated by, or made by a reaction of a process as provided herein, includes or refers to a family of natural products that can contain a 1,1'-dimethyl-pyrane ring, a variedly derivatized aromatic ring and/or a variedly unsaturated cyclohexyl ring and their immediate chemical precursors.

In alternative embodiments, the term "cannflavins", e.g., a cannflavin purified or isolated by, or made by a reaction of a process as provided herein, includes or refers to a family of natural products that can contain a 1,4-pyrone ring fused to a variedly derivatized aromatic ring and linked to a second variedly derivatized aromatic ring.

In alternative embodiments, the term "Lewis acid" refers to a powerful electron pair acceptor; and examples include but are by no means limited to $BF_3Et_2O$ (boron trifluoride diethyl etherate), p-toluenesulfonic acid and boron trifluoride.

In alternative embodiments, the term "non-oxidizing acid" refers to hydrobromic, hydrochloric, hydrofluoric, acetic, benzoic, chloroacetic, formic, phosphoric, sulfuric, trifluoroacetic and oxalic acids.

In alternative embodiments, the term "essential oils", e.g., an essential oil used as a starting material in a process as provided herein, or an essential oil that may be isolated by a process as provided herein, includes or refers to a family of natural products that can contain a multiple of the 5-membered isoprene unit variedly substituted, often cyclized to form one or more ring systems; they can also contain series of aldehydes and/or ketones and esters of a variety of carboxylic acid substituted compounds.

In alternative embodiments, provided are methods for extracting and/or purifying cannabinoids from any natural or synthetic sources, including plant or microbial material or extracts known to contain such cannabinoids, cannflavins and essential oils; and, optionally to purify cannflavins and to optionally purify essential oils. In alternative embodiments, the extract is passed through a series of chromatographic columns, for example, a normal phase column, a reversed phase column or an ion exchange column as a continuous simulated moving bed configuration.

In one embodiment, the chromatographic column is arranged for gradient elution fractioning using normal phase, reverse phase and/or ion exchange chromatography. In one embodiment $\Delta^9$-THC and CBD are fractionated out of the eluent. For example, in one embodiment, as the extract is passed over the column, $\Delta^9$-THC and CBD are differentially retained or detained (e.g., reversibly bound) on the column. As a result, as the extract comes off the column after gradient elution transition, the initial fractions eluted off the column will be (substantially) free of $\Delta^9$-THC and CBD. The fractions free of $\Delta^9$-THC and CBD are pooled, thereby producing an extract with $\Delta^9$-THC and CBD substantially removed (e.g., in alternative embodiments, "substantially removed" or "substantially fractionated" means at least 85%, 90%, 95%, 98%, 99% or 99.5% or more removed or fractionated).

In some embodiments, (substantially) only $\Delta^9$-THC is substantially fractionated out of the eluent. For example, in one embodiment, as the extract or pooled fractions from a previous normal phase, reverse phase and/or ion exchange elution are passed over the column, $\Delta^9$-THC is differentially retained or detained (e.g., reversibly bound) on the column. As the extracts pooled from previous elution fractions come off the column, the initial fractions eluted off the column will be free of $\Delta^9$-THC. These fractions free of $\Delta^9$-THC are pooled, thereby producing an extract with $\Delta^9$-THC substantially removed (e.g., in alternative embodiments, "substantially removed" or "substantially fractionated" means at least 85%, 90%, 95%, 98%, 99% or 99.5% or more removed or fractionated).

In some embodiments, when using a continuous chromatography apparatus or device, a series of columns are arranged, for example, 3, 4, 5, 6, 7, 8, 9, or 10 or more, or between 3 and 30, columns are arranged in a continuous rotation traveling through a series of contact points where gradient elution solutions and extract solution are introduced at fixed points for a period of time allowing for continuous loading and elution, and collection of fractions. The first column is loaded with extract solution at the first position (or station). The first column is then moved to the second position where the first gradient elution is introduced (or loaded) while at the same time the second column is loaded with extract solution at position one. The first column then rotates (i.e., is moved) to the third position where the second gradient solvent is introduced, the second column moves to the second position where the first gradient solvent is introduced and the third column is loaded with extract solution at position one. The first column then moves to the fourth position where the third gradient solvent is introduced, the second column moves to the third position where the second gradient solvent is introduced, the third column moves to the second position where the first gradient solvent is introduced and the fourth column is loaded with extract solution at position one. The first column then moves to the fifth position where the fourth gradient solvent is introduced, the second column moves to the fourth position where the third gradient solvent is introduced, the third column moves to the third position where the second gradient solvent is introduced, the fourth column moves to the second position where the first gradient solvent is introduced and the fifth column is loaded with extract solution at position one. The first column then moves to the sixth position where the fifth gradient solvent is introduced, the second column moves to the fifth position where the fourth gradient solvent is introduced, the third column moves to the fourth position where the third gradient solvent is introduced, the fourth column moves to the third position where the second gradient solvent is introduced, the fifth column moves to the second position where the first gradient solvent is introduced and the sixth column is loaded with extract solution at position one. The first column then moves or returns to the first position where extract solution is loaded, the second column moves to the sixth position where the fifth gradient solvent is introduced, the third column moves to the fifth position where the fourth gradient solvent is introduced, the fourth column moves to the fourth position where the third gradient solvent is introduced, the fifth column moves to the third position where the second gradient solvent is introduced and the sixth column moves to the second position where the first gradient solvent is introduced. In a particular embodiment, the first gradient solvent elutes CBD, CBG and CBN and is substantially fractionated in the eluent.

For example, in one embodiment, as the extract or pooled fractions from a normal phase, reverse phase and/or ion exchange elution are passed over the column, CBD, CBG and CBN is differentially produced in the eluent (e.g., by use of a gradient elution process). In a particular embodiment, second gradient solvent elutes CBD, which is substantially fractionated in the eluent. For example, in one embodiment, as the extract or pooled fractions from a normal phase, reverse phase and/or ion exchange elution are passed over the column, CBD is differentially produced in the eluent. In a particular embodiment, the third gradient solvent elutes CBD and $\Delta^9$-THC and is substantially fractionated in the eluent. For example, in one embodiment, as the extract or pooled fractions from a normal phase, reverse phase and/or ion exchange elution are passed over the column, CBD and $\Delta^9$-THC is differentially produced in the eluent. In a particular embodiment the fourth gradient elutes $\Delta^9$-THC and is substantially fractionated in the eluent. For example, in one embodiment, as the extract or pooled fractions from a normal phase, reverse phase and/or ion exchange elution are passed over the column, $\Delta^9$-THC is differentially produced in the eluent. In a particular embodiment the fifth gradient elutes CBC, THC-A, terpenes and $\Delta^9$-THC and is substantially fractionated in the eluent. For example, in one embodiment, as the extract or pooled fractions from a normal phase, reverse phase and/or ion exchange elution are passed over the column, CBC, THC-A, terpenes and $\Delta^9$-THC is differentially produced in the eluent.

In some embodiments, when using a continuous chromatography apparatus or device, a series of columns are arranged, for example, 3, 4, 5, 6, 7, 8, 9, or 10 or more, or between 3 and 30, columns are arranged in a continuous rotation traveling through a series of contact points where gradient elution solvents and extract solution are introduced at fixed points for a period of time allowing for continuous loading and elution, and collection of fractions. The first column is loaded with extract solution at the first position (or station). The first column is then moved to the second position where the first gradient elution solvent is introduced (or loaded) while at the same time the second column is loaded with extract solution at position one. The first column then rotates (i.e., is moved) to the third position where the second gradient solvent is introduced, the second column moves to the second position where the first gradient solvent is introduced, and the third column is loaded with extract solution at position one. The first column then moves to the fourth position where the third gradient solvent is introduced, the second column moves to the third position where the second gradient solvent is introduced, the third column moves to the second position where the first gradient solvent is introduced, and the fourth column is loaded with extract solution at position one. The first column then moves to the fifth position where the fourth gradient solvent is introduced, the second column moves to the fourth position where the third gradient solvent is introduced, the third column moves to the third position where the second gradient solvent is introduced, the fourth column moves to the second position where the first gradient solvent is introduced and the fifth column is loaded with extract solution at position one. The first column then moves to the sixth position where the fifth gradient solvent is introduced, the second column moves to the fifth position where the fourth gradient is introduced, the third column moves to the fourth position where the third gradient solvent is introduced, the fourth column moves to the third position where the second gradient solvent is introduced, the fifth column moves to the second position where the first gradient solvent is introduced and the sixth column is loaded with extract solution at position one. The first column then moves or returns to the first position where extract solution is loaded, the second column moves to the sixth position where the fifth gradient solvent is introduced, the third column moves to the fifth position where the fourth gradient solvent is introduced, the fourth column moves to the fourth position where the third gradient solvent is introduced, the fifth column moves to the third position where the second gradient solvent is introduced and the sixth column moves to the second position where the first gradient solvent is introduced. In a particular embodiment the first gradient solvent elutes CBD, CBG and CBN and is substantially fractionated in the eluent. For example, in one embodiment, as the extract or pooled fractions from a normal phase, reverse phase and/or ion exchange elution are passed over the column, CBD, CBG and CBN is differentially produced in the eluent (e.g., by use of a gradient elution process). In a particular embodiment second gradient solvent elutes CBD and is substantially fractionated in the eluent. For example, in one embodiment, as the extract or pooled fractions from a normal phase, reverse phase and/or ion exchange elution are passed over the column, CBD is differentially produced in the eluent. In a particular embodiment the third gradient solvent elutes CBD and $\Delta^9$-THC and is substantially fractionated in the eluent. For example, in one embodiment, as the extract or pooled fractions from a normal phase, reverse phase and/or ion exchange elution are passed over the column, CBD and $\Delta^9$-THC is differentially produced in the eluent. In a particular embodiment, the fourth gradient elutes $\Delta^9$-THC and is substantially fractionated in the eluent. For example, in one embodiment, as the extract or pooled fractions from a normal phase, reverse phase and/or ion exchange elution are passed over the column, $\Delta^9$-THC is differentially produced in the eluent. In a particular embodiment the fifth gradient elutes CBC, THC-A, terpenes and $\Delta^9$-THC and is substantially fractionated in the eluent. For example, in one embodiment, as the extract or pooled fractions from a normal phase, reverse phase and/or ion exchange elution are passed over the column, CBC, THC-A, terpenes and $\Delta^9$-THC is differentially produced in the eluent.

The second gradient solvent n containing CBD is combined with a Lewis acid or non-oxidizing acid catalyst, optionally additional CBD or substantially pure CBD and/or $\Delta 8$-tetrahydrocannabinol ($\Delta 8$-THC) and/or $\Delta 9$-tetrahydrocannabinol ($\Delta 9$-THC) can be added to the reaction mixture, mixing said reaction mixture for a period of time; adding a neutralizing agent to said mixture; filtration of catalyst and neutralizing agent from mixture; optionally allowing mixture to separate into an aqueous and organic phase; optionally adding organic phase to a chromatography column and eluting the ($\Delta 8$-THC) and/or $\Delta 9$-tetrahydrocannabinol ($\Delta 9$-THC) from the organic phase. The tetrahydrocannabinol can then be combined with suitable excipients known in the art, thereby forming a pharmaceutical composition. In one embodiment, the mixture is allowed to separate into an aqueous phase and an organic phase; and optionally the process further comprises removing the organic phase.

In some embodiments, (substantially) only CBD is substantially fractionated out of the eluent. That is, as the extract or pooled fractions from a previous normal phase, reverse phase and/or ion exchange elution are passed over the column, CBD is differentially retained or detained (e.g., reversibly bound) on the column. As a result, as the extract or pooled previous elution fractions comes off the column, the initial fractions eluted off the column will be (substantially) free of CBD. These fractions free of CBD are pooled, thereby producing an extract with CBD substantially removed (e.g., in alternative embodiments, "substantially removed" or "substantially fractionated" means at least 85%, 90%, 95%, 98%, 99% or 99.5% or more removed or fractionated).

In some embodiments, $\Delta^9$-THC carboxylic acid species or $\Delta^9$-tetrahydrocannabinolic acid (THCA) and the CBD carboxylic acid species cannabidiolic acid (CBDA) are fractionated out of out of the eluent. For example, in one embodiment, as the extract or pooled fractions from a first elution are passed over the column, $\Delta^9$-THCA and CBDA are differentially retained or detained (e.g., reversibly bound) on the column. As a result, as the extract or pooled first elution fractions comes off the column, the initial fractions eluted off the column will be (substantially) free of $\Delta^9$-THCA and CBDA. These fractions (substantially) free of $\Delta^9$-THCA and CBDA are pooled, thereby producing an extract with $\Delta^9$-THCA and CBDA substantially removed (e.g., in alternative embodiments, "substantially removed" or "substantially fractionated" means at least 85%, 90%, 95%, 98%, 99% or 99.5% or more removed or fractionated).

In some embodiments, the $\Delta^9$-THC can be eluted from the column, extracted or concentrated, for purifying, or substantially purifying, $\Delta^9$-THC. In alternative embodiments, the chromatographic column is arranged for fractionating (e.g., sequentially fractionating) a specific cannabinoid or groups of cannabinoids or their carboxylic acid species, cannflavin or essential oil or class of cannabinoids, cannflavins or essential oils out of the eluent, for example, cannabidiol (CBD), cannabinol (CBN), cannabigerol (CBG), cannabichromene (CBC), cannabidivarol (CBDV), tetrahydrocannabidiol (THCBD), tetrahydrocannabigerol (THCBG), tetrahydrocannabichromene (THCBC), tetrahydrocannabidivarol (THCBDV), $\Delta^8$-THC, the carboxylic acid precursors of the foregoing compounds, and related naturally occurring compounds and their derivatives. In alternate embodiments, the chromatographic column is arranged for fractionating (e.g., sequentially fractionating) cannflavins and related naturally occurring compounds and their derivatives. In alternate embodiments, the system is arranged to fractionate the components of essential oils. The list of compounds provided herein is not exhaustive and is in no way intended to be limiting. In these embodiments, the compound(s) of interest are retained or detained (e.g., reversibly bound) on the column so that fractions (alternatively, the last fractions) of the extract eluted from the column contain the compounds(s) of interest. In alternative embodiments, fractions containing the compound(s) of interest are pooled. In some embodiments, different compounds can be extracted with different solvents and then combined into a single extract. As will be appreciated by one knowledgeable in the art, in this manner, several different cannabinoids could be purified from a single extract.

Simulated Moving Bed Chromatography

Figure 2:
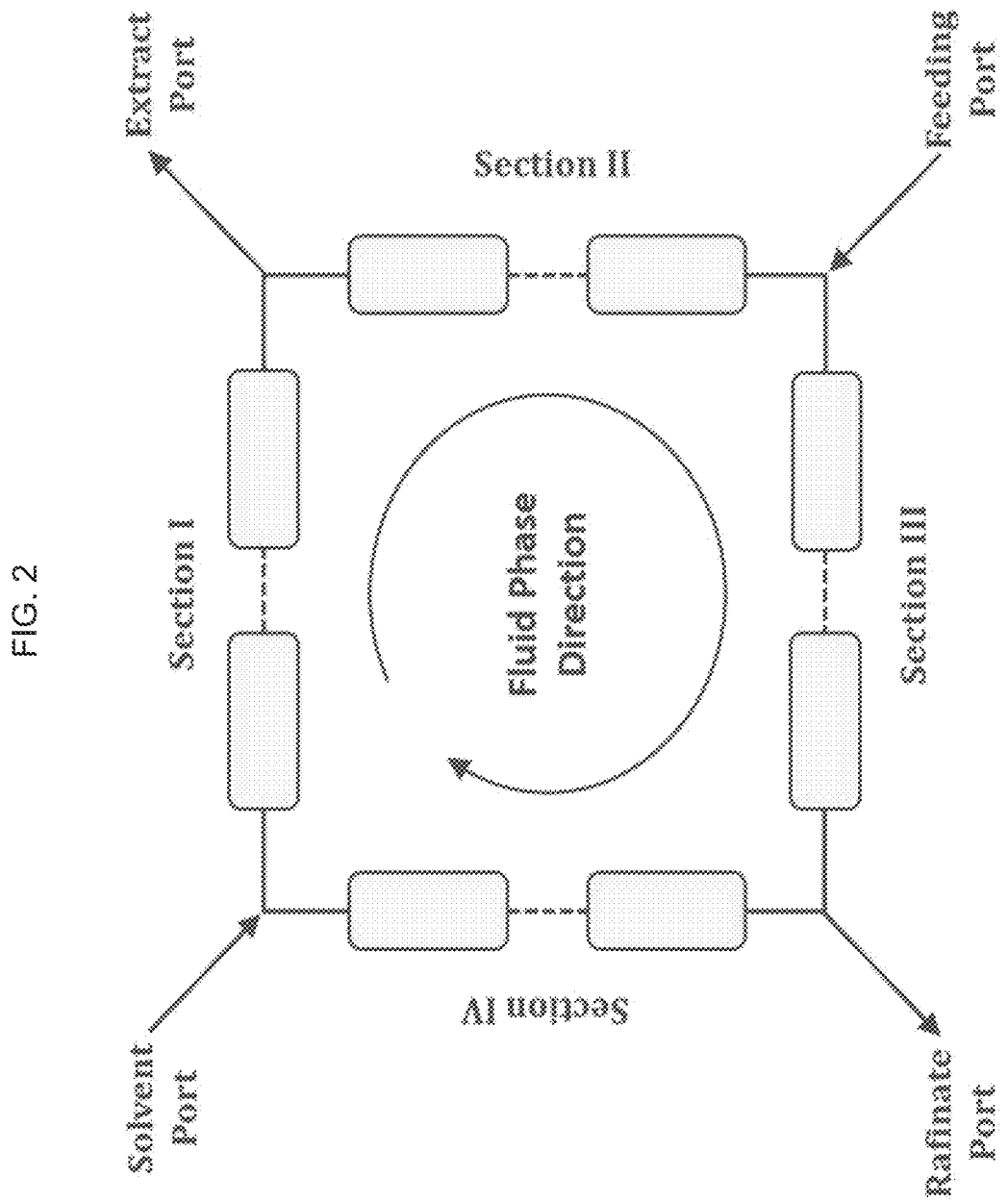
FIG. 2 schematically illustrates an exemplary "simulated moving bed" (SMB) chromatograph apparatus and process as provided herein.

In alternative embodiments, the extract is passed through a series of chromatographic columns, for example, a normal phase column, a reversed phase column or an ion exchange column as a continuous simulated moving bed configuration, also called "simulated moving bed" (SMB) chromatography, for example, as illustrated in FIG. 2. Simulated moving bed chromatography (SMB chromatography) is a continuous process based on the true moving bed principle, in which the solid phase moves in the opposite direction to the liquid phase and is therefore not stationary. Due to this opposing movement two pure compounds can be isolated or a pure compound can be isolated from a complex mixture. The moving solid phase on which this concept relies, however, is technically not feasible and therefore simulated. This is implemented by arranging several preparative columns connected in series and periodically changing the valve setting so that a movement of the solid phase in the opposite direction of the flow of the liquid phase is simulated. The system is continuously fed with a feed mixture comprising the compounds to be separated and an eluant while a raffinate (a liquid from which impurities have been removed by solvent extraction) and an extract are continuously withdrawn from the system. The system is therefore divided into four different separation zones, in each of which the same number of columns are distributed. By periodically switching the feed, eluant, extract and raffinate ports in the same direction, each column passes through each zone once per cycle. The feed mixture is fed into the system between zones II and III, in which the actual separation occurs. Zones I and IV are regeneration zones. The parameters, which are important for the SMB principle, are the periodical change of the position of the ports as well as the different flow rates in the four zones. These four flow rates are regulated by four pumps. The extract pump in zone HI and the raffinate pump in zone IV are inside the column circle, the eluant and the feed pump are located outside of the column circle.

In alternative embodiments, the objectives given above are met by an exemplary SMB method as provided herein, which comprises purifying one or two cannabinoid compounds, comprising the steps:

(a) providing a (starting) mixture comprising at least two cannabinoid compounds obtained by partial protonation of one or more of its isomers and optionally one or more further organic compounds, and (b) simultaneously:

(i) continuously feeding the mixture of step (i) through a feed port into a simulated moving bed chromatographic apparatus comprising at least four columns connected in series and containing a stationary phase, (ii) continuously feeding eluant into the apparatus through an eluant port, (iii) continuously withdrawing the extract through an extract port, and (iv) continuously withdrawing the raffinate through a raffinate port, wherein the extract and/or the raffinate respectively comprise(s) one purified cannabinoid compound.

In alternative embodiments, an exemplary process comprises:

mixing a CBD isolate or a natural or a synthetic source comprising a cannabidiol (CBD) with a solvent at a ratio of between about 0.25 to 0.5:1 mol, and a Lewis acid catalyst at between about 0.005 mol to 0.3 mol, or between about 0.01 mol to 0.25 mol, at about ambient temperature, or at a temperature of between about 5° C. to 60° C. temp, or at about 30° C. to 40° C., and at about ambient pressure, for between about 4 to 24 hours (h), or for about 6 to 10 h, or for 8 h, and allowing the reaction to proceed to generate a reaction product mixture comprising $\Delta^9$-THC and unreacted CBD, and optionally the reaction is allowed to proceed only to the point where the ratio of $\Delta^9$-THC and CBD are approximately 50:50, or 30:70, or 70:30, or 20:80, or 80:20, or 90:10, or 10:90;

adding a base or caustic, optionally $NaHCO_3$, to neutralize to neutralize the catalyst, and optionally also adding water to wash out the catalyst, and if water is added, decanting the water off;

evaporating off substantially all or most of the solvent, optionally by rotary evaporation (rotovap), rising film or vertical long tube evaporator, or falling film evaporation, or by a process comprising use of selective membranes, loading the reaction product mixture $\Delta^9$-THC:CBD mix into a continuous chromatography column or continuous chromatography column system, wherein optionally the continuous chromatography column is a normal phase, an ion exchange or a reverse phase resin, or the or continuous chromatography column system comprises use of a normal phase, an ion exchange or a reverse phase resin, and optionally the continuous chromatography column is eluted with an eluent solution comprising a polar solvent or solvents (wherein optionally the polar solvent comprises water and/or an alcohol, wherein optionally the alcohol comprises methanol or ethanol) or equivalents, by running an isocratic gradient, collecting eluate (or elution) fractions which separately comprise substantially pure CBD, a CBD/THC mix and a THC-only comprising fraction.

In alternative embodiments, the CBD and/or the CBD/THC fractions are recycled back to the continuous chromatography column, or another chromatography column, or another process, for purification.

In the alternative embodiment where the reaction is only allowed proceed to generate a reaction product mixture comprising about 50:50 $\Delta^9$-THC and unreacted CBD, the partial conversion of CBD to $\Delta^9$-THC prevents substantial formation of $\Delta^8$-THC and side reactions; for example, at the approximately 50:50 CBD/THC range of substrate to product the result is about 2% to about 4% $\Delta^8$-THC.

As described above, SMB chromatography allows separation and purification of one or simultaneously two desired product compounds, the stronger adsorbing compound is obtained as the extract and the weaker adsorbing compound is obtained as the raffinate. Thus, by practicing this SMB exemplary method as provided herein, a mixture comprising at least two cannabinoid compounds together, such as a reaction mixture from a protonation step, can provide highly pure products in large yields.

The at least two cannabinoid compounds present in the mixture provided in step (a) of the SMB exemplary method (i.e., (a) providing a (starting) mixture comprising at least two cannabinoid compounds obtained by partial protonation of one or more of its isomers and optionally one or more further organic compounds) are likely very similar in chemical structure and therefore also in their physical properties. Consequently, they may be particularly hard to separate. Using this exemplary SMB method, however, the cannabinoid compound(s) can efficiently be separated from each other, e.g., substantially separated from each other.

In alternative embodiments of this SMB exemplary method, the one or more further organic compound(s) present in the starting mixture of step (a) may be any compound(s) selected from the starting materials or side products of the partial protonation, which are not cannabinoid compounds.

In alternative embodiments, any simulated moving bed (SMB) chromatographic apparatus or equivalent, or any system suitable to perform simulated moving bed chromatography, can be used. The stationary or solid phase may be any material, which the skilled person can choose according to the nature of the mixture and the compounds to be separated. To determine the respective flow rates at the different pumps, several methods and models are known in the prior art which may be implemented in order to achieve an optimal separation of the desired compound(s).

Plant Materials and Plant Extracts

In alternative embodiments, the "plant material" or "plant extracts" comprise or are derived from one or more cannabis or hemp plants, or from other plants. In alternative embodiments, the microbial material or extracts comprise or are derived from yeast, lichen, algae or bacteria. The term "plant material" encompasses a plant or plant part (e.g. bark, wood, leaves, stems, roots, flowers, fruits, seeds, berries or parts thereof) as well as exudates, and includes material falling within the definition of "botanical raw material" in the Guidance for Industry Botanical Drug Products Draft Guidance, August 2000, US Department of Health and Human Services, Food and Drug Administration Centre for Drug Evaluation and Research. The term "cannabis plant(s)" encompasses wild type *Cannabis sativa* and also variants thereof, including *Cannabis* chemovars (varieties characterized by virtue of chemical composition) which naturally contain different amounts of the individual cannabinoids, also *Cannabis sativa* subspecies indica including the variants var. *indica* and var. *kafiristanica, Cannabis indica* and also plants which are the result of genetic crosses, self-crosses or hybrids thereof. The term "*Cannabis* plant material" also can encompass plant material derived from one or more cannabis plants, and can comprise any "cannabis plant material" including, e.g., herbal *Cannabis* and dried *Cannabis* biomass. The term "*Cannabis* plant material" also can encompass "decarboxylated *Cannabis* plant material", which refers to *Cannabis* plant material which has been subject to a decarboxylation step in order to convert cannabinoid acids to the corresponding free cannabinoids. In alternative embodiments, a starting material for a purification process as provided herein is an extract solution containing a cannabinoid or cannabinoid acid obtained from a natural or a synthetic source, e.g., a plant or microbial material. In alternative embodiments, the "extract solution containing a cannabinoid or cannabinoid acid" comprises a solvent extract of a plant or microbial material. Solvents used for extraction for use in the preparation of extract solutions can comprise non-polar solvents, polar solvents such as ethanol, methanol or water, or organic solvents such as liquid carbon dioxide, and combinations thereof. The solvent can be an organic solvent, selected from the group consisting of: non-polar solvents include liquid non-polar solvents comprising lower C1-C12, preferably C3 to C8, straight chain or branched chain alkanes for example, methane, ethane, propane, butane, pentane, toluene, trimethylpentane; a low molecular weight alcohol, polar solvents consisting of for example, ethanol, methanol, water; a low molecular weight chlorinated hydrocarbon, for example, chloroform and dichloromethane; or a supercritical fluid such as $CO_2$ with or without an organic solvent modifier.

In alternative embodiments, the extract is prepared by dissolving or partially dissolving the natural or synthetic, or the plant or microbial material in a solvent, removing insoluble material from the resultant solution (optionally by filtration with or without activated carbon, precipitation, centrifugation and the like), and optionally removing some or all of the extraction solvent from the solution (optionally by rotary evaporation) to form an extract or extract solution or concentrate containing a cannabinoid or cannabinoid acid.

In alternative embodiments, the plant or microbial material or extracts used as a starting material comprise oils or extracts from a trichome or a trichome fraction of a pubescent plant, or an algae or a lichen. The oils or extracts can be "harvested" from the plant or microbial material by: washing, contacting or exposing the trichome or trichome fraction, or the pubescent plant, algae or lichen, with: at least one non-polar, organic solvent; at least one polar, organic solvent; or, a mix of at least one non-polar, organic solvent with (and) at least one polar, organic solvent, and collecting or separating the solvent from the trichome or trichome fraction, or the pubescent plant, algae or lichen, wherein the solvent comprises the oil or extract to be further processed using a method as provided herein. In alternative embodiments, the pubescent plant or plant part, the algae or algae part, or the lichen or lichen part, other than harvesting or collecting, is unprocessed or has not been physically processed, or has not been exposed to: a solvent or aqueous solution; a heating or drying process; a dehydration process; a crushing process; and/or, a chopping, macerating or mincing process, since (after) its harvest, before the trichome or trichome fraction, or the pubescent plant, algae or lichen is washed with, contacted by or exposed to: at least one non-polar, organic solvent; at least one polar, organic solvent; or, a mix of at least one non-polar, organic solvent with (and) at least one polar, organic solvent.

In alternative embodiments, extractions comprise using a technique referred to as accelerated solvent extraction, which can use subcritical water or any combination of water and solvent. In one embodiment, when isolating cannabinoid acids, a modified pH gradient elution solvent is used. The primary purpose of this pH adjustment (the modified pH gradient) is to promote or prevent ionization of the cannabinoid acid. pH modified gradient elution solvents s may be achieved by the additional of a small volume of acid or base to the solvent. It may be sufficient to add a relatively weak acid, such as acetic acid, oxalic acid, glycolic acid, carbonic acid or ammonium hydroxide or a small amount of base or buffering agent such as sodium hydroxide, magnesium hydroxide, sodium carbonate or sodium bicarbonate. For any given purification process the optimal amount and type of acid or base used may be determined empirically. An alternative exemplary acidified solvent is 0.1% acetic acid in ethanol or 0.1% sodium hydroxide in ethanol.

In alternative embodiments, the neutralizing agent consists of for example sodium hydroxide, sodium carbonate, potassium carbonate, and potassium t-amylate, sodium bicarbonate.

Non-Polar and Polar Solvents, Solvent Extractions

Acidified non-polar and polar solvents of the types described above can be useful in preparation of gradient elutions using ion exchange chromatography. The solvents used in the conversion can comprise an organic solvent, e.g., a non-polar solvent, including a liquid non-polar solvent comprising lower C1-C12, or C3 to C8, straight chain or branched chain alkanes for example, methane, ethane, propane, butane, pentane, toluene, trimethylpentane, hexane; a low molecular weight alcohol, polar solvents consisting of for example, ethanol; a low molecular weight chlorinated hydrocarbon, for example, chloroform and dichloromethane; a heterocyclic compound or cyclic ether for example, tetrahydrofuran and 2-methyltetrahydrofuran and aromatic ring hydrocarbons such as benzene, toluene, xylene and ethylbenzene.

In alternative embodiments, the plant material is subjected to a decarboxylation step prior to solvent extraction. The purpose of the decarboxylation step is to convert cannabinoid acids present in the plant or microbial material to the corresponding free cannabinoids. In alternative embodiments, the decarboxylation is carried out by heating the plant or microbial material to a defined temperature for a suitable length of time. Decarboxylation of cannabinoid acids is a function of time and temperature, thus at higher temperatures a shorter period of time will be taken for complete decarboxylation of a given amount of cannabinoid acid. In alternative embodiments selecting appropriate conditions for decarboxylation consideration includes minimizing thermal degradation of the desirable, pharmacological cannabinoids into undesirable degradation products, particularly thermal degradation of $\Delta^9$-THC. In alternative embodiments, the decarboxylation is carried out in a multi-step heating process in which the plant or microbial material is: i) heated to a first temperature for a first (relatively short) time period to evaporate off retained water and allow for uniform heating of the plant or microbial material; and ii) the temperature is increased to a second temperature for a second time period (typically longer than the first time period) until at least 95% conversion of the acid cannabinoids to their neutral form has occurred.

In alternative embodiments, the "extract containing a cannabinoid or a cannabinoid acid" prepared from the starting plant or microbial material comprises a "botanical drug substance" prepared from the plant or microbial material, or a polar or non-polar solvent solution of such a botanical drug substance. In the context of this application a "botanical drug substance" is an extract derived from plant or microbial material, which extract fulfills the definition of "botanical drug substance" provided in the Guidance for Industry Botanical Drug Products Draft Guidance, August 2000, US Department of Health and Human Services, Food and Drug Administration Centre for Drug Evaluation and Research of: "A drug substance derived from one or more plants, algae, or macroscopic fungi. It is prepared from botanical raw materials by one or more of the following processes: pulverization, decoction, expression, aqueous extraction, ethanolic extraction, or other similar processes." "Botanical drug substances" derived from cannabis plants include primary extracts prepared by such processes as, for example, maceration, percolation, and solvent extraction.

In alternative embodiments, solvent extraction may be carried out using essentially any solvent that dissolves, or substantially dissolves, cannabinoids/cannabinoid acids, such as for example C1 to C5 alcohols (e.g. ethanol, methanol), C5-C12 alkanes (e.g. hexane), norflurane (HFA134a), 1,1,1,2,3,3,3-Heptafluoropropane (or HFA227), chloroform, dichloromethane, dichloroethane and carbon dioxide. When solvents such as those listed above are used, the resultant extract typically contains non-specific lipid-soluble material. This can optionally be removed by a variety of processes including filtration to remove solids, "winterization", which involves for example chilling to $-20°$ C. or lower followed by filtration to remove waxy ballast, extraction with liquid carbon dioxide and by distillation.

In alternative embodiments, any protocol for the preparation of botanical drug substances from cannabis and hemp plant material can be used, e.g., as described in International patent application WO 02/064109. In alternative embodiments, the botanical drug substance is obtained by carbon dioxide ($CO_2$) extraction, polar solvent extraction or non-polar solvent extraction or combinations thereof followed by a filtration. Optionally a secondary extraction is performed to remove a substantial proportion of non-cannabinoid materials, e.g. waxes, wax esters and glycerides, unsaturated fatty acid residues, terpenes, carotenes, and flavonoids and other ballast.

In alternative embodiments, if it is intended to prepare free cannabinoids from the cannabis plant or microbial material, then the material is heated to a defined temperature for a defined period of time in order to partially or substantially decarboxylate cannabinoid acids to free cannabinoids prior to extraction of the botanical drug substance. In alternative embodiments, the botanical drug substance is prepared according to a process comprising the following steps: i) optional decarboxylation of the plant or microbial material, ii) extraction with polar or non-polar solvent, to produce a crude botanical drug substance, iii) optional precipitation with C1-C5 alcohol to reduce the proportion of non-target materials, iv) removing the precipitate (optionally by filtration), v) optional treatment with activated charcoal, and vi) evaporation to remove C1-C5 alcohol and water, thereby producing a final botanical drug substance.

In alternative embodiments, provided are methods for converting cannabidiol (CBD), including substantially purified cannabidiol (CBD), to Δ8-tetrahydrocannabinol (Δ8-THC) and/or Δ9-tetrahydrocannabinol (Δ9-THC). As will be appreciated by one knowledgeable in the art and as discussed below, the reaction times may be varied somewhat, producing product at different yields and purities.

Furthermore, functional equivalents may be substituted where appropriate.

In alternative embodiments, an exemplary method of converting CBD to Δ8-tetrahydrocannabinol (Δ8-THC) and/or Δ9-tetrahydrocannabinol (Δ9-THC) comprises:

providing a reaction mixture comprising a Lewis acid and/or a non-oxidizing acid catalyst in a reaction solvent, adding a CBD, Δ8-tetrahydrocannabinol (Δ8-THC) and/or Δ9-tetrahydrocannabinol (Δ8-THC), and/or a substantially pure CBD and/or Δ8-THC and/or Δ9-THC, to the reaction mixture, and then mixing or reacting the reaction mixture, optionally for between about 1 minute (m) to about 10 hours (h);

adding a neutralizing agent to the mixed or reacted mixture, optionally after the mixing or reacting is complete;

filtering (filtration of) the catalyst and the neutralizing agent from the reaction mixture, optionally allowing reaction mixture to separate into an aqueous and an organic phase, optionally removing the reaction solvent, optionally dissolving or mixing the organic phase in a second solvent;

adding the mixed or reacted mixture onto (or loading into) at least one chromatography column, and if the reaction mixture is separated into an aqueous and an organic phase, adding or loading the organic phase to the at least one chromatography column, wherein optionally the organic phase has been dissolved or mixed into the second solvent, and eluting the CBD, Δ8-tetrahydrocannabinol (Δ8-THC) and/or Δ9-tetrahydrocannabinol (Δ8-THC), and/or a substantially pure CBD and/or Δ8-THC and/or Δ9-THC off the at least one chromatography column.

In one embodiment, the mixture is allowed to separate into an aqueous phase and an organic phase; and optionally the process further comprises removing or separating (optionally removing or separating by decanting) the organic phase and/or (from) the aqueous phase.

In alternative embodiments, the reaction solvent is removed, or molecules or reaction products dissolved in an organic liquid are removed, by a process comprising use of selective membranes to separate molecules or solvent, e.g., comprising use of a molecular scale separation in an aqueous solution using a membrane, reverse osmosis and/or nanofiltration, e.g., for the separation of solvents, ions and other molecules, e.g., as described in U.S. patent application publication U.S. Pat. No. 9,309,483. In alternative embodiments, selective membranes used in membrane separations as used with methods as provided herein comprise polymeric membranes, ceramic membranes and mixed polymeric/inorganic membranes.

In alternative embodiments, a polymeric or ceramic material used in a selective membrane used in a process as provided herein comprises use of a separating layer capable of separating the solvent from the reaction mixture products.

In alternative embodiments, a selective membrane as used in methods as provided herein is formed from or comprises a polymeric materials suitable for fabricating microfiltration, ultrafiltration, nanofiltration, or reverse osmosis membranes, including for example, polyethylene, polypropylene, polytetrafluoroethylene (PTFE), polyvinylidene difluoride (PVDF), polysulfone, polyethersulfone, polyacrylonitrile, polyamide, polyimide, polyamideimide, polyetherimide, cellulose acetate, polyaniline, polypyrrole, polyetheretherketone (PEEK), polybenzimidazole, and mixtures thereof. In alternative embodiments, the selective membrane is made by any technique known to the art, including sintering, stretching, track etching, template leaching, interfacial polymerization, or phase inversion. In at least one embodiment, the at least one selective membrane may be crosslinked or treated so as to improve its stability in the process solvents.

In alternative embodiments, a selective membrane as used in methods as provided herein comprises a composite material comprising a support and a thin, non-porous, selectively permeable layer. The thin, non-porous, selectively permeable layer may, for example, be formed from or comprise a material chosen from modified polysiloxane based elastomers including polydimethylsiloxane (PDMS) based elastomers, ethylene-propylene diene (EPDM) based elastomers, polynorbornene based elastomers, polyoctenamer based elastomers, polyurethane based elastomers, butadiene and nitrile butadiene rubber based elastomers, natural rubber, butyl rubber based elastomers, polychloroprene (e.g., NEOPRENE™) based elastomers, epichlorohydrin elastomers, polyacrylate elastomers, polyethylene, polypropylene, polytetrafluoroethylene (PTFE), polyvinylidene difluoride (PVDF) based elastomers, polyetherblock amides (PEBAX), polyurethane elastomers, crosslinked polyether, polyamide, polyaniline, polypyrrole, and mixtures thereof.

In another embodiment, a selective membrane as used in methods as provided herein is prepared from an inorganic material such as, for example, silicon carbide, silicon oxide, zirconium oxide, titanium oxide, and zeolites, using any technique known to those skilled in the art such as sintering, leaching, or sol-gel processing.

In a further embodiment, a selective membrane as used in methods as provided herein comprises a polymer membrane with dispersed organic or inorganic matrices in the form of powdered solids present at amounts up to about 20 wt % of the polymer membrane. In another embodiment, a selective membrane as used in methods as provided herein uses carbon molecular sieve matrices, which can be prepared by pyrolysis of any suitable material as described in U.S. Pat. No. 6,585,802. Zeolites as described in U.S. Pat. No. 6,755,900 may also be used as an inorganic matrix. Metal oxides, for example, titanium dioxide, zinc oxide, and silicon dioxide may be used, such as the materials available from Evonik Industries AG (Germany), e.g., AEROSIL™ and ADNANO™. Mixed metal oxides such as mixtures of cerium, zirconium, and magnesium oxides may also be used. In at least one embodiment, the matrices will be particles less than about 1.0 micron in diameter, for example less than about 0.1 microns in diameter, such as less than about 0.01 microns in diameter.

In at least one embodiment, the at least one selective membrane comprises two membranes. In another embodiment, the at least one selective membrane comprises three membranes.

In another embodiment, a selective membrane as used in methods as provided herein comprises a nanofiltration membrane, for example, comprising a membrane filtration which separates particles having molar masses ranging from about 150 to about 1,500 Da. In at least one embodiment, the pressure ranges from about 0.5 MPa to about 7 MPa.

In another embodiment, a selective membrane as used in methods as provided herein has a molecular weight cut-off ranging from about 150 g/mol to about 1,500 g/mol (a molecular weight cut-off is defined according to the methodology of See-Toh et al (2007) (Journal of Membrane Science, 291 (1-2), pp. 120-125), where the molecular weight cut-off is taken to be the molecular weight at which 90% rejection is achieved of a series of styrene oligomers. In one embodiment, the at least one selective membrane has a molecular weight cut-off ranging from about 200 g/mol to about 700 g/mol, particularly preferred 300-600 g/mol.

In another embodiment, a selective membrane as used in methods as provided herein comprises a hydrophobic membrane, for example, a selective membrane that provides a contact angle for water of more than 70° C. at 25° C., as measured using the static sessile drop method described in ASTM D7334; and optionally selective membranes have a contact angle for water of more than 70° C. at 25° C., or, have a contact angle for water of more than 90° C. at 25° C.

In another embodiment, a selective membrane as used in methods as provided herein comprises a polyimide membrane, for example, a membrane made of P84 (CAS No. 9046-51-9) and P84HT (CAS No. 134119-41-8) and/or mixtures thereof. The polyimide membranes optionally may be crosslinked according to GB2437519. In another embodiment, a selective membrane as used in methods as provided herein comprises an organic coated polyimide membrane, for example, comprising membrane crosslinked or non-crosslinked P84 and/or P84HT membranes, and the crosslinked or non-crosslinked, coated polyimide membranes, e.g., P84 and/P84HT membranes and/or mixtures thereof, comprise a coating e.g., comprising a silicone acrylate such as a silicone acrylate to coat the membranes as described in U.S. Pat. Nos. 6,368,382, 5,733,663, JP 62-136212, P 59-225705, DE102009047351 and in EP 1741481 Δ1. n another embodiment, a selective membrane as used in methods as provided herein comprises a polyimide comprising a silicone acrylate as described in DE102009047351 and in EP 1741481 Δ1.

In alternative embodiments, the tetrahydrocannabinol (THC), CBD, (Δ8-THC) and/or Δ9-tetrahydrocannabinol (Δ9-THC), is combined with suitable excipients or diluents (e.g., pharmaceutically acceptable excipients or diluents, such as saline, buffered saline or water, optionally in sterile form) known in the art, thereby forming or formulating a pharmaceutical composition.

In alternative embodiments, the reaction product, e.g., the tetrahydrocannabinol (THC), CBD, (Δ8-THC) and/or Δ9-tetrahydrocannabinol (Δ9-THC), e.g., at therapeutically effective concentrations or dosages, is combined with or is formulated with a pharmaceutically or pharmacologically acceptable carrier, excipient or diluent, either biodegradable or non-biodegradable. Exemplary examples of carriers include, but are by no means limited to, for example, poly(ethylene-vinyl acetate), copolymers of lactic acid and glycolic acid, poly(lactic acid), gelatin, collagen matrices, polysaccharides, poly(D,L lactide), poly(malic acid), poly (caprolactone), celluloses, albumin, starch, casein, dextran, polyesters, ethanol, methacrylate, polyurethane, polyethylene, vinyl polymers, glycols, mixtures thereof and the like. Standard excipients that can be used include gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxyethyl cellulose, hydroxypropylcellulose, hydroxypropylmethycellulose phthalate, non-crystalline cellulose, magnesium aluminum silicate, triethanolamine, polyvinyl alcohol, polyvinylpyrrolidone, sugars and starches. See, for example, Remington: The Science and Practice of Pharmacy, 1995, Gennaro ed.

In some embodiments, the catalyst is a Lewis acid, for example, p-toluenesulfonic acid, boron trifluoride or $BF_3Et_2O$. In some embodiments, the $BF_3Et_2O$ (boron trifluoride diethyl etherate) is in dry methylene chloride, ethyl acetate, ethanol, hexane or other organic solvent. In yet other examples, the catalyst may be hydrochloric acid in ethanol or sulfuric acid in cyclohexane.

In some embodiments, the catalyst is a non-oxidizing acid, for example, formic acid, acetic acid or hydrobromic acid. In some embodiments, the non-oxidizing acid is in dry methylene chloride, ethyl acetate, ethanol, hexane or other organic solvent.

In some embodiments, a base is added to the reaction mixture prior to optionally allowing the reaction mixture to separate into organic and aqueous phases. The base may be an alkali metal hydrogen carbonate, carbonate of an alkali metal, lithium hydroxide (LiOH), sodium hydroxide (NaOH), potassium hydroxide (KOH), rubidium hydroxide (RbOH), cesium hydroxide (CsOH), magnesium hydroxide (Mg(OH)), calcium hydroxide (Ca(OH)), strontium hydroxide (Sr(OH)), barium hydroxide (Ba(OH)).

In some embodiments, the organic layer is dried prior to eluting. In these embodiments, a suitable drying or dehydration agent, for example, $MgSO4$ or $Na_2SO_4$ is used.

In yet other embodiments, the process may be carried out under an inert atmosphere such as a nitrogen (e.g., $N_2$) atmosphere.

In alternative embodiments, and as discussed below, yield is determined by looking at the peak area for the isolated compound in the gas chromatography-mass spectra analysis of the crude reaction product mixture and the final reaction product mixture. It is important to note that in the prior art, yield is often calculated on the basis of first isolated crude product before final purification. In some embodiments of processes provided herein yield of Δ8-THC and Δ9-THC is at least about 75%; in other embodiments, the yield of Δ8-THC and Δ9-THC is at least about 90%; and in other embodiments, yield of Δ8-THC and Δ9-THC is at least about 98%; and in yet other embodiments, yield of Δ8-THC and Δ9-THC is between about 75 to 98% or 99%.

In alternative embodiments, purity is determined by Gas Chromatography-Mass Spectrometry (GC-MS) and/or by analytical high-performance liquid chromatography (HPLC). The total ion chromatogram from the GC-MS gives information similar to that provided by a flame ionization detector (FID)-GC in that the peak area is proportional to the mass of the analytes detected. Total peak area and the peak areas of the individual analytes can be compared in the GC-MS case as long as the masses are in generally the same range. As discussed below, in some embodiments, purity of the Δ8-THC and Δ9-THC mixture isolated by the process is greater than about 90%, 95%, 97% or 98%, or purity is greater that about 98% to 99%.

Chapter II

In alternative embodiments, provided are continuous isolation and purification processes for preparing a substantially pure cannabidiol or a product enriched in cannabidiol from synthetic or natural sources, e.g., from plant or microbial material or microbial extracts. In alternative embodiments, provided herein are improved methods for converting cannabidiol (CBD) to $Δ^9$-THC, including a purification and conversion process based on a simple combination of continuous chromatographic gradient elutions and semi continuous isomerization reactions. This exemplary process is simple, efficient and economic.

In alternative embodiments, provided are methods of preparing cannabinoids in substantially pure form starting from plant extract material and conversion of the purified CBD to form both $Δ^8$ THC and $Δ^9$ THC and subsequent conversion of the formed $Δ^8$ tetrahydrocannabinol into $Δ^9$ tetrahydrocannabinol.

In alternative embodiments, provided are processes for producing and isolating cannabinoids from cannabis and hemp extracts which contain cannabinoids in minute amounts. In alternative embodiments, provided are processes for producing and isolating cannabinoids from natural materials, including plant or plant extracts, microbes, or botanical drug substances, or synthetically and semi-synthetically prepared cannabinoid products, or from recombinantly engineered microbes, e.g., yeasts or bacteria recombinantly engineered to express one or more cannabinoids. In one embodiment, exemplary methods are inexpensive and provide specific cannabinoid concentrates (e.g., of CBD, $Δ^8$-THC, $Δ^9$-THC) of high purity.

In one embodiment, exemplary methods provide a simple and economical continuous process for separating and concentrating cannabinoids from solvent-extracted cannabinoid containing materials. In one embodiment, exemplary methods provide a method that first converts the substantially isolated CBD into a mixture of $\Delta^8$-THC and $\Delta^9$-THC, and then subsequently converts the $\Delta^8$-THC into $\Delta^9$-THC. In alternative embodiments, the solvent-extracted cannabinoid containing materials are derived from synthetic or biological materials such as hemp and *Cannabis* or botanical drug substances, or from microbial materials; and the solvent extraction methods can be polar solvent extractions, nonpolar solvent extractions, or the solvent extraction methods can comprise use of super critical carbon dioxide or mixtures thereof. The solvent extraction methods can extract cannabinoids substantially from the synthetic or biological, e.g., plant, matter, along with other plant matter comprising lipids, waxes, monoterpenes, sesquiterpenes, hydrocarbons, alkaloids, flavonoids and chlorophylls.

In alternative embodiments, methods provided herein comprise subjecting cannabinoid containing solvent extract starting materials to a number of chromatographic resins in various contacting steps using various gradient elution solvents s.

In alternative embodiments, the cannabinoids which can be fractionated and isolated using methods as provided herein, or which can be produced in reactions as provided herein, or from which the solvent extracts are derived can be from, or can comprise: $\Delta^9$tetrahydrocannabinol ($\Delta^9$ THC); cannabidiol (CBD); cannabinol (CBN); cannabigerol (CBG); cannabichromene (CBC); cannabidivarol (CBDV); tetrahydrocannabidiol (THCBD); tetrahydrocannabigerol (THCBG); tetrahydrocannabichromene (THCBC); tetrahydrocannabidivarol (THCBDV), or combinations thereof, including carboxylic acid precursors of the foregoing compounds and related naturally occurring compounds and their derivatives.

In alternative embodiments, provides are methods of preparing or obtaining a substantially pure cannabinoid or a product enriched in a given cannabinoid comprising:
  (i) obtaining an extract or extract solution comprising or containing a cannabinoid or a cannabinoid acid from a natural or a synthetic source, e.g., a plant or microbial material;
  (ii) filtering the extract or extract solution of step (i) to remove solids and color bodies;
  (iii) removing the extract solvent (as an extract fraction);
  (v) continuously loading of an amount of extract solution over a defined time increment over multiple stationary phase resins columns such as a normal phase, reverse phase and/or ion exchange chromatographic resin;
  (vi) continuously eluting the extract solution using multiple defined gradient elution solvents s at specific time increments and volumes;
  (vii) continuously collecting the gradient elution fractions;
  (viii) removing the gradient elution solvent from the produced fractions to generate a substantially purified extract
  (ix) optionally loading of specific first gradient elution fractions on a reverse phase, ion exchange or normal chromatographic resin;
  (x) continuously eluting the first gradient elution fractions with a second gradient elution solvent; and,
  (xi) removing of the second gradient elution solvent from the produced fractions to produce a purified extract.
In alternative embodiments, the methods further comprise:
  a step (xii): loading of first and second gradient elution solvents s onto an ion exchange chromatographic resin;
  a step (xiii): eluting an extract solution from the ion exchange chromatographic resin of step (xi) using a gradient solvent and collecting the gradient elution fractions; and
  (xiv) removing the gradient elution solvent from the produced fractions of step (xiii) to produce purified and substantially purified extract.

In alternative embodiments, provided are methods of converting CBD to $\Delta^8$ THC and $\Delta^9$ THC comprising:
  (a) providing a reaction mixture comprising a catalyst in an organic solvent;
  (b) adding CBD material from steps (viii) and steps (xiii), above;
  (c) mixing said reaction mixture;
  (d) allowing the mixture to separate into an aqueous phase and an organic phase;
  optionally adding a second solvent; and
  (e) removing the organic phase; and,
  optionally, repeating steps (a) through (e).

In alternative embodiments, provided are methods for purifying $\Delta^8$-THC and $\Delta^9$-THC comprising:
  (a) providing a reaction mixture comprising a stabilizing agent in an organic solvent;
  (b) adding $\Delta^8$-THC and $\Delta^9$-THC to the reaction mixture;
  (c) mixing said reaction mixture to form 9-chlorohexahydrocannabinol;
  (d) combining said reaction mixture with a second organic solvent;
  (e) adding an elimination catalyst or reagent to the reaction mixture to cause an elimination refluxing said reaction mixture under an inert atmosphere;
  (f) pouring the mixture into cold water;
  (g) mixing the mixture;
  (h) allowing the mixture to separate into an aqueous phase and an organic phase;
  optionally adding a second solvent;
  (i) removing the organic phase, which comprises a purified, or a substantially pure, $\Delta^8$-THC and $\Delta^9$-THC; and
  optionally, repeating steps (a) through (i).

In alternative embodiments, provided are methods for converting CBD to substantially pure $\Delta^9$THC comprising:
  (a) providing a reaction mixture comprising a CBD in an organic solvent;
  (b) adding a catalyst to the reaction mixture under a nitrogen atmosphere;
  (c) stirring the reaction mixture;
  (d) adding $NaHCO_3$ or equivalent to the reaction mixture;
  (e) allowing the mixture to separate into an aqueous phase and an organic phase;
  optionally adding a second solvent;
  (f) removing the organic phase, which comprises the converted $\Delta^9$-THC; and
  optionally repeating steps (a) through (f).

In alternative embodiments, a "substantially pure" preparation of cannabinoid is defined as a preparation having a chromatographic purity (of the desired cannabinoid or cannabinoid acid) of greater than about 75%, or greater than about 96%, or greater than about 97%, or greater than about 98%, or greater than about 99%, or greater than about 99.5%, or between about 70% and 99.9%, as determined by area normalisation of an HPLC profile.

In alternative embodiments, the term "product enriched in a given cannabinoid" encompasses preparations having at least about 50%, or greater than about 75%, or greater than about 90%, 95% or 98%, or between about 50% and 99.9%, chromatographic purity, for the desired cannabinoid.

In alternative embodiments, a non-purified, or non-substantially purified, product can comprise a greater proportion of impurities, non-target materials and/or other cannabinoids than a "substantially pure" preparation. The cannabinoid can be (e.g., a cannabinoid purified or isolated by, or made by a reaction of, a method as provided herein can be): $\Delta^9$tetrahydrocannabinol ($\Delta^9$ THC); cannabidiol (CBD); cannabinol (CBN); cannabigerol (CBG); cannabichromene (CBC); cannabidivarol (CBDV); tetra-hydrocannabidiol (THCBD); tetra-hydrocannabigerol (THCBG); tetra-hydrocannabichromene (THCBC); or, tetra-hydrocannabidivarol (THCBDV); the carboxylic acid precursors of the foregoing compounds; and related naturally occurring compounds and their derivatives.

In alternative embodiments, the term "cannabinoids" e.g., a cannabinoid purified or isolated by, or made by a reaction of a process as provided herein, includes or refers to a family of natural products that can contain a 1,1'-di-methyl-pyrane ring, a variedly derivatized aromatic ring and/or a variedly unsaturated cyclohexyl ring and their immediate chemical precursors.

In alternative embodiments, the term "cannflavins", e.g., a cannflavin purified or isolated by, or made by a reaction of a process as provided herein, includes or refers to a family of natural products that can contain a 1,4-pyrone ring fused to a variedly derivatized aromatic ring and linked to a second variedly derivatized aromatic ring.

In alternative embodiments, the term "Lewis acid" refers to a powerful electron pair acceptor; and examples include but are by no means limited to $BF_3Et_2O$ (boron trifluoride ditheyl etherate), p-toluenesulfonic acid and boron trifluoride.

In alternative embodiments, the term "non-oxidizing acid" refers to hydrobromic, hydrochloric, hydrofluoric, acetic, benzoic, chloroacetic, formic, phosphoric, sulfuric, trifluroacetic and oxalic acids.

In alternative embodiments, the term "stabilizing agent" refers to a zinc chloride, hydrogen chloride, methylene chloride, simonkolleite, and mixtures thereof; and examples include but are by no means limited to zinc chloride, hydrogen chloride, and simonkolleite, and polymorphs and hydrates thereof.

In alternative embodiments, the term "essential oils", e.g., an essential oil used as a starting material in a process as provided herein, or an essential oil that may be isolated by a process as provided herein, includes or refers to a family of natural products that can contain a multiple of the 5-membered isoprene unit variedly substituted, often cyclized to form one or more ring systems; they may also contain series of aldehydes and/or ketones and esters of a variety of carboxylic acid substituted compounds.

In alternative embodiments, provided are methods for extracting and/or purifying cannabinoids from any plant material extract known to contain such cannabinoids, cannflavins and essential oils; and, optionally to purify cannflavins and to optionally purify essential oils. In alternative embodiments, the extract is passed through a series of chromatographic columns, for example, a normal phase column, a reversed phase column or an ion exchange column as a continuous simulated moving bed (SMB) configuration.

In one embodiment, the chromatographic column is arranged for gradient elution fractioning using normal phase, reverse phase and/or ion exchange chromatography. In one embodiment $\Delta^9$-THC and CBD are fractionated out of the eluent. For example, in one embodiment, as the extract is passed over the column, $\Delta^9$-THC and CBD is differentially retained or detained (e.g., reversibly bound) on the column. As a result, as the extract comes off the column, the initial fractions eluted off the column will be (substan-tially) free of $\Delta^9$-THC and CBD. The fractions free of $\Delta^9$-THC and CBD are pooled, thereby producing an extract with $\Delta^9$-THC and CBD substantially removed (e.g., in alternative embodiments, "substantially removed" or "substantially fractionated" means at least 85%, 90%, 95%, 98%, 99% or 99.5% or more removed or fractionated).

In one embodiment, the chromatographic column is arranged for gradient elution fractioning using normal phase, reverse phase and/or ion exchange chromatography. In one embodiment $\Delta^9$-THC and CBD are differentially fractionated out of the eluent. For example, in one embodiment, as the extract is passed over the column, $\Delta^9$-THC and CBD are differentially retained or detained (e.g., reversibly bound) on the column. As a result, as the extract comes off the column, the initial fractions eluted off the column will be (substantially) free of $\Delta^9$-THC. The fractions free of $\Delta^9$-THC are pooled, thereby producing an extract with $\Delta^9$-THC substantially removed (e.g., in alternative embodiments, "substantially removed" or "substantially fractionated" means at least 85%, 90%, 95%, 98%, 99% or 99.5% or more removed or fractionated). As the extract progresses, the following fractions eluted off the column will be substantially free of CBD. The fractions free of CBD are pooled, thereby producing an extract with CBD removed (e.g., in alternative embodiments, "substantially removed" or "substantially fractionated" means at least 85%, 90%, 95%, 98%, 99% or 99.5% or more removed or fractionated).

In one embodiment, the chromatographic column is arranged for isocratic elution, simulated moving bed (SMB), fractioning using normal phase, reverse phase and/or ion exchange chromatography. In one embodiment $\Delta^9$-THC and CBD are differentially fractionated out of the eluent. For example, in one embodiment, as the extract is passed over the column, $\Delta^9$-THC and CBD are differentially retained or detained (e.g., reversibly bound) on the column. As a result, as the extract comes off the column, the initial fractions eluted off the column will be (substantially) free of $\Delta^9$-THC. The fractions free of $\Delta^9$-THC are pooled, thereby producing an extract with $\Delta^9$-THC substantially removed (e.g., in alternative embodiments, "substantially removed" or "substantially fractionated" means at least 85%, 90%, 95%, 98%, 99% or 99.5% or more removed or fractionated). As the extract progresses, the following fractions eluted off the column will be substantially free of CBD. The fractions free of CBD are pooled, thereby producing an extract with CBD removed (e.g., in alternative embodiments, "substantially removed" or "substantially fractionated" means at least 85%, 90%, 95%, 98%, 99% or 99.5% or more removed or fractionated).

In some embodiments, (substantially) only $\Delta^9$-THC is substantially fractionated out of the eluent. For example, in one embodiment, as the extract or pooled fractions from a previous normal phase, reverse phase and/or ion exchange elution are passed over the column, $\Delta^9$-THC is differentially retained or detained (e.g., reversibly bound) on the column. As a result, as the extracts are pooled previous elution fractions comes off the column, the initial fractions eluted off the column will be free of $\Delta^9$-THC. These fractions free of $\Delta^9$-THC are pooled, thereby producing an extract with $\Delta^9$-THC substantially removed (e.g., in alternative embodiments, "substantially removed" or "substantially fractionated" means at least 85%, 90%, 95%, 98%, 99% or 99.5% or more removed or fractionated).

In some embodiments, when using a continuous chromatography apparatus or device, a series of columns are arranged (for example, at least 2, 3, 4, 5, 6, 7 or 8 or more, or between 3 and 30, columns are arranged) in a continuous rotation traveling through a series of contact points where gradient elution solvents s and extract solutions are introduced at fixed points for a period of time allowing for continuous loading and elution, and collection of fractions. The first column is loaded with extract solution at the first position (or station). The first column is then moved to the second position where the first gradient elution solvent is introduced (or loaded) while at the same time a second column is loaded with extract solution at position one. The first column then rotates (i.e., is moved) to the third position where the second gradient solvent is introduced, the second column moves to the second position where the first gradient solvent is introduced and a third column is loaded with extract solution at position one. The first column then moves to the fourth position where the third gradient solvent is introduced, the second column moves to the third position where the second gradient solvent is introduced, the third column moves to the second position where the first gradient solvent is introduced and the fourth column is loaded with extract solution at position one. The first column then moves to the fifth position where the fourth gradient solvent is introduced, the second column moves to the fourth position where the third gradient solvent is introduced, the third column moves to the third position where the second gradient solvent is introduced, the fourth column moves to the second position where the first gradient solvent is introduced and the fifth column is loaded with extract solution at position one. The first column then moves to the sixth position where the fifth gradient solvent solution is introduced, the second column moves to the fifth position where the fourth gradient solvent is introduced, the third column moves to the fourth position where the third gradient solvent is introduced, the fourth column moves to the third position where the second gradient solvent is introduced, the fifth column moves to the second position where the first gradient solvent is introduced and the sixth column is loaded with extract solution at position one. The first column then moves or returns to the first position where extract solution is loaded, the second column moves to the sixth position where the fifth gradient solvent introduced, the third column moves to the fifth position where the fourth gradient solvent is introduced, the fourth column moves to the fourth position where the third gradient solvent is introduced, the fifth column moves to the third position where the second gradient solvent is introduced and the sixth column moves to the second position where the first gradient solvent is introduced.

In an alternative embodiment, the first gradient solvent elutes CBD, CBG and CBN and is substantially fractionated in the eluent. For example, in one embodiment, as the extract or pooled fractions from a normal phase, reverse phase and/or ion exchange elution are passed over the column, CBD, CBG and CBN is differentially produced in the eluent (e.g., by use of a gradient elution process). In a particular embodiment second gradient solvent elutes CBD and is substantially fractionated in the eluent. For example, in one embodiment, as the extract or pooled fractions from a normal phase, reverse phase and/or ion exchange elution are passed over the column, CBD is differentially produced in the eluent. In a particular embodiment the third gradient solvent elutes CBD and $\Delta^9$-THC and is substantially fractionated in the eluent. For example, in one embodiment, as the extract or pooled fractions from a normal phase, reverse phase and/or ion exchange elution are passed over the column, CBD and $\Delta^9$-THC is differentially produced in the eluent. In a particular embodiment the fourth gradient elutes $\Delta^9$-THC and is substantially fractionated in the eluent. For example, in one embodiment, as the extract or pooled fractions from a normal phase, reverse phase and/or ion exchange elution are passed over the column, $\Delta^9$-THC is differentially produced in the eluent. In a particular embodiment the fifth gradient elutes CBC, THC-A, terpenes and $\Delta^9$-THC and is substantially fractionated in the eluent. For example, in one embodiment, as the extract or pooled fractions from a normal phase, reverse phase and/or ion exchange elution are passed over the column, CBC, THC-A, terpenes and $\Delta^9$-THC is differentially produced in the eluent.

In some embodiments, when using a continuous chromatography apparatus or device, a series of columns are arranged, for example 3, 4, 5, 6, 7, 8 or more, or between 3 and 30 or more, columns or more are arranged in a continuous rotation traveling through a series of contact points where gradient elution solvents s and extract solutions are introduced at fixed points for a period of time allowing for continuous loading and elution, and collection of fractions. The first column is loaded with extract solution at the first position (or station). The first column is then moved to the second position where the first gradient elution solvent is introduced (or loaded) while at the same time the second column is loaded with extract solution at position one. The first column then rotates (i.e., is moved) to the third position where the second gradient solvent is introduced, the second column moves to the second position where the first gradient solvent is introduced and the third column is loaded with extract solution at position one. The first column then moves to the fourth position where the third gradient solvent is introduced, the second column moves to the third position where the second gradient solvent is introduced, the third column moves to the second position where the first gradient solvent is introduced and the fourth column is loaded with extract solution at position one. The first column then moves to the fifth position where the fourth gradient solvent i is introduced, the second column moves to the fourth position where the third gradient solvent is introduced, the third column moves to the third position where the second gradient solvent is introduced, the fourth column moves to the second position where the first gradient solvent is introduced and the fifth column is loaded with extract solution at position one. The first column then moves to the sixth position where the fifth gradient solvent is introduced, the second column moves to the fifth position where the fourth gradient solvent is introduced, the third column moves to the fourth position where the third gradient solvent is introduced, the fourth column moves to the third position where the second gradient solvent is introduced, the fifth column moves to the second position where the first gradient solvent is introduced and the sixth column is loaded with extract solution at position one. The first column then moves or returns to the first position where extract solution is loaded, the second column moves to the sixth position where the fifth gradient solvent is introduced, the third column moves to the fifth position where the fourth gradient solvent solution is introduced, the fourth column moves to the fourth position where the third gradient solvent is introduced, the fifth column moves to the third position where the second gradient solvent is introduced and the sixth column moves to the second position where the first gradient solvent is introduced. The equipment is generally described in U.S. Pat. Nos. 4,764,276, 4,808,317, and 4,710,364, for example, each of which are incorporated herein by reference.

In a particular embodiment the first gradient solvent elutes CBD, CBG and CBN and is substantially fractionated in the eluent. For example, in one embodiment, as the extract or pooled fractions from a normal phase, reverse phase and/or ion exchange elution are passed over the column, CBD, CBG and CBN is differentially produced in the eluent (e.g., by use of a gradient elution process). In a particular embodiment second gradient solvent elutes CBD and is substantially fractionated in the eluent. For example, in one embodiment, as the extract or pooled fractions from a normal phase, reverse phase and/or ion exchange elution are passed over the column, CBD is differentially produced in the eluent. In a particular embodiment the third gradient solvent elutes CBD and $\Delta^9$-THC and is substantially fractionated in the eluent. For example, in one embodiment, as the extract or pooled fractions from a normal phase, reverse phase and/or ion exchange elution are passed over the column, CBD and $\Delta^9$-THC is differentially produced in the eluent. In a particular embodiment the fourth gradient solvent elutes $\Delta^9$-THC and is substantially fractionated in the eluent. For example, in one embodiment, as the extract or pooled fractions from a normal phase, reverse phase and/or ion exchange elution are passed over the column, $\Delta^9$-THC is differentially produced in the eluent. In a particular embodiment the fifth gradient solvent elutes CBC, THC-A, terpenes and $\Delta^9$-THC and is substantially fractionated in the eluent. For example, in one embodiment, as the extract or pooled fractions from a normal phase, reverse phase and/or ion exchange elution are passed over the column, CBC, THC-A, terpenes and $\Delta^9$-THC is differentially produced in the eluent. The second gradient solvent containing CBD is combined with a Lewis acid or non-oxidizing acid catalyst, optionally additional CBD or substantially pure CBD and/or ($\Delta$8-THC) and/or $\Delta$9-tetrahydrocannabinol ($\Delta$9-THC) can be added to the reaction mixture, mixing said reaction mixture for a period of time; adding a neutralizing agent to said mixture; filtration of catalyst and neutralizing agent from mixture; optionally allowing mixture to separate into an aqueous and organic phase; optionally dissolving organic phase in a second solvent; adding a stabilizing agent; mixing said reaction mixture for a period of time; adding a elimination catalyst or reagent to said reaction mixture; filtration of stabilizing agent and elimination agent from mixture; optionally allowing mixture to separate into an aqueous phase and an organic phase; optionally adding a further solvent; adding organic phase to a chromatography column and eluting the tetrahydrocannabinol from the organic phase. The tetrahydrocannabinol may then be combined with suitable excipients known in the art, thereby forming a pharmaceutical composition. In one embodiment, the mixture is allowed to separate into an aqueous phase and an organic phase; and optionally the process further comprises removing the organic phase).

In some embodiments, (substantially) only CBD is substantially fractionated out of the eluent. For example, in one embodiment, as the extract or pooled fractions from a previous normal phase, reverse phase and/or ion exchange elution are passed over the column, CBD is differentially retained or detained (e.g., reversibly bound) on the column. As a result, as the extract or pooled previous elution fractions comes off the column, the initial fractions eluted off the column will be (substantially) free of CBD. These fractions free of CBD are pooled, thereby producing an extract with CBD substantially removed (e.g., in alternative embodiments, "substantially removed" or "substantially fractionated" means at least 85%, 90%, 95%, 98%, 99% or 99.5% or more removed or fractionated).

In some embodiments, $\Delta^9$-THC carboxylic acid species or $\Delta^9$-THCA and CBD carboxylic acid species CBDA are fractionated out of out of the eluent. For example, in one embodiment, as the extract or pooled fractions from a first elution are passed over the column, $\Delta^9$-THCA and CBDA are differentially retained or detained (e.g., reversibly bound) on the column. As a result, as the extract or pooled first elution fractions comes off the column, the initial fractions eluted off the column will be (substantially) free of $\Delta^9$-THCA and CBDA. These fractions (substantially) free of $\Delta^9$-THCA and CBDA are pooled, thereby producing an extract with $\Delta^9$-THCA and CBDA substantially removed (e.g., in alternative embodiments, "substantially removed" or "substantially fractionated" means at least 85%, 90%, 95%, 98%, 99% or 99.5% or more removed or fractionated).

In some embodiments, the $\Delta^9$-THC may be eluted from the column, extracted or concentrated, for purifying, or substantially purifying, $\Delta^9$-THC. In alternative embodiments, the chromatographic column is arranged for fractionating (e.g., sequentially fractionating) a specific cannabinoid or groups of cannabinoids or their carboxylic acid species, cannflavin or essential oil or class of cannabinoids, cannflavins or essential oils out of the eluent, for example, cannabidiol (CBD), cannabinol (CBN), cannabigerol (CBG), cannabichromene (CBC), cannabidivarol (CBDV), tetrahydrocannabidiol (THCBD), tetrahydrocannabigerol (THCBG), tetrahydrocannabichromene (THCBC), tetrahydrocannabidivarol (THCBDV), $\Delta^8$-THC, the carboxylic acid precursors of the foregoing compounds, and related naturally occurring compounds and their derivatives. In alternate embodiments, the chromatographic column is arranged for fractionating (e.g., sequentially fractionating) cannflavins and related naturally occurring compounds and their derivatives. In alternate embodiments, the system is arranged to fractionate the components of essential oils. The list of compounds provided herein is not exhaustive and is in no way intended to be limiting. In these embodiments, the compound(s) of interest are retained or detained (e.g., reversibly bound) on the column so that fractions (alternatively, the last fractions) of the extract eluted from the column contain the compounds(s) of interest. In alternative embodiments, fractions containing the compound(s) of interest are pooled. In some embodiments, different compounds may be extracted with different solvents and then combined into a single extract. As will be appreciated by one knowledgeable in the art, in this manner, several different cannabinoids could be purified from a single extract.

In alternative embodiments, the "plant or microbial material" will be derived from one or more cannabis or hemp plants, or from other plants, or microbes such as lichen, yeast, algae or bacteria. The term "plant material" encompasses a plant or plant part (e.g. bark, wood, leaves, stems, roots, flowers, fruits, seeds, berries or parts thereof) as well as exudates, and includes material falling within the definition of "botanical raw material" in the Guidance for Industry Botanical Drug Products Draft Guidance, August 2000, US Department of Health and Human Services, Food and Drug Administration Centre for Drug Evaluation and Research. The term "cannabis plant(s)" encompasses wild type *Cannabis sativa* and also variants thereof, including *Cannabis* chemovars (varieties characterized by virtue of chemical composition) which naturally contain different amounts of the individual cannabinoids, also *Cannabis sativa* subspecies *indica* including the variants var. *indica* and var. *kafiristanica*, *Cannabis indica* and also plants which are the result of genetic crosses, self-crosses or hybrids thereof. The term "*Cannabis* plant material" also can encompass plant material derived from one or more cannabis plants, and can comprise any "cannabis plant material" including, e.g., herbal *Cannabis* and dried *Cannabis* biomass. The term "*Cannabis* plant material" also can encompass "decarboxylated *Cannabis* plant material", which refers to *Cannabis* plant material which has been subject to a decarboxylation step in order to convert cannabinoid acids to the corresponding free cannabinoids.

In alternative embodiments, a starting material for a purification process as provided herein is an extract solution containing a cannabinoid or cannabinoid acid obtained from a natural or a synthetic source, e.g., a plant or microbial material. In alternative embodiments, the "extract solution containing a cannabinoid or cannabinoid acid" comprises a solvent extract of a plant or microbial material. Solvents used for extraction for use in the preparation of extract solutions can comprise non-polar solvents, polar solvents such as ethanol, methanol or water, or organic solvents such as liquid carbon dioxide, and combinations thereof. The solvent may be an organic solvent, selected from the group consisting of: non-polar solvents include liquid non-polar solvents comprising lower C1-C12, preferably C3 to C8, straight chain or branched chain alkanes for example, methane, ethane, propane, butane, pentane, toluene, trimethylpentane; a low molecular weight alcohol, polar solvents consisting of for example, ethanol, methanol, water; a low molecular weight chlorinated hydrocarbon, for example, chloroform and dichloromethane; or a supercritical fluid such as $CO_2$ with or without an organic solvent modifier.

In alternative embodiments, the extract is prepared by dissolving or partially dissolving the natural or synthetic, or the plant or microbial material in a solvent, removing insoluble material from the resultant solution (optionally by filtration with or without activated carbon, precipitation, centrifugation and the like), and optionally removing some or all of the extraction solvent from the solution (optionally by rotary evaporation) to form an extract or extract solution or concentrate containing a cannabinoid or cannabinoid acid.

In alternative embodiments, extractions can comprise using a technique referred to as accelerated solvent extraction or may use subcritical water or any combination of water and solvent. In one embodiment, when isolating cannabinoid acids, a modified pH gradient elution solvent is used. The primary purpose of this pH adjustment (the modified pH gradient) is to promote or prevent ionization of the cannabinoid acid. pH modified gradient elution solutions may be achieved by the additional of a small volume of acid or base to the solvent. It may be sufficient to add a relatively weak acid, such as acetic acid, oxalic acid, glycolic acid, carbonic acid or ammonium hydroxide or a small amount of base or buffering agent such as sodium hydroxide, magnesium hydroxide, sodium carbonate or sodium bicarbonate. For any given purification process the optimal amount and type of acid or base used may be determined empirically. An alternative exemplary acidified solvent is 0.1% acetic acid in ethanol or 0.1% sodium hydroxide in ethanol. In alternative embodiments, the neutralizing agent consists of for example sodium hydroxide, sodium carbonate, potassium carbonate, and potassium t-amylate, sodium bicarbonate.

Acidified non-polar and polar solvents of the types described above can be useful in preparation of gradient elutions using ion exchange chromatography. The solvents used in the conversion can comprise an organic solvent, e.g., a non-polar solvent, including a liquid non-polar solvent comprising lower C1-C12, or C3 to C8, straight chain or branched chain alkanes for example, methane, ethane, propane, butane, pentane, toluene, trimethylpentane, hexane; a low molecular weight alcohol, polar solvents consisting of for example, ethanol; a low molecular weight chlorinated hydrocarbon, for example, chloroform and dichloromethane; a heterocyclic compound or cyclic ether for example, tetrahydrofuran and 2-Methyltetrahydrofuran and aromatic ring hydrocarbons such as benzene, toluene, xylene and ethylbenzene.

In alternative embodiments, the elimination catalyst consists of a catalyst and or reagent such as, for example, lithium hydroxide (LiOH), sodium hydroxide (NaOH), potassium hydroxide (KOH), rubidium hydroxide (RbOH), cesium hydroxide (CsOH), magnesium hydroxide ($Mg(OH)_2$), calcium hydroxide ($Ca(OH)_2$), strontium hydroxide ($Sr(OH)_2$), barium hydroxide ($Ba(OH)_2$), potassium hydride and/or sodium hydride, potassium tert-pentoxide, organic superbases, bispidines, multicyclic polyamines, organometallic compounds of reactive metals, wherein optionally the reactive metals comprise organolithium, organo-magnesium, lithium diisopropylamide, n-butyllithium and potassium tert-butoxide, potassium tert-pentoxide, lithium nitride, sodium methoxide, sodium ethoxide, ortho-diethynylbenzene dianion, meta-diethynylbenzene dianion, para-diethynylbenzene dianion, lithium monoxide anion, and/or a methyl anion.

In alternative embodiments, the plant or microbial material is subjected to a decarboxylation step prior to solvent extraction. The purpose of the decarboxylation step is to convert cannabinoid acids present in the plant or microbial material to the corresponding free cannabinoids. In alternative embodiments, the decarboxylation is carried out by heating the plant or microbial material to a defined temperature for a suitable length of time. Decarboxylation of cannabinoid acids is a function of time and temperature, thus at higher temperatures a shorter period of time will be taken for complete decarboxylation of a given amount of cannabinoid acid. In alternative embodiments selecting appropriate conditions for decarboxylation consideration includes minimizing thermal degradation of the desirable, pharmacological cannabinoids into undesirable degradation products, particularly thermal degradation of $\Delta^9$-THC. In alternative embodiments, the decarboxylation is carried out in a multi-step heating process in which the plant or microbial material is: i) heated to a first temperature for a first (relatively short) time period to evaporate off retained water and allow for uniform heating of the plant or microbial material; and ii) the temperature is increased to a second temperature for a second time period (typically longer than the first time period) until at least 95% conversion of the acid cannabinoids to their neutral form has occurred.

In alternative embodiments, the "extract containing a cannabinoid or a cannabinoid acid" prepared from the starting plant or microbial material comprises a "botanical drug substance" prepared from the plant or microbial material, or a polar or non-polar solvent solution of such a botanical drug substance. In the context of this application a "botanical drug substance" is an extract derived from plant or microbial material, which extract fulfills the definition of "botanical drug substance" provided in the Guidance for Industry Botanical Drug Products Draft Guidance, August 2000, US Department of Health and Human Services, Food and Drug Administration Centre for Drug Evaluation and Research of: "A drug substance derived from one or more plants, algae, or macroscopic fungi. It is prepared from botanical raw materials by one or more of the following processes: pulverization, decoction, expression, aqueous extraction, ethanolic extraction, or other similar processes." "Botanical drug substances" derived from cannabis plants include primary extracts prepared by such processes as, for example, maceration, percolation, and solvent extraction.

In alternative embodiments, solvent extraction may be carried out using essentially any solvent that dissolves, or substantially dissolves, cannabinoids/cannabinoid acids, such as for example C1 to C5 alcohols (e.g. ethanol, methanol), C5-C12 alkanes (e.g. hexane), norflurane (HFA134a), 1,1,1,2,3,3,3-Heptafluoropropane (or HFA227), chloroform, dichloromethane, dichloroethane and carbon dioxide. When solvents such as those listed above are used, the resultant extract typically contains non-specific lipid-soluble material. This can optionally be removed by a variety of processes including filtration to remove solids, "winterization", which involves for example chilling to −20° C. or lower followed by filtration to remove waxy ballast, extraction with liquid carbon dioxide and by distillation.

In alternative embodiments, any protocol for the preparation of botanical drug substances from cannabis and hemp plant material can be used, e.g., as described in International patent application WO 02/064109. In alternative embodiments, the botanical drug substance is obtained by carbon dioxide ($CO_2$) extraction, polar solvent extraction or non-polar solvent extraction or combinations thereof followed by a filtration. Optionally a secondary extraction is performed to remove a substantial proportion of non-cannabinoid materials, e.g. waxes, wax esters and glycerides, unsaturated fatty acid residues, terpenes, carotenes, and flavonoids and other ballast.

In alternative embodiments, if it is intended to prepare free cannabinoids from the plant or microbial material, e.g., cannabis, then the material is heated to a defined temperature for a defined period of time in order to partially or substantially decarboxylate cannabinoid acids to free cannabinoids prior to extraction of the botanical drug substance. In alternative embodiments, the botanical drug substance is prepared according to a process comprising the following steps: i) optional decarboxylation of the plant or microbial material, ii) extraction with polar or non-polar solvent, to produce a crude botanical drug substance, iii) optional precipitation with C1-C5 alcohol to reduce the proportion of non-target materials, iv) removing the precipitate (optionally by filtration), v) optional treatment with activated charcoal, and vi) evaporation to remove C1-C5 alcohol and water, thereby producing a final botanical drug substance.

In alternative embodiments, provided are methods for converting first substantially purified cannabidiol (CBD) to $\Delta^8$-tetrahydrocannabinol ($\Delta^8$-THC) and $\Delta^9$-tetrahydrocannabinol ($\Delta^9$-THC), and then further converting the produced $\Delta9$-tetrahydrocannabinol ($\Delta^9$-THC) to $\Delta^8$-tetrahydrocannabinol ($\Delta^8$-THC). As will be appreciated by one knowledgeable in the art and as discussed below, the reaction times may be varied somewhat, producing product at different yields and purities.

Furthermore, functional equivalents may be substituted where appropriate.

In alternative embodiments, an exemplary method of converting CBD to $\Delta^8$-tetrahydrocannabinol ($\Delta^8$-THC) and $\Delta^9$-tetrahydrocannabinol ($\Delta^9$-THC) and further converting ($\Delta^9$-THC) to ($\Delta^8$-THC) comprises: providing a reaction mixture comprising a Lewis acid or non-oxidizing acid catalyst in a reaction solvent, adding a substantially pure CBD or substantially pure CBD and/or ($\Delta^8$-THC) and/or $\Delta^9$-tetrahydrocannabinol ($\Delta^9$-THC) to the reaction mixture, mixing said reaction mixture for a period of time; adding a neutralizing agent to said mixture; filtration of catalyst and neutralizing agent from mixture; optionally allowing mixture to separate into an aqueous and organic phase; optionally dissolving organic phase in a second solvent; adding a stabilizing agent; mixing said reaction mixture for a period of time; adding a elimination catalyst or reagent to said reaction mixture; filtration of stabilizing agent and elimination agent from mixture; optionally allowing mixture to separate into an aqueous phase and an organic phase; optionally adding a further solvent; adding organic phase to a chromatography column and eluting the tetrahydrocannabinol from the organic phase. The tetrahydrocannabinol may then be combined with suitable excipients known in the art, thereby forming a pharmaceutical composition. In one embodiment, the mixture is allowed to separate into an aqueous phase and an organic phase; and optionally the process further comprises removing the organic phase.

In alternative embodiments, the tetrahydrocannabinol at therapeutically effective concentrations or dosages is combined with a pharmaceutically or pharmacologically acceptable carrier, excipient or diluent, either biodegradable or non-biodegradable. Exemplary examples of carriers include, but are by no means limited to, for example, poly(ethylene-vinyl acetate), copolymers of lactic acid and glycolic acid, poly(lactic acid), gelatin, collagen matrices, polysaccharides, poly(D,L lactide), poly(malic acid), poly(caprolactone), celluloses, albumin, starch, casein, dextran, polyesters, ethanol, methacrylate, polyurethane, polyethylene, vinyl polymers, glycols, mixtures thereof and the like. Standard excipients that can be used include gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethycellulose phthalate, non-crystalline cellulose, magnesium aluminum silicate, triethanolamine, polyvinyl alcohol, polyvinylpyrrolidone, sugars and starches. See, for example, Remington: The Science and Practice of Pharmacy, 1995, Gennaro ed.

In some embodiments, the catalyst is a Lewis acid, for example, p-toluenesulfonic acid, boron trifluoride or $BF_3Et_2O$. In some embodiments, the $BF_3Et_2O$ (boron trifluoride diethyl etherate) is in dry methylene chloride, ethylethyl acetate, ethanol, hexane or other organic solvent. In yet other examples, the catalyst may be hydrochloric acid in ethanol or sulfuric acid in cyclohexane.

In some embodiments, the catalyst is a non-oxidizing acid, for example, formic acid, acetic acid or hydrobromic acid. In some embodiments, the non-oxidizing acid is in dry methylene chloride, ethyl acetate, ethanol, hexane or other organic solvent.

In some embodiments, a base is added to the reaction mixture prior to allowing the reaction mixture to separate into organic and aqueous phases. The base may be an alkali metal hydrogen carbonate, carbonate of an alkali metal, lithium hydroxide (LiOH), sodium hydroxide (NaOH), potassium hydroxide (KOH), rubidium hydroxide (RbOH), cesium hydroxide (CsOH), magnesium hydroxide (Mg(OH)), calcium hydroxide (Ca(OH)), strontium hydroxide (Sr(OH)), barium hydroxide (Ba(OH)).

In some embodiments, the organic layer is dried prior to eluting. In these embodiments, a suitable drying or dehydration compound, for example, MgSO4 or $Na_2SO_4$ is used.

In yet other embodiments, the process may be carried out under a nitrogen (e.g., $N_2$) atmosphere.

In alternative embodiments, and as discussed below, yield is determined by looking at the peak area for the isolated compound in the gas chromatography-mass spectra analysis of the crude reaction product mixture and the final reaction product mixture. It is important to note that in the prior art, yield is often calculated on the basis of first isolated crude product before final purification. In some embodiments of processes provided herein yield of Δ9-THC is at least about 75%; in other embodiments, the yield of Δ9-THC is at least about 90%; and in other embodiments, yield of Δ9-THC is at least about 98%; and in yet other embodiments, yield of Δ9-THC is between about 75 to 98% or 99%.

In alternative embodiments, purity is determined by Gas Chromatography-Mass Spectrometry (GC-MS) and/or by analytical high-performance liquid chromatography (HPLC). The total ion chromatogram from the GC-MS gives information similar to that provided by a flame ionization detector (FID)-GC in that the peak area is proportional to the mass of the analytes detected. Total peak area and the peak areas of the individual analytes can be compared in the GC-MS case as long as the masses are in generally the same range. As discussed below, in some embodiments, purity of the Δ9-THC isolated by the process is greater than about 70%, 80%, 90%, 95%, 97% or 98% or more, or purity is greater that about 98% to 99% or 90% to 99.5%.

Chapter III

In alternative embodiments, provided are continuous isolation and purification processes for preparing a substantially pure cannabidiol or a product enriched in cannabidiol from plant or microbial material extracts. In alternative embodiments, provided herein are improved methods for converting cannabidiol (CBD) to $\Delta^8$-THC, including a purification and conversion process based on a simple combination of continuous chromato-graphic gradient elutions and semi continuous isomerization reactions. This exemplary process is simple, efficient and economic.

In alternative embodiments, provided are methods of continuous isolation of cannabinoids in substantially pure form starting from plant extract material and conversion of the purified CBD to form both $\Delta^8$ THC and $\Delta^9$ THC and subsequent conversion of the formed $\Delta^9$ tetrahydrocannabinol into $\Delta^8$ tetrahydrocannabinol.

In alternative embodiments, provided are processes for producing and isolating cannabinoids from cannabis and hemp extracts which contain cannabinoids in minute amounts. In alternative embodiments, provided are processes for producing and isolating cannabinoids from natural materials, including plant or plant extracts, microbes, or botanical drug substances, or synthetically and semi-synthetically prepared cannabinoid products, or from recombinantly engineered microbes, e.g., yeasts or bacteria recombinantly engineered to express one or more cannabinoids. In one embodiment, exemplary methods are inexpensive and provide specific cannabinoid concentrates (e.g., of CBD, $\Delta^8$-THC, $\Delta^9$-THC) of high purity.

In one embodiment, exemplary methods provide a simple and economical continuous process for separating and concentrating cannabinoids from solvent-extracted cannabinoid containing materials. In one embodiment, exemplary methods provide a method that first converts the substantially isolated CBD into a mixture of $\Delta^8$-THC and $\Delta^9$-THC, and then subsequently converts the $\Delta^9$-THC into $\Delta^8$-THC. In alternative embodiments, the solvent-extracted cannabinoid containing materials are derived from synthetic or biological materials such as hemp and *Cannabis* or botanical drug substances, or from microbial materials; and the solvent extraction methods can be polar solvent extractions, nonpolar solvent extractions, or the solvent extraction methods can comprise use of super critical carbon dioxide or mixtures thereof. The solvent extraction methods can extract cannabinoids substantially from the synthetic or biological, e.g., plant, matter, along with other plant matter comprising lipids, waxes, monoterpenes, sesquiterpenes, hydrocarbons, alkaloids, flavonoids and chlorophylls.

In alternative embodiments, methods provided herein comprise subjecting cannabinoid containing solvent extract starting materials to a number of chromatographic resins in various contacting steps using various gradient elution solutions.

In alternative embodiments, the cannabinoids which can be fractionated and isolated using methods as provided herein, or which can be produced in reactions as provided herein, or from which the solvent extracts are derived can be from, or can comprise: $\Delta^9$tetrahydrocannabinol ($\Delta^9$ THC); cannabidiol (CBD); cannabinol (CBN); cannabigerol (CBG); cannabichromene (CBC); cannabidivarol (CBDV); tetrahydrocannabidiol (THCBD); tetrahydrocannabigerol (THCBG); tetrahydrocannabichromene (THCBC); tetrahydrocannabidivarol (THCBDV), or combinations thereof, including carboxylic acid precursors of the foregoing compounds and related naturally occurring compounds and their derivatives.

In alternative embodiments, provides are methods of preparing or obtaining a substantially pure cannabinoid or a product enriched in a given cannabinoid comprising:
(i) obtaining an extract or extract solution containing a cannabinoid or a cannabinoid acid from a plant or microbial material;
(ii) filtering the extract of step (i) to remove solids and color bodies;
(iii) removing the extract solvent (as an extract fraction);
(v) continuously loading of an amount of extract solution over a defined time increment over multiple stationary phase resins columns such as a normal phase, reverse phase and/or ion exchange chromatographic resin;
(vi) continuously eluting the extract solution using multiple defined gradient elution solutions at specific time increments and volumes;
(vii) continuously collecting the gradient elution fractions;
(viii) removing the gradient elution solvent from the produced fractions to generate a substantially purified extract
(ix) optionally loading of specific first gradient elution fractions on a reverse phase, ion exchange or normal chromatographic resin;
(x) continuously eluting the first gradient elution fractions with a second gradient elution solvent; and,
(xi) removing of the second gradient elution solvent from the produced fractions to produce a purified extract.

In alternative embodiments, the methods further comprise:
a step (xii): loading of first and second gradient elution solvents s onto an ion exchange chromatographic resin;
a step (xiii): eluting an extract solution from the ion exchange chromatographic resin of step (xi) using a gradient solvent and collecting the gradient elution fractions; and
(xiv) removing the gradient elution solution from the produced fractions of step (xiii) to produce purified and substantially purified extract.

In alternative embodiments, provided are methods of converting CBD to $\Delta^8$ THC and $\Delta^9$ THC comprising:
(a) providing a reaction mixture comprising a catalyst in an organic solvent;
(b) adding CBD material from steps (viii) and steps (xiii), above;

(c) mixing said reaction mixture;
(d) allowing the mixture to separate into an aqueous phase and an organic phase;
optionally adding a second solvent; and
(e) removing the organic phase; and,
optionally, repeating steps (a) through (e).

In alternative embodiments, provided are methods for converting CBD to substantially pure $\Delta^8$ THC comprising:
  (a) providing a reaction mixture comprising a CBD in an organic solvent;
  (b) adding a catalyst to the reaction mixture under a nitrogen atmosphere;
  (c) stirring the reaction mixture;
  (d) controlling the reaction temperature and continuously measuring the rate of reaction by observing conversion of CBD to first $\Delta^9$-THC and second order of reaction $\Delta^8$-THC;
  (d) adding $NaHCO_3$ or equivalent to the reaction mixture once $\Delta^9$-THC has be substantially converted to $\Delta^8$-THC;
  (e) allowing the mixture to separate into an aqueous phase and an organic phase and optionally adding a second solvent;
  (f) removing the organic phase, which comprises substantially the converted $\Delta^8$-THC; and
  optionally repeating steps (a) through (f);
  optionally performing steps (v) through (xiv).

In alternative embodiments, a "substantially pure" preparation of cannabinoid is defined as a preparation having a chromatographic purity (of the desired cannabinoid or cannabinoid acid) of greater than about 75%, or greater than about 96%, or greater than about 97%, or greater than about 98%, or greater than about 99%, or greater than about 99.5%, or between about 70% and 99.9%, as determined by area normalisation of an HPLC profile.

In alternative embodiments, the term "product enriched in a given cannabinoid" encompasses preparations having at least about 50%, or greater than about 75%, or greater than about 90%, 95% or 98%, or between about 50% and 99.9%, chromatographic purity, for the desired cannabinoid.

In alternative embodiments, a non-purified, or non-substantially purified, product can comprise a greater proportion of impurities, non-target materials and/or other cannabinoids than a "substantially pure" preparation. The cannabinoid can be (e.g., a cannabinoid purified or isolated by, or made by a reaction of, a method as provided herein can be): $\Delta^9$tetrahydrocannabinol ($\Delta^9$ THC); cannabidiol (CBD); cannabinol (CBN); cannabigerol (CBG); cannabichromene (CBC); cannabidivarol (CBDV); tetra-hydrocannabidiol (THCBD); tetra-hydrocannabigerol (THCBG); tetra-hydrocannabichromene (THCBC); or, tetra-hydrocannabidivarol (THCBDV); the carboxylic acid precursors of the foregoing compounds; and related naturally occurring compounds and their derivatives.

In alternative embodiments, the term "cannabinoids" e.g., a cannabinoid purified or isolated by, or made by a reaction of a process as provided herein, includes or refers to a family of natural products that can contain a 1,1'-di-methyl-pyrane ring, a variedly derivatized aromatic ring and/or a variedly unsaturated cyclohexyl ring and their immediate chemical precursors.

In alternative embodiments, the term "cannflavins", e.g., a cannflavin purified or isolated by, or made by a reaction of a process as provided herein, includes or refers to a family of natural products that can contain a 1,4-pyrone ring fused to a variedly derivatized aromatic ring and linked to a second variedly derivatized aromatic ring.

In alternative embodiments, the term "Lewis acid" refers to a powerful electron pair acceptor; and examples include but are by no means limited to $BF_3Et_2O$ (boron trifluoride ditheyl etherate), p-toluenesulfonic acid and boron trifluoride.

In alternative embodiments, the term "non-oxidizing acid" refers to hydrobromic, hydrochloric, hydrofluoric, acetic, benzoic, chloroacetic, formic, phosphoric, sulfuric, trifluroacetic and oxalic acids.

In alternative embodiments, the term "stabilizing agent" refers to a zinc chloride, hydrogen chloride, methylene chloride, simonkolleite, and mixtures thereof; and examples include but are by no means limited to zinc chloride, hydrogen chloride, simonkolleite, and polymorphs and hydrates thereof.

In alternative embodiments, the term "essential oils", e.g., an essential oil used as a starting material in a process as provided herein, or an essential oil that may be isolated by a process as provided herein, includes or refers to a family of natural products that can contain a multiple of the 5-membered isoprene unit variedly substituted, often cyclized to form one or more ring systems; they may also contain series of aldehydes and/or ketones and esters of a variety of carboxylic acid substituted compounds.

In alternative embodiments, provided are methods for extracting and/or purifying cannabinoids from any plant or microbial material extract known to contain such cannabinoids, cannflavins and essential oils; and, optionally to purify cannflavins and to optionally purify essential oils. In alternative embodiments, the extract is passed through a series of chromatographic columns, for example, a normal phase column, a reversed phase column or an ion exchange column as a continuous column configuration.

In one embodiment, the chromatographic column is arranged for gradient elution fractioning using normal phase, reverse phase and/or ion exchange chromatography. In one embodiment $\Delta^9$-THC and $\Delta^8$-THC and CBD are fractionated out of the eluent. For example, in one embodiment, as the extract is passed over the column, $\Delta^9$-THC, $\Delta^8$-THC and CBD is differentially retained or detained (e.g., reversibly bound) on the column. As a result, as the extract comes off the column, the initial fractions eluted off the column will be (substantially) free of $\Delta^8$-THC and CBD. The fractions free of $\Delta^8$-THC and CBD are pooled, thereby producing an extract with $\Delta^9$-THC, $\Delta^8$-THC and CBD substantially removed (e.g., in alternative embodiments, "substantially removed" or "substantially fractionated" means at least 85%, 90%, 95%, 98%, 99% or 99.5% or more removed or fractionated).

In some embodiments, (substantially) only $\Delta^8$-THC is substantially fractionated out of the eluent. For example, in one embodiment, as the extract or pooled fractions from a previous normal phase, reverse phase and/or ion exchange elution are passed over the column, $\Delta^8$-THC is differentially retained or detained (e.g., reversibly bound) on the column. As a result, as the extracts are pooled previous elution fractions comes off the column, the initial fractions eluted off the column will be free of $\Delta^8$-THC. These fractions free of $\Delta^8$-THC are pooled, thereby producing an extract with $\Delta^9$-THC substantially removed (e.g., in alternative embodiments, "substantially removed" or "substantially fractionated" means at least 85%, 90%, 95%, 98%, 99% or 99.5% or more removed or fractionated).

In some embodiments, when using a continuous chromatography apparatus or device, a series of columns are arranged, for example 3, 4, 5, 6, 7, 8 or more, or between 3 and 30 or more, columns are arranged in a continuous rotation traveling through a series of contact points where gradient elution solutions and extract solution are introduced at fixed points for a period of time allowing for continuous loading and elution, and collection of fractions. The first column is loaded with extract solution at the first position (or station). The first column is then moved to the second position where the first gradient elution is introduced (or loaded) while at the same time the second column is loaded with extract solution at position one. The first column then rotates (i.e., is moved) to the third position where the second gradient solvent is introduced, the second column moves to the second position where the first gradient solvent is introduced and the third column is loaded with extract solution at position one. The first column then moves to the fourth position where the third gradient solvent is introduced, the second column moves to the third position where the second gradient solvent is introduced, the third column moves to the second position where the first gradient solvent is introduced and the fourth column is loaded with extract solution at position one. The first column then moves to the fifth position where the fourth gradient solvent is introduced, the second column moves to the fourth position where the third gradient solvent is introduced, the third column moves to the third position where the second gradient solvent is introduced, the fourth column moves to the second position where the first gradient solvent is introduced and the fifth column is loaded with extract solution at position one. The first column then moves to the sixth position where the fifth gradient solvent is introduced, the second column moves to the fifth position where the fourth gradient solvent is introduced, the third column moves to the fourth position where the third gradient solvent is introduced, the fourth column moves to the third position where the second gradient solvent is introduced, the fifth column moves to the second position where the first gradient solvent is introduced and the sixth column is loaded with extract solution at position one. The first column then moves or returns to the first position where extract solution is loaded, the second column moves to the sixth position where the fifth gradient solvent is introduced, the third column moves to the fifth position where the fourth gradient solvent is introduced, the fourth column moves to the fourth position where the third gradient solvent is introduced, the fifth column moves to the third position where the second gradient solvent is introduced and the sixth column moves to the second position where the first gradient solvent is introduced. The equipment is generally described in U.S. Pat. Nos. 4,764,276, 4,808,317, and 4,710,364, for example, each of which are incorporated herein by reference.

In a particular embodiment the first gradient solvent elutes CBD, CBG and CBN and is substantially fractionated in the eluent. For example, in one embodiment, as the extract or pooled fractions from a normal phase, reverse phase and/or ion exchange elution are passed over the column, CBD, CBG and CBN is differentially produced in the eluent (e.g., by use of a gradient elution process). In a particular embodiment second gradient solvent elutes CBD and is substantially fractionated in the eluent. For example, in one embodiment, as the extract or pooled fractions from a normal phase, reverse phase and/or ion exchange elution are passed over the column, CBD is differentially produced in the eluent. In a particular embodiment the third gradient solvent elutes CBD and $\Delta^9$-THC and is substantially fractionated in the eluent. For example, in one embodiment, as the extract or pooled fractions from a normal phase, reverse phase and/or ion exchange elution are passed over the column, CBD and $\Delta^9$-THC is differentially produced in the eluent. In a particular embodiment the fourth gradient elutes $\Delta^9$-THC and is substantially fractionated in the eluent. For example, in one embodiment, as the extract or pooled fractions from a normal phase, reverse phase and/or ion exchange elution are passed over the column, $\Delta^9$-THC is differentially produced in the eluent. In a particular embodiment the fifth gradient elutes CBC, THC-A, terpenes and $\Delta^9$-THC and is substantially fractionated in the eluent. For example, in one embodiment, as the extract or pooled fractions from a normal phase, reverse phase and/or ion exchange elution are passed over the column, CBC, THC-A, terpenes and $\Delta^9$-THC is differentially produced in the eluent.

In some embodiments, when using a continuous chromatography apparatus or device, a series of columns are arranged for example 3, 4, 5, 6, 7, 8 or more, or between 3 and 30 or more, columns are arranged in a continuous rotation traveling through a series of contact points where gradient elution solutions and extract solution are introduced at fixed points for a period of time allowing for continuous loading and elution, and collection of fractions. The first column is loaded with extract solution at the first position (or station). The first column is then moved to the second position where the first gradient elution is introduced (or loaded) while at the same time the second column is loaded with extract solution at position one. The first column then rotates (i.e., is moved) to the third position where the second gradient solvent solution is introduced, the second column moves to the second position where the first gradient solvent is introduced and the third column is loaded with extract solution at position one. The first column then moves to the fourth position where the third gradient solvent is introduced, the second column moves to the third position where the second gradient solvent is introduced, the third column moves to the second position where the first gradient solvent is introduced and the fourth column is loaded with extract solution at position one. The first column then moves to the fifth position where the fourth gradient solvent is introduced, the second column moves to the fourth position where the third gradient solvent is introduced, the third column moves to the third position where the second gradient solvent is introduced, the fourth column moves to the second position where the first gradient solvent is introduced and the fifth column is loaded with extract solution at position one. The first column then moves to the sixth position where the fifth gradient solvent is introduced, the second column moves to the fifth position where the fourth gradient solvent is introduced, the third column moves to the fourth position where the third gradient solvent is introduced, the fourth column moves to the third position where the second gradient solvent is introduced, the fifth column moves to the second position where the first gradient solvent is introduced and the sixth column is loaded with extract solution at position one. The first column then moves or returns to the first position where extract solution is loaded, the second column moves to the sixth position where the fifth gradient solvent is introduced, the third column moves to the fifth position where the fourth gradient solvent is introduced, the fourth column moves to the fourth position where the third gradient solvent is introduced, the fifth column moves to the third position where the second gradient solvent is introduced and the sixth column moves to the second position where the first gradient solvent is introduced. In a particular embodiment the first gradient solvent elutes CBD, CBG and CBN and is substantially fractionated in the eluent. For example, in one embodiment, as the extract or pooled fractions from a normal phase, reverse phase and/or ion exchange elution are passed over the column, CBD, CBG and CBN is differentially produced in the eluent (e.g., by use of a gradient elution process). In a particular embodiment second gradient solvent elutes CBD and is substantially fractionated in the eluent. For example, in one embodiment, as the extract or pooled fractions from a normal phase, reverse phase and/or ion exchange elution are passed over the column, CBD is differentially produced in the eluent. In a particular embodiment the third gradient solvent elutes CBD and $\Delta^9$-THC and is substantially fractionated in the eluent. For example, in one embodiment, as the extract or pooled fractions from a normal phase, reverse phase and/or ion exchange elution are passed over the column, CBD and $\Delta^9$-THC is differentially produced in the eluent. In a particular embodiment the fourth gradient elutes $\Delta^9$-THC and is substantially fractionated in the eluent. For example, in one embodiment, as the extract or pooled fractions from a normal phase, reverse phase and/or ion exchange elution are passed over the column, $\Delta^9$-THC is differentially produced in the eluent. In a particular embodiment the fifth gradient elutes CBC, THC-A, terpenes and $\Delta^9$-THC and is substantially fractionated in the eluent. For example, in one embodiment, as the extract or pooled fractions from a normal phase, reverse phase and/or ion exchange elution are passed over the column, CBC, THC-A, terpenes and $\Delta^9$-THC is differentially produced in the eluent. The second gradient solvent containing CBD is combined with a Lewis acid or non-oxidizing acid catalyst, optionally additional CBD or substantially pure CBD and/or Δ9-tetrahydrocannabinol (Δ9-THC) can be added to the reaction mixture, mixing said reaction mixture for a period of time at a controlled temperature to first convert CBD to $\Delta^9$-THC and continue to the second order reaction to convert formed $\Delta^9$-THC to second order reaction $\Delta^8$-THC; adding a neutralizing agent to said mixture once substantial conversion of $\Delta^9$-THC to $\Delta^8$-THC is observed by sample analysis such as TLC, HPLC or GCMS; filtration of catalyst and neutralizing agent from mixture; optionally allowing mixture to separate into an aqueous and organic phase; optionally adding a further solvent; adding organic phase to a continuous or fixed chromatography column and eluting the $\Delta^8$-THC tetrahydrocannabinol from the organic phase. The tetrahydrocannabinol may then be combined with suitable excipients known in the art, thereby forming a pharmaceutical composition. In one embodiment, the mixture is allowed to separate into an aqueous phase and an organic phase; and optionally the process further comprises removing the organic phase.

In some embodiments, (substantially) only CBD is substantially fractionated out of the eluent. For example, in one embodiment, as the extract or pooled fractions from a previous normal phase, reverse phase and/or ion exchange elution are passed over the column, CBD is differentially retained or detained (e.g., reversibly bound) on the column. As a result, as the extract or pooled previous elution fractions comes off the column, the initial fractions eluted off the column will be (substantially) free of CBD. These fractions free of CBD are pooled, thereby producing an extract with CBD substantially removed (e.g., in alternative embodiments, "substantially removed" or "substantially fractionated" means at least 85%, 90%, 95%, 98%, 99% or 99.5% or more removed or fractionated).

In some embodiments, $\Delta^9$-THC carboxylic acid species or $\Delta^9$-THCA and CBD carboxylic acid species CBDA are fractionated out of out of the eluent. For example, in one embodiment, as the extract or pooled fractions from a first elution are passed over the column, $\Delta^9$-THCA and CBDA are differentially retained or detained (e.g., reversibly bound) on the column. As a result, as the extract or pooled first elution fractions comes off the column, the initial fractions eluted off the column will be (substantially) free of $\Delta^9$-THCA and CBDA. These fractions (substantially) free of $\Delta^9$-THCA and CBDA are pooled, thereby producing an extract with $\Delta^9$-THCA and CBDA substantially removed (e.g., in alternative embodiments, "substantially removed" or "substantially fractionated" means at least 85%, 90%, 95%, 98%, 99% or 99.5% or more removed or fractionated).

In some embodiments, the $\Delta^9$-THC may be eluted from the column, extracted or concentrated, for purifying, or substantially purifying, $\Delta^9$-THC. In alternative embodiments, the chromatographic column is arranged for fractionating (e.g., sequentially fractionating) a specific cannabinoid or groups of cannabinoids or their carboxylic acid species, cannflavin or essential oil or class of cannabinoids, cannflavins or essential oils out of the eluent, for example, cannabidiol (CBD), cannabinol (CBN), cannabigerol (CBG), cannabichromene (CBC), cannabidivarol (CBDV), tetrahydrocannabidiol (THCBD), tetrahydrocannabigerol (THCBG), tetrahydrocannabichromene (THCBC), tetrahydrocannabidivarol (THCBDV), $\Delta^8$-THC, the carboxylic acid precursors of the foregoing compounds, and related naturally occurring compounds and their derivatives. In alternate embodiments, the chromatographic column is arranged for fractionating (e.g., sequentially fractionating) cannflavins and related naturally occurring compounds and their derivatives. In alternate embodiments, the system is arranged to fractionate the components of essential oils. The list of compounds provided herein is not exhaustive and is in no way intended to be limiting. In these embodiments, the compound(s) of interest are retained or detained (e.g., reversibly bound) on the column so that fractions (alternatively, the last fractions) of the extract eluted from the column contain the compounds(s) of interest. In alternative embodiments, fractions containing the compound(s) of interest are pooled. In some embodiments, different compounds may be extracted with different solvents and then combined into a single extract. As will be appreciated by one knowledgeable in the art, in this manner, several different cannabinoids could be purified from a single extract.

In alternative embodiments, the "plant material or microbial" will be derived from one or more cannabis or hemp plants, or from other plants, or microbes such as yeast, lichen, algae or bacteria. The term "plant or microbial material" encompasses a plant or plant part (e.g. bark, wood, leaves, stems, roots, flowers, fruits, seeds, berries or parts thereof) as well as exudates, and includes material falling within the definition of "botanical raw material" in the Guidance for Industry Botanical Drug Products Draft Guidance, August 2000, US Department of Health and Human Services, Food and Drug Administration Centre for Drug Evaluation and Research. The term "cannabis plant(s)" encompasses wild type *Cannabis sativa* and also variants thereof, including *Cannabis* chemovars (varieties characterized by virtue of chemical composition) which naturally contain different amounts of the individual cannabinoids, also *Cannabis sativa* subspecies *indica* including the variants var. *indica* and var. *kafiristanica, Cannabis indica* and also plants which are the result of genetic crosses, self-crosses or hybrids thereof. The term "*Cannabis* plant material" also can encompass plant material derived from one or more cannabis plants, and can comprise any "cannabis plant material" including, e.g., herbal *Cannabis* and dried *Cannabis* biomass. The term "*Cannabis* plant material" also can encompass "decarboxylated *Cannabis* plant material", which refers to *Cannabis* plant material which has been subject to a decarboxylation step in order to convert cannabinoid acids to the corresponding free cannabinoids.

In alternative embodiments, a starting material for a purification process as provided herein is an extract solution containing a cannabinoid or cannabinoid acid obtained from a natural or a synthetic source, e.g., a plant or microbial material. In alternative embodiments, the "extract solution containing a cannabinoid or cannabinoid acid" comprises a solvent extract of a plant or microbial material. Solvents used for extraction for use in the preparation of extract solutions can comprise non-polar solvents, polar solvents such as ethanol, methanol or water, or organic solvents such as liquid carbon dioxide, and combinations thereof. The solvent may be an organic solvent, selected from the group consisting of: non-polar solvents include liquid non-polar solvents comprising lower C1-C12, preferably C3 to C8, straight chain or branched chain alkanes for example, methane, ethane, propane, butane, pentane, toluene, trimethylpentane; a low molecular weight alcohol, polar solvents consisting of for example, ethanol, methanol, water; a low molecular weight chlorinated hydrocarbon, for example, chloroform and dichloromethane; or a supercritical fluid such as $CO_2$ with or without an organic solvent modifier.

In alternative embodiments, the extract is prepared by dissolving or partially dissolving the natural or synthetic, or the plant or microbial material in a solvent, removing insoluble material from the resultant solution (optionally by filtration with or without activated carbon, precipitation, centrifugation and the like), and optionally removing some or all of the extraction solvent from the solution (optionally by rotary evaporation) to form an extract or extract solution or concentrate containing a cannabinoid or cannabinoid acid.

In alternative embodiments, extractions can comprise using a technique referred to as accelerated solvent extraction or may use subcritical water or any combination of water and solvent. In one embodiment, when isolating cannabinoid acids, a modified pH gradient elution solution is used. The primary purpose of this pH adjustment (the modified pH gradient) is to promote or prevent ionization of the cannabinoid acid. pH modified gradient elution solutions may be achieved by the additional of a small volume of acid or base to the solvent. It may be sufficient to add a relatively weak acid, such as acetic acid, oxalic acid, glycolic acid, carbonic acid or ammonium hydroxide or a small amount of base or buffering agent such as sodium hydroxide, magnesium hydroxide, sodium carbonate or sodium bicarbonate. For any given purification process the optimal amount and type of acid or base used may be determined empirically. An alternative exemplary acidified solvent is 0.1% acetic acid in ethanol or 0.1% sodium hydroxide in ethanol. In alternative embodiments, the neutralizing agent consists of for example sodium hydroxide, sodium carbonate, potassium carbonate, and potassium t-amylate, sodium bicarbonate.

Acidified non-polar and polar solvents of the types described above can be useful in preparation of gradient elutions using ion exchange chromatography. The solvents used in the conversion can comprise an organic solvent, e.g., a non-polar solvent, including a liquid non-polar solvent comprising lower C1-C12, or C3 to C8, straight chain or branched chain alkanes for example, methane, ethane, propane, butane, pentane, toluene, trimethylpentane, hexane; a low molecular weight alcohol, polar solvents consisting of for example, ethanol; a low molecular weight chlorinated hydrocarbon, for example, chloroform and dichloromethane; a heterocyclic compound or cyclic ether for example, tetrahydrofuran and 2-Methyltetrahydrofuran and aromatic ring hydrocarbons such as benzene, toluene, xylene and ethylbenzene.

In alternative embodiments, the plant or microbial material is subjected to a decarboxylation step prior to solvent extraction. The purpose of the decarboxylation step is to convert cannabinoid acids present in the plant or microbial material to the corresponding free cannabinoids. In alternative embodiments, the decarboxylation is carried out by heating the plant or microbial material to a defined temperature for a suitable length of time. Decarboxylation of cannabinoid acids is a function of time and temperature, thus at higher temperatures a shorter period of time will be taken for complete decarboxylation of a given amount of cannabinoid acid. In alternative embodiments selecting appropriate conditions for decarboxylation consideration includes minimizing thermal degradation of the desirable, pharmacological cannabinoids into undesirable degradation products, particularly thermal degradation of $\Delta^9$-THC. In alternative embodiments, the decarboxylation is carried out in a multi-step heating process in which the plant or microbial material is: i) heated to a first temperature for a first (relatively short) time period to evaporate off retained water and allow for uniform heating of the plant or microbial material; and ii) the temperature is increased to a second temperature for a second time period (typically longer than the first time period) until at least 95% conversion of the acid cannabinoids to their neutral form has occurred.

In alternative embodiments, the "extract containing a cannabinoid or a cannabinoid acid" prepared from the starting plant or microbial material comprises a "botanical drug substance" prepared from the plant material, or a polar or non-polar solvent solution of such a botanical drug substance. In the context of this application a "botanical drug substance" is an extract derived from plant or microbial material, which extract fulfills the definition of "botanical drug substance" provided in the Guidance for Industry Botanical Drug Products Draft Guidance, August 2000, US Department of Health and Human Services, Food and Drug Administration Centre for Drug Evaluation and Research of: "A drug substance derived from one or more plants, algae, or macroscopic fungi. It is prepared from botanical raw materials by one or more of the following processes: pulverization, decoction, expression, aqueous extraction, ethanolic extraction, or other similar processes." "Botanical drug substances" derived from cannabis plants include primary extracts prepared by such processes as, for example, maceration, percolation, and solvent extraction.

In alternative embodiments, solvent extraction may be carried out using essentially any solvent that dissolves, or substantially dissolves, cannabinoids/cannabinoid acids, such as for example C1 to C5 alcohols (e.g. ethanol, methanol), C5-C12 alkanes (e.g. hexane), norflurane (HFA134a), 1,1,1,2,3,3,3-Heptafluoropropane (or HFA227), chloroform, dichloromethane, dichloroethane and carbon dioxide. When solvents such as those listed above are used, the resultant extract typically contains non-specific lipid-soluble material. This can optionally be removed by a variety of processes including filtration to remove solids, "winterization", which involves for example chilling to −20° C. or lower followed by filtration to remove waxy ballast, extraction with liquid carbon dioxide and by distillation.

In alternative embodiments, any protocol for the preparation of botanical drug substances from cannabis and hemp plant material can be used, e.g., as described in International patent application WO 02/064109. In alternative embodiments, the botanical drug substance is obtained by carbon dioxide ($CO_2$) extraction, polar solvent extraction or non-polar solvent extraction or combinations thereof followed by a filtration. Optionally a secondary extraction is performed to remove a substantial proportion of non-cannabinoid materials, e.g. waxes, wax esters and glycerides, unsaturated fatty acid residues, terpenes, carotenes, and flavonoids and other ballast.

In alternative embodiments, if it is intended to prepare free cannabinoids from the plant or microbial material, e.g., cannabis, then the material is heated to a defined temperature for a defined period of time in order to partially or substantially decarboxylate cannabinoid acids to free cannabinoids prior to extraction of the botanical drug substance. In alternative embodiments, the botanical drug substance is prepared according to a process comprising the following steps: i) optional decarboxylation of the plant or microbial material, ii) extraction with polar or non-polar solvent, to produce a crude botanical drug substance, iii) optional precipitation with C1-C5 alcohol to reduce the proportion of non-target materials, iv) removing the precipitate (optionally by filtration), v) optional treatment with activated charcoal, and vi) evaporation to remove C1-C5 alcohol and water, thereby producing a final botanical drug substance.

In alternative embodiments, provided are methods for converting first substantially purified cannabidiol (CBD) to Δ8-tetrahydrocannabinol (Δ8-THC) and Δ9-tetrahydrocannabinol (Δ9-THC), and then further converting the produced Δ9-tetrahydrocannabinol (Δ9-THC) to Δ8-tetrahydrocannabinol (Δ8-THC). As will be appreciated by one knowledgeable in the art and as discussed below, the reaction times may be varied somewhat, producing product at different yields and purities.

Furthermore, functional equivalents may be substituted where appropriate.

In alternative embodiments, an exemplary method of converting CBD to Δ8-tetrahydrocannabinol (Δ8-THC) and Δ9-tetrahydrocannabinol (Δ9-THC) and further converting (Δ9-THC) to (Δ8-THC) comprises: providing a reaction mixture comprising a Lewis acid or non-oxidizing acid catalyst in a reaction solvent, adding a substantially pure CBD or substantially pure CBD and/or (Δ9-THC) to the reaction mixture, mixing said reaction mixture for a period of time; adding a neutralizing agent to said mixture when it is observed that Δ8-tetrahydrocannabinol (Δ8-THC) is substantially formed and Δ9-tetrahydrocannabinol (Δ9-THC) has been substantially eliminated; filtration of catalyst and neutralizing agent from mixture; optionally allowing mixture to separate into an aqueous and organic phase; optionally adding a further solvent; adding organic phase to a continuous or fixed bed chromatography column and eluting the Δ8-tetrahydrocannabinol (Δ8-THC) from the organic phase.

The tetrahydrocannabinol may then be combined with suitable excipients known in the art, thereby forming a pharmaceutical composition. In one embodiment, the mixture is allowed to separate into an aqueous phase and an organic phase; and optionally the process further comprises removing the organic phase).

In alternative embodiments, the tetrahydrocannabinol at therapeutically effective concentrations or dosages is combined with a pharmaceutically or pharmacologically acceptable carrier, excipient or diluent, either biodegradable or non-biodegradable. Exemplary examples of carriers include, but are by no means limited to, for example, poly(ethylene-vinyl acetate), copolymers of lactic acid and glycolic acid, poly(lactic acid), gelatin, collagen matrices, polysaccharides, poly(D,L lactide), poly(malic acid), poly(caprolactone), celluloses, albumin, starch, casein, dextran, polyesters, ethanol, methacrylate, polyurethane, polyethylene, vinyl polymers, glycols, mixtures thereof and the like. Standard excipients that can be used include gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethycellulose phthalate, non-crystalline cellulose, magnesium aluminum silicate, triethanolamine, polyvinyl alcohol, polyvinylpyrrolidone, sugars and starches. See, for example, Remington: The Science and Practice of Pharmacy, 1995, Gennaro ed.

In some embodiments, the catalyst is a Lewis acid, for example, p-toluenesulfonic acid, boron trifluoride or $BF_3Et_2O$. In some embodiments, the $BF_3Et_2O$ (boron trifluoride diethyl etherate) is in dry methylene chloride, ethyl acetate, ethanol, hexane or other organic solvent. In yet other examples, the catalyst may be hydrochloric acid in ethanol or sulfuric acid in cyclohexane.

In some embodiments, the catalyst is a non-oxidizing acid, for example, formic acid, acetic acid or hydrobromic acid. In some embodiments, the non-oxidizing acid is in dry methylene chloride, ethyl acetate, ethanol, hexane or other organic solvent.

In some embodiments, a base is added to the reaction mixture prior to allowing the reaction mixture to separate into organic and aqueous phases. The base may be an alkali metal hydrogen carbonate, carbonate of an alkali metal, lithium hydroxide (LiOH), sodium hydroxide (NaOH), potassium hydroxide (KOH), rubidium hydroxide (RbOH), cesium hydroxide (CsOH), magnesium hydroxide (Mg(OH)), calcium hydroxide (Ca(OH)), strontium hydroxide (Sr(OH)), barium hydroxide (Ba(OH)).

In some embodiments, the organic layer is dried prior to eluting. In these embodiments, a suitable drying or dehydration compound, for example, MgSO4 or $Na_2SO_4$ is used.

In yet other embodiments, the process may be carried out under a nitrogen (e.g., $N_2$) atmosphere.

In alternative embodiments, and as discussed below, yield is determined by looking at the peak area for the isolated compound in the gas chromatography-mass spectra analysis of the crude reaction product mixture and the final reaction product mixture. It is important to note that in the prior art, yield is often calculated on the basis of first isolated crude product before final purification. In some embodiments of processes provided herein yield of Δ8-THC is at least about 75%; in other embodiments, the yield of Δ8-THC is at least about 90%; and in other embodiments, yield of Δ8-THC is at least about 98%; and in yet other embodiments, yield of Δ8-THC is between about 75 to 98% or 99%.

In alternative embodiments, purity is determined by Gas Chromatography-Mass Spectrometry (GC-MS) and/or by analytical high-performance liquid chromatography (HPLC). The total ion chromatogram from the GC-MS gives information similar to that provided by a flame ionization detector (FID)-GC in that the peak area is proportional to the mass of the analytes detected. Total peak area and the peak areas of the individual analytes can be compared in the GC-MS case as long as the masses are in generally the same range. As discussed below, in some embodiments, purity of the Δ8-THC isolated by the process is greater than about 90%, 95%, 97% or 98%, or purity is greater that about 98% to 99%.

Chapter IV

In alternative embodiments, provided are continuous isolation and purification processes for preparing a substantially pure cannabinoids or a product enriched in cannabis from plant or microbial material extracts. In alternative embodiments, provided herein are improved methods for purification and conversion processes based on a simple combination of continuous chromato-graphic gradient elutions. This exemplary process is simple, efficient and economic.

In alternative embodiments, provided are processes for producing and isolating cannabinoids from cannabis and hemp extracts which contain cannabinoids in minute amounts. In alternative embodiments, provided are processes for producing and isolating cannabinoids from natural materials, including plant or plant extracts, microbes, or botanical drug substances, or synthetically and semi-synthetically prepared cannabinoid products, or from recombinantly engineered microbes, e.g., yeasts or bacteria recombinantly engineered to express one or more cannabinoids. In one embodiment, exemplary methods are inexpensive and provide specific cannabinoid concentrates (e.g., of CBD, $\Delta^8$-THC, $\Delta^9$-THC) of high purity.

In one embodiment, exemplary methods provide a simple and economical continuous process for separating and concentrating cannabinoids from solvent-extracted cannabinoid containing materials. In alternative embodiments, the solvent-extracted cannabinoid containing materials are derived from synthetic or biological materials such as hemp and *Cannabis* or botanical drug substances, or from microbial materials; and the solvent extraction methods can be polar solvent extractions, nonpolar solvent extractions, or the solvent extraction methods can comprise use of super critical carbon dioxide or mixtures thereof. The solvent extraction methods can extract cannabinoids substantially from the synthetic or biological, e.g., plant, matter, along with other plant matter comprising lipids, waxes, monoterpenes, sesquiterpenes, hydrocarbons, alkaloids, flavonoids and chlorophylls.

In alternative embodiments, methods provided herein comprise subjecting cannabinoid containing solvent extract starting materials to a number of chromatographic resins in various contacting steps using various gradient elution solutions.

In alternative embodiments, the cannabinoids from which can be fractionated and isolated using methods as provided herein, or which can be produced in reactions as provided herein, or which the solvent extracts are derived can be from, or can comprise: $\Delta^9$tetrahydrocannabinol ($\Delta^9$ THC); cannabidiol (CBD); cannabinol (CBN); cannabigerol (CBG); cannabichromene (CBC); cannabidivarol (CBDV); tetrahydrocannabidiol (THCBD); tetrahydrocannabigerol (THCBG); tetrahydrocannabichromene (THCBC); tetrahydrocannabidivarol (THCBDV), or combinations thereof, including carboxylic acid precursors of the foregoing compounds and related naturally occurring compounds and their derivatives.

In alternative embodiments, provides are methods of preparing or obtaining a substantially pure cannabinoid or a product enriched in a given cannabinoid comprising:
  (i) obtaining an extract or extract solution containing a cannabinoid or a cannabinoid acid from a plant or microbial material;
  (ii) filtering the extract of step (i) to remove solids and color bodies;
  (iii) removing the extract solvent (as an extract fraction);
  (v) continuously loading of an amount of extract solution over a defined time increment over multiple stationary phase resins columns such as a normal phase, reverse phase and/or ion exchange chromatographic resin;
  (vi) continuously eluting the extract solution using multiple defined gradient elution solutions at specific time increments and volumes;
  (vii) continuously collecting the gradient elution fractions;
  (viii) removing the gradient elution solution from the produced fractions to generate a substantially purified extract
  (ix) optionally loading of specific first gradient elution fractions on a reverse phase, ion exchange or normal chromatographic resin;
  (x) continuously eluting the first gradient elution fractions with a second gradient elution solvent; and,
  (xi) removing of the second gradient elution solvent from the produced fractions to produce a purified extract.

In alternative embodiments, the methods further comprise:
  a step (xii): loading of first and second gradient elution solvents s onto an ion exchange chromatographic resin;
  a step (xiii): eluting an extract solution from the ion exchange chromatographic resin of step (xi) using a gradient solvent solution and collecting the gradient elution fractions; and
  (xiv) removing the gradient elution solution from the produced fractions of step (xiii) to produce purified and substantially purified extract.

In alternative embodiments, a "substantially pure" preparation of cannabinoid is defined as a preparation having a chromatographic purity (of the desired cannabinoid or cannabinoid acid) of greater than about 75%, or greater than about 96%, or greater than about 97%, or greater than about 98%, or greater than about 99%, or greater than about 99.5%, or between about 70% and 99.9%, as determined by area normalization of an HPLC profile.

In alternative embodiments, the term "product enriched in a given cannabinoid" encompasses preparations having at least about 50%, or greater than about 75%, or greater than about 90%, 95% or 98%, or between about 50% and 99.9%, chromatographic purity, for the desired cannabinoid.

In alternative embodiments, a non-purified, or non-substantially purified, product can comprise a greater proportion of impurities, non-target materials and/or other cannabinoids than a "substantially pure" preparation. The cannabinoid can be (e.g., a cannabinoid purified or isolated by, or made by a reaction of, a method as provided herein can be): $\Delta^9$tetrahydrocannabinol ($\Delta^9$ THC); cannabidiol (CBD); cannabinol (CBN); cannabigerol (CBG); cannabichromene (CBC); cannabidivarol (CBDV); tetra-hydrocannabidiol (THCBD); tetra-hydrocannabigerol (THCBG); tetra-hydrocannabichromene (THCBC); or, tetra-hydrocannabidivarol (THCBDV); the carboxylic acid precursors of the foregoing compounds; and related naturally occurring compounds and their derivatives.

In alternative embodiments, the term "cannabinoids" e.g., a cannabinoid purified or isolated by, or made by a reaction of a process as provided herein, includes or refers to a family of natural products that can contain a 1,1'-di-methyl-pyrane ring, a variedly derivatized aromatic ring and/or a variedly unsaturated cyclohexyl ring and their immediate chemical precursors.

In alternative embodiments, the term "cannflavins", e.g., a cannflavin purified or isolated by, or made by a reaction of a process as provided herein, includes or refers to a family of natural products that can contain a 1,4-pyrone ring fused to a variedly derivatized aromatic ring and linked to a second variedly derivatized aromatic ring.

In alternative embodiments, the term "essential oils", e.g., an essential oil used as a starting material in a process as provided herein, or an essential oil that may be isolated by a process as provided herein, includes or refers to a family of natural products that can contain a multiple of the 5-membered isoprene unit variedly substituted, often cyclized to form one or more ring systems; they may also contain series of aldehydes and/or ketones and esters of a variety of carboxylic acid substituted compounds.

In alternative embodiments, provided are methods for extracting and/or purifying cannabinoids from any plant or microbial material extract known to contain such cannabinoids, cannflavins and essential oils; and, optionally to purify cannflavins and to optionally purify essential oils. In alternative embodiments, the extract is passed through a series of chromatographic columns, for example, a normal phase column, a reversed phase column or an ion exchange column as a continuous simulated moving bed (SMB) configuration.

In one embodiment, the chromatographic column is arranged for gradient elution fractioning using normal phase, reverse phase and/or ion exchange chromatography. In one embodiment $\Delta^9$-THC and CBD are fractionated out of the eluent. For example, in one embodiment, as the extract is passed over the column, $\Delta^9$-THC and CBD is differentially retained or detained (e.g., reversibly bound) on the column. As a result, as the extract comes off the column, the initial fractions eluted off the column will be (substantially) free of $\Delta^9$-THC and CBD. The fractions free of $\Delta^9$-THC and CBD are pooled, thereby producing an extract with $\Delta^9$-THC and CBD substantially removed (e.g., in alternative embodiments, "substantially removed" or "substantially fractionated" means at least 85%, 90%, 95%, 98%, 99% or 99.5% or more removed or fractionated).

In some embodiments, (substantially) only $\Delta^9$-THC is substantially fractionated out of the eluent. For example, in one embodiment, as the extract or pooled fractions from a previous normal phase, reverse phase and/or ion exchange elution are passed over the column, $\Delta^9$-THC is differentially retained or detained (e.g., reversibly bound) on the column. As a result, as the extracts are pooled previous elution fractions comes off the column, the initial fractions eluted off the column will be free of $\Delta^9$-THC. These fractions free of $\Delta^9$-THC are pooled, thereby producing an extract with $\Delta^9$-THC substantially removed (e.g., in alternative embodiments, "substantially removed" or "substantially fractionated" means at least 85%, 90%, 95%, 98%, 99% or 99.5% or more removed or fractionated).

In some embodiments, when using a continuous chromatography apparatus or device, a series of columns are arranged for example 3, 4, 5, 6, 7, 8 or more, or between 3 and 30 or more, columns are arranged in a continuous rotation traveling through a series of contact points where gradient elution solutions and extract solution are introduced at fixed points for a period of time allowing for continuous loading and elution, and collection of fractions. The first column is loaded with extract solution at the first position (or station). The first column is then moved to the second position where the first gradient elution is introduced (or loaded) while at the same time the second column is loaded with extract solution at position one. The first column then rotates (i.e., is moved) to the third position where the second gradient solvent is introduced, the second column moves to the second position where the first gradient solvent is introduced and the third column is loaded with extract solution at position one. The first column then moves to the fourth position where the third gradient solvent is introduced, the second column moves to the third position where the second gradient solvent is introduced, the third column moves to the second position where the first gradient solvent is introduced and the fourth column is loaded with extract solution at position one. The first column then moves to the fifth position where the fourth gradient solvent is introduced, the second column moves to the fourth position where the third gradient solvent is introduced, the third column moves to the third position where the second gradient is introduced, the fourth column moves to the second position where the first gradient solvent is introduced and the fifth column is loaded with extract solution at position one. The first column then moves to the sixth position where the fifth gradient solvent is introduced, the second column moves to the fifth position where the fourth gradient is introduced, the third column moves to the fourth position where the third gradient solvent is introduced, the fourth column moves to the third position where the second gradient solvent is introduced, the fifth column moves to the second position where the first gradient solvent is introduced and the sixth column is loaded with extract solution at position one. The first column then moves or returns to the first position where extract solution is loaded, the second column moves to the sixth position where the fifth gradient solvent is introduced, the third column moves to the fifth position where the fourth gradient solvent is introduced, the fourth column moves to the fourth position where the third gradient solvent is introduced, the fifth column moves to the third position where the second gradient solvent is introduced and the sixth column moves to the second position where the first gradient solvent is introduced. The equipment is generally described in U.S. Pat. Nos. 4,764,276, 4,808,317, and 4,710,364, for example, each of which are expressly incorporated herein by reference.

In a particular embodiment the first gradient solvent elutes CBD, CBG and CBN and is substantially fractionated in the eluent. For example, in one embodiment, as the extract or pooled fractions from a normal phase, reverse phase and/or ion exchange elution are passed over the column, CBD, CBG and CBN is differentially produced in the eluent (e.g., by use of a gradient elution process). In a particular embodiment second gradient solvent elutes CBD and is substantially fractionated in the eluent. For example, in one embodiment, as the extract or pooled fractions from a normal phase, reverse phase and/or ion exchange elution are passed over the column, CBD is differentially produced in the eluent. In a particular embodiment the third gradient solvent elutes CBD and $\Delta^9$-THC and is substantially fractionated in the eluent. For example, in one embodiment, as the extract or pooled fractions from a normal phase, reverse phase and/or ion exchange elution are passed over the column, CBD and $\Delta^9$-THC is differentially produced in the eluent. In a particular embodiment the fourth gradient elutes $\Delta^9$-THC and is substantially fractionated in the eluent. For example, in one embodiment, as the extract or pooled fractions from a normal phase, reverse phase and/or ion exchange elution are passed over the column, $\Delta^9$-THC is differentially produced in the eluent. In a particular embodiment the fifth gradient elutes CBC, THC-A, terpenes and $\Delta^9$-THC and is substantially fractionated in the eluent. For example, in one embodiment, as the extract or pooled fractions from a normal phase, reverse phase and/or ion exchange elution are passed over the column, CBC, THC-A, terpenes and $\Delta^9$-THC is differentially produced in the eluent.

In some embodiments the fractions each produced fraction from the first continuous gradient elution separation is collected and the elution solution is removed. The collected fraction of cannabinoids is then loaded onto a normal phase, reverse phase or ion exchange resin and subject to the before mentioned continuous chromatography method to either preferentially purify a specific target cannabinoid from minor cannabinoids contained in the collected fraction.

In some embodiments, (substantially) only CBD is substantially fractionated out of the eluent. For example, in one embodiment, as the extract or pooled fractions from a previous normal phase, reverse phase and/or ion exchange elution are passed over the column, CBD is differentially retained or detained (e.g., reversibly bound) on the column. As a result, as the extract or pooled previous elution fractions comes off the column, the initial fractions eluted off the column will be (substantially) free of CBD. These fractions free of CBD are pooled, thereby producing an extract with CBD substantially removed (e.g., in alternative embodiments, "substantially removed" or "substantially fractionated" means at least 85%, 90%, 95%, 98%, 99% or 99.5% or more removed or fractionated).

In some embodiments, $\Delta^9$-THC carboxylic acid species or $\Delta^9$-THCA and CBD carboxylic acid species CBDA are fractionated out of out of the eluent. For example, in one embodiment, as the extract or pooled fractions from a first elution are passed over the column, $\Delta^9$-THCA and CBDA are differentially retained or detained (e.g., reversibly bound) on the column. As a result, as the extract or pooled first elution fractions comes off the column, the initial fractions eluted off the column will be (substantially) free of $\Delta^9$-THCA and CBDA. These fractions (substantially) free of $\Delta^9$-THCA and CBDA are pooled, thereby producing an extract with $\Delta^9$-THCA and CBDA substantially removed (e.g., in alternative embodiments, "substantially removed" or "substantially fractionated" means at least 85%, 90%, 95%, 98%, 99% or 99.5% or more removed or fractionated).

In some embodiments, the $\Delta^9$-THC may be eluted from the column, extracted or concentrated, for purifying, or substantially purifying, $\Delta^9$-THC. In alternative embodiments, the chromatographic column is arranged for continuous fractionation of a specific cannabinoid or groups of cannabinoids or their carboxylic acid species, cannflavin or essential oil or class of cannabinoids, cannflavins or essential oils out of the eluent, for example, cannabidiol (CBD), cannabinol (CBN), cannabigerol (CBG), cannabichromene (CBC), cannabidivarol (CBDV), tetrahydrocannabidiol (THCBD), tetrahydrocannabigerol (THCBG), tetrahydrocannabichromene (THCBC), tetrahydrocannabidivarol (THCBDV), $\Delta^8$-THC, the carboxylic acid precursors of the foregoing compounds, and related naturally occurring compounds and their derivatives. In alternate embodiments, the chromatographic column is arranged for continuous fractionation cannflavins and related naturally occurring compounds and their derivatives. In alternate embodiments, the system is arranged to continuously fractionate the components of essential oils. The list of compounds provided herein is not exhaustive and is in no way intended to be limiting. In these embodiments, the compound(s) of interest are retained or detained (e.g., reversibly bound) on the column so that fractions (alternatively, the last fractions) of the extract eluted from the column contain the compounds(s) of interest. In alternative embodiments, fractions containing the compound(s) of interest are pooled. In some embodiments, different compounds may be extracted with different solvents and then combined into a single extract. As will be appreciated by one knowledgeable in the art, in this manner, several different cannabinoids could be purified from a single extract.

In alternative embodiments, the "plant material or microbial" will be derived from one or more cannabis or hemp plants, or from other plants, or from a microbial species, including fungi, lichen, yeast and bacteria. The term "plant material" encompasses a plant or plant part (e.g. bark, wood, leaves, stems, roots, flowers, fruits, seeds, berries or parts thereof) as well as exudates, and includes material falling within the definition of "botanical raw material" in the Guidance for Industry Botanical Drug Products Draft Guidance, August 2000, US Department of Health and Human Services, Food and Drug Administration Centre for Drug Evaluation and Research. The term "cannabis plant(s)" encompasses wild type *Cannabis sativa* and also variants thereof, including *Cannabis* chemovars (varieties characterized by virtue of chemical composition) which naturally contain different amounts of the individual cannabinoids, also *Cannabis sativa* subspecies *indica* including the variants var. *indica* and var. *kafiristanica*, *Cannabis indica* and also plants which are the result of genetic crosses, self-crosses or hybrids thereof. The term "*Cannabis* plant material" also can encompass plant material derived from one or more cannabis plants, and can comprise any "cannabis plant material" including, e.g., herbal *Cannabis* and dried *Cannabis* biomass. The term "*Cannabis* plant material" also can encompass "decarboxylated *Cannabis* plant material", which refers to *Cannabis* plant material which has been subject to a decarboxylation step in order to convert cannabinoid acids to the corresponding free cannabinoids.

In alternative embodiments, a starting material for a purification process as provided herein is an extract solution containing a cannabinoid or cannabinoid acid obtained from a natural or a synthetic source, e.g., a plant or microbial material. In alternative embodiments, the "extract solution containing a cannabinoid or cannabinoid acid" comprises a solvent extract of a plant or microbial material. Solvents used for extraction for use in the preparation of extract solutions can comprise non-polar solvents, polar solvents such as ethanol, methanol or water, or organic solvents such as liquid carbon dioxide, and combinations thereof. The solvent may be an organic solvent, selected from the group consisting of: non-polar solvents include liquid non-polar solvents comprising lower C1-C12, for example, C3 to C8, or straight chain or branched chain alkanes for example, methane, ethane, propane, butane, pentane, toluene, trimethylpentane; a low molecular weight alcohol, polar solvents consisting of for example, ethanol, methanol, water; a low molecular weight chlorinated hydrocarbon, for example, chloroform and dichloromethane; or a supercritical fluid such as $CO_2$ with or without an organic solvent modifier.

In alternative embodiments, the extract is prepared by dissolving or partially dissolving the natural or synthetic, or the plant or microbial material in a solvent, removing insoluble material from the resultant solution (optionally by filtration with or without activated carbon, precipitation, centrifugation and the like), and optionally removing some or all of the extraction solvent from the solution (optionally by rotary evaporation) to form an extract or extract solution or concentrate containing a cannabinoid or cannabinoid acid.

In alternative embodiments, extractions can comprise using a technique referred to as accelerated solvent extraction or may use subcritical water or any combination of water and solvent. In one embodiment, when isolating cannabinoid acids, a modified pH gradient elution solution is used. The primary purpose of this pH adjustment (the modified pH gradient) is to promote or prevent ionization of the cannabinoid acid. pH modified gradient elution solutions may be achieved by the additional of a small volume of acid or base to the solvent. It may be sufficient to add a relatively weak acid, such as acetic acid, oxalic acid, glycolic acid, carbonic acid or ammonium hydroxide or a small amount of base or buffering agent such as sodium hydroxide, magnesium hydroxide, sodium carbonate or sodium bicarbonate. For any given purification process the optimal amount and type of acid or base used may be determined empirically. An alternative exemplary acidified solvent is 0.1% acetic acid in ethanol or 0.1% sodium hydroxide in ethanol. In alternative embodiments, the neutralizing agent consists of for example sodium hydroxide, sodium carbonate, potassium carbonate, and potassium t-amylate, sodium bicarbonate.

Acidified non-polar and polar solvents of the types described above can be useful in preparation of gradient elutions using ion exchange chromatography. The solvents used in the conversion can comprise an organic solvent, e.g., a non-polar solvent, including a liquid non-polar solvent comprising lower C1-C12, or C3 to C8, straight chain or branched chain alkanes for example, methane, ethane, propane, butane, pentane, toluene, trimethylpentane, hexane; a low molecular weight alcohol, polar solvents consisting of for example, ethanol; a low molecular weight chlorinated hydrocarbon, for example, chloroform and dichloromethane; a heterocyclic compound or cyclic ether for example, tetrahydrofuran and 2-Methyltetrahydrofuran and aromatic ring hydrocarbons such as benzene, toluene, xylene and ethylbenzene.

In alternative embodiments, the plant or microbial material is subjected to a decarboxylation step prior to solvent extraction. The purpose of the decarboxylation step is to convert cannabinoid acids present in the plant or microbial material to the corresponding free cannabinoids. In alternative embodiments, the decarboxylation is carried out by heating the plant or microbial material to a defined temperature for a suitable length of time. Decarboxylation of cannabinoid acids is a function of time and temperature, thus at higher temperatures a shorter period of time will be taken for complete decarboxylation of a given amount of cannabinoid acid. In alternative embodiments selecting appropriate conditions for decarboxylation consideration include minimizing thermal degradation of the desirable, pharmacological cannabinoids into undesirable degradation products, particularly thermal degradation of $\Delta^9$-THC. In alternative embodiments, the decarboxylation is carried out in a multi-step heating process in which the plant or microbial material is: i) heated to a first temperature for a first (relatively short) time period to evaporate off retained water and allow for uniform heating of the plant or microbial material; and ii) the temperature is increased to a second temperature for a second time period (typically longer than the first time period) until at least 95% conversion of the acid cannabinoids to their neutral form has occurred.

In alternative embodiments, the "extract containing a cannabinoid or a cannabinoid acid" prepared from the starting plant or microbial material comprises a "botanical drug substance" prepared from the plant or microbial material, or a polar or non-polar solvent solution of such a botanical drug substance. In the context of this application a "botanical drug substance" is an extract derived from plant or microbial material, which extract fulfills the definition of "botanical drug substance" provided in the Guidance for Industry Botanical Drug Products Draft Guidance, August 2000, US Department of Health and Human Services, Food and Drug Administration Centre for Drug Evaluation and Research of: "A drug substance derived from one or more plants, algae, or macroscopic fungi. It is prepared from botanical raw materials by one or more of the following processes: pulverization, decoction, expression, aqueous extraction, ethanolic extraction, or other similar processes." "Botanical drug substances" derived from cannabis plants include primary extracts prepared by such processes as, for example, maceration, percolation, and solvent extraction.

In alternative embodiments, solvent extraction may be carried out using essentially any solvent that dissolves, or substantially dissolves, cannabinoids/cannabinoid acids, such as for example C1 to C5 alcohols (e.g. ethanol, methanol), C5-C12 alkanes (e.g. hexane), norflurane, or 1,1,1,2-tetrafluoroethane (HFA134a), 1,1,1,2,3,3,3-Heptafluoropropane (or HFA227), chloroform, dichloromethane, dichloroethane and carbon dioxide. When solvents such as those listed above are used, the resultant extract typically contains non-specific lipid-soluble material. This can optionally be removed by a variety of processes including filtration to remove solids, "winterization", which involves for example chilling to −20° C. or lower followed by filtration to remove waxy ballast, extraction with liquid carbon dioxide and by distillation.

In alternative embodiments, any protocol for the preparation of botanical drug substances from cannabis and hemp plant material can be used, e.g., as described in International patent application WO 02/064109. In alternative embodiments, the botanical drug substance is obtained by carbon dioxide ($CO_2$) extraction, polar solvent extraction or non-polar solvent extraction or combinations thereof followed by a filtration. Optionally a secondary extraction is performed to remove a substantial proportion of non-cannabinoid materials, e.g. waxes, wax esters and glycerides, unsaturated fatty acid residues, terpenes, carotenes, and flavonoids and other ballast.

In alternative embodiments, if it is intended to prepare free cannabinoids from the plant or microbial material (e.g., cannabis), then the material is heated to a defined temperature for a defined period of time in order to partially or substantially decarboxylate cannabinoid acids to free cannabinoids prior to extraction of the botanical drug substance. In alternative embodiments, the botanical drug substance is prepared according to a process comprising the following steps: i) optional decarboxylation of the plant material, ii) extraction with polar or non-polar solvent, to produce a crude botanical drug substance, iii) optional precipitation with C1-C5 alcohol to reduce the proportion of non-target materials, iv) removing the precipitate (for example, by filtration, precipitation, centrifugation and the like), v) optional treatment with activated charcoal, and vi) evaporation to remove C1-C5 alcohol and water, thereby producing a final botanical drug substance.

In alternative embodiments, the tetrahydrocannabinol at therapeutically effective concentrations or dosages is combined with a pharmaceutically or pharmacologically acceptable carrier, excipient or diluent, either biodegradable or non-biodegradable. Exemplary examples of carriers include, but are by no means limited to, for example, poly(ethylene-vinyl acetate), copolymers of lactic acid and glycolic acid, poly(lactic acid), gelatin, collagen matrices, polysaccharides, poly(D,L lactide), poly(malic acid), poly(caprolactone), celluloses, albumin, starch, casein, dextran, polyesters, ethanol, methacrylate, polyurethane, polyethylene, vinyl polymers, glycols, mixtures thereof and the like. Standard excipients that can be used include gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethycellulose phthalate, non-crystalline cellulose, magnesium aluminum silicate, triethanolamine, polyvinyl alcohol, polyvinylpyrrolidone, sugars and starches. See, for example, Remington: The Science and Practice of Pharmacy, 1995, Gennaro ed.

In alternative embodiments, purity is determined by Gas Chromatography-Mass Spectrometry (GC-MS) and/or by analytical high-performance liquid chromatography (HPLC). The total ion chromatogram from the GC-MS gives information similar to that provided by a flame ionization detector (FID)-GC in that the peak area is proportional to the mass of the analytes detected. Total peak area and the peak areas of the individual analytes can be compared in the GC-MS case as long as the masses are in generally the same range. As discussed below, in some embodiments, purity of the isolated cannabinoids by the continuous process is greater than about 90%, 95%, 97% or 98%, or purity is greater that about 98% to 99%.

Chapter V In alternative embodiments, provided are continuous isolation and purification processes for preparing a substantially pure cannabidiol or a product enriched in cannabidiol from plant material extracts. In alternative embodiments, provided herein are improved methods for converting cannabidiol (CBD) to $\Delta^8$-THC and $\Delta^9$-THC, including a purification and conversion process based on a simple combination of continuous chromato-graphic gradient elutions and semi continuous isomerization reactions. This exemplary process is simple, efficient and economic.

In alternative embodiments, provided are methods of preparing cannabinoids in substantially pure form starting from plant extract material and conversion of the purified CBD to form both $\Delta^8$ THC and $\Delta^9$ THC and subsequent purification of the produced $\Delta^8$ tetrahydrocannabinol ($\Delta^8$ THC) into $\Delta^9$ tetrahydrocannabinol ($\Delta^9$ THC) using continuous chromatography.

In alternative embodiments, provided are processes for producing and isolating cannabinoids from cannabis and hemp extracts which contain cannabinoids in minute amounts. In alternative embodiments, provided are processes for producing and isolating cannabinoids from natural materials, including plant or plant extracts, microbes, or botanical drug substances, or synthetically and semi-synthetically prepared cannabinoid products, or from recombinantly engineered microbes, e.g., yeasts or bacteria recombinantly engineered to express one or more cannabinoids. In one embodiment, exemplary methods are inexpensive and provide specific cannabinoid concentrates (e.g., of CBD, $\Delta^8$-THC, $\Delta^9$-THC) of high purity.

In one embodiment, exemplary methods provide a simple and economical continuous process for separating and concentrating cannabinoids from solvent-extracted cannabinoid containing materials. In one embodiment, exemplary methods provide a method that first converts the substantially isolated CBD into a mixture of $\Delta^8$-THC and $\Delta^9$-THC, and then subsequently purifying or isolating the $\Delta^8$-THC and $\Delta^9$-THC. In alternative embodiments, the solvent-extracted cannabinoid containing materials are derived from synthetic or biological materials such as hemp and *Cannabis* or botanical drug substances, or from microbial materials; and the solvent extraction methods can be polar solvent extractions, nonpolar solvent extractions, or the solvent extraction methods can comprise use of super critical carbon dioxide or mixtures thereof. The solvent extraction methods can extract cannabinoids substantially from the synthetic or biological, e.g., plant, matter, along with other plant matter comprising lipids, waxes, monoterpenes, sesquiterpenes, hydrocarbons, alkaloids, flavonoids and chlorophylls.

In alternative embodiments, methods provided herein comprise subjecting cannabinoid containing solvent extract starting materials to a number of chromatographic resins in various contacting steps using various gradient elution solutions.

In alternative embodiments, the cannabinoids which can be fractionated and isolated using methods as provided herein, or which can be produced in reactions as provided herein, or from which the solvent extracts are derived can be from, or can comprise: $\Delta^8$tetrahydrocannabinol ($\Delta^8$ THC); $\Delta^9$tetrahydrocannabinol ($\Delta^9$ THC); cannabidiol (CBD); cannabinol (CBN); cannabigerol (CBG); cannabichromene (CBC); cannabidivarol (CBDV); tetrahydrocannabidiol (THCBD); tetrahydrocannabigerol (THCBG); tetrahydrocannabichromene (THCBC); tetrahydrocannabidivarol (THCBDV), or combinations thereof, including carboxylic acid precursors of the foregoing compounds and related naturally occurring compounds and their derivatives.

In alternative embodiments, provides are methods of preparing or obtaining a substantially pure cannabinoid or a product enriched in a given cannabinoid comprising:
(i) obtaining or providing, or having provided, an extract or extract solution, or an aliquot or sample, containing a cannabinoid or a cannabinoid acid from a natural or the synthetic source, e.g., a plant material;
(ii) optionally filtering the extract or extract solution, or aliquot or sample, of step (i) to remove solids and color bodies;
(iii) optionally removing the extract solvent (as an extract fraction);
(iv) continuously loading of an amount of extract solution over a defined time increment over multiple stationary phase resins columns such as a normal phase, reverse phase and/or ion exchange chromatographic resin;
(v) continuously eluting the extract, or extract solution, or aliquot or sample, solution using multiple defined gradient elution solutions at specific time increments and volumes;
(vi) continuously collecting the gradient elution fractions;
(vii) removing the gradient elution solution from the produced fractions to generate a substantially purified extract, or a substantially purified extract from each fraction;
(viii) optionally loading of specific first gradient elution fractions on a reverse phase, ion exchange or normal chromatographic resin;
(ix) continuously eluting the first gradient elution fractions with a second gradient elution solvent; and,
(x) removing of the second gradient elution solvent from the produced fractions to produce a purified extract, or a substantially purified extract from each fraction.

In alternative embodiments, the methods further comprise:
a step (xi): loading of first and second gradient elution solvents s onto an ion exchange chromatographic resin;

a step (xii): eluting an extract solution from the ion exchange chromatographic resin of step (x) using a gradient solvent solution and collecting the gradient elution fractions; and (xiii) removing the gradient elution solution from the produced fractions of step (xiv) to produce purified and substantially purified extract.

In alternative embodiments, provided are methods of substantially converting CBD to $\Delta^8$ THC and $\Delta^9$ THC comprising:
(a) providing a reaction mixture comprising a catalyst in an organic solvent;
(b) adding CBD material from steps (viii) and steps (xiii), above;
(c) mixing said reaction mixture;
(d) reacting mixture for a period of time at a controlled temperature;
(e) adding a base to the reaction mixture;
(f) allowing the mixture to separate into an aqueous phase and an organic phase;
(g) removing the organic phase; and,
(h) loading the organic phase onto a normal phase chromatography column
(i) eluting the organic phase with an organic solvent and recovering substantially pure CBD, $\Delta^8$ THC and $\Delta^9$ THC
optionally, repeating steps (a) through (i).

In alternative embodiments, a "substantially pure" preparation of cannabinoid is defined as a preparation having a chromatographic purity (of the desired cannabinoid or cannabinoid acid) of greater than about 75%, or greater than about 96%, or greater than about 97%, or greater than about 98%, or greater than about 99%, or greater than about 99.5%, or between about 70% and 99.9%, as determined by area normalisation of an HPLC profile.

In alternative embodiments, the term "product enriched in a given cannabinoid" encompasses preparations having at least about 50%, or greater than about 75%, or greater than about 90%, 95% or 98%, or between about 50% and 99.9%, chromatographic purity, for the desired cannabinoid.

In alternative embodiments, the term "about" is within 20% of the stated value, or 19%, or 18%, or 17%, or 16%, or 15%, or 14%, or 13%, or 12%, or 11%, or 10%, or 9%, or 8%, or 7%, or 6%, or 5%, or 4%, or 3%, or 2%, or 1%, or 0.5%, or 0.1%, or 0.05%, or 0.01%, or is between 20% and 0.01% of the stated value.

In alternative embodiments, a non-purified, or non-substantially purified, product can comprise a greater proportion of impurities, non-target materials and/or other cannabinoids than a "substantially pure" preparation. The cannabinoid can be (e.g., a cannabinoid purified or isolated by, or made by a reaction of, a method as provided herein can be): $\Delta^8$tetrahydrocannabinol ($\Delta^8$ THC); $\Delta^9$tetrahydrocannabinol ($\Delta^9$ THC); cannabidiol (CBD); cannabinol (CBN); cannabigerol (CBG);

cannabichromene (CBC); cannabidivarol (CBDV); tetra-hydrocannabidiol (THCBD); tetra-hydrocannabigerol (THCBG); tetra-hydrocannabichromene (THCBC); or, tetra-hydrocannabidivarol (THCBDV); the carboxylic acid precursors of the foregoing compounds; and related naturally occurring compounds and their derivatives.

In alternative embodiments, the term "cannabinoids" e.g., a cannabinoid purified or isolated by, or made by a reaction of a process as provided herein, includes or refers to a family of natural products that can contain a 1,1'-di-methyl-pyrane ring, a variedly derivatized aromatic ring and/or a variedly unsaturated cyclohexyl ring and their immediate chemical precursors.

In alternative embodiments, the term "cannflavins", e.g., a cannflavin purified or isolated by, or made by a reaction of a process as provided herein, includes or refers to a family of natural products that can contain a 1,4-pyrone ring fused to a variedly derivatized aromatic ring and linked to a second variedly derivatized aromatic ring.

In alternative embodiments, the term "Lewis acid" refers to a powerful electron pair acceptor; and examples include but are by no means limited to $BF_3Et_2O$ (boron trifluoride ditheyl etherate), p-toluenesulfonic acid and boron trifluoride.

In alternative embodiments, the term "non-oxidizing acid" refers to hydrobromic, hydrochloric, hydrofluoric, acetic, benzoic, chloroacetic, formic, phosphoric, sulfuric, trifluoroacetic and oxalic acids.

In alternative embodiments, the term "essential oils", e.g., an essential oil used as a starting material in a process as provided herein, or an essential oil that may be isolated by a process as provided herein, includes or refers to a family of natural products that can contain a multiple of the 5-membered isoprene unit variedly substituted, often cyclized to form one or more ring systems; they may also contain series of aldehydes and/or ketones and esters of a variety of carboxylic acid substituted compounds.

In alternative embodiments, provided are methods for extracting and/or purifying cannabinoids from any plant material extract known to contain such cannabinoids, cannflavins and essential oils; and, optionally to purify cannflavins and to optionally purify essential oils. In alternative embodiments, the extract is passed through a series of chromatographic columns, for example, a normal phase column, a reversed phase column or an ion exchange column as a continuous simulated moving bed (SMB) configuration.

In one embodiment, the chromatographic column is arranged for gradient elution fractioning using normal phase, reverse phase and/or ion exchange chromatography. In one embodiment $\Delta^9$-THC and CBD are fractionated out of the eluent. For example, in one embodiment, as the extract is passed over the column, $\Delta^9$-THC and CBD is differentially retained or detained (e.g., reversibly bound) on the column. As a result, as the extract comes off the column after gradient elution transition, the initial fractions eluted off the column will be (substantially) free of $\Delta^9$-THC and CBD. The fractions free of $\Delta^9$-THC and CBD are pooled, thereby producing an extract with $\Delta^9$-THC and CBD substantially removed (e.g., in alternative embodiments, "substantially removed" or "substantially fractionated" means at least 85%, 90%, 95%, 98%, 99% or 99.5% or more removed or fractionated).

In some embodiments, (substantially) only $\Delta^9$-THC is substantially fractionated out of the eluent. For example, in one embodiment, as the extract or pooled fractions from a previous normal phase, reverse phase and/or ion exchange elution are passed over the column, $\Delta^9$-THC is differentially retained or detained (e.g., reversibly bound) on the column. As the extracts pooled from previous elution fractions come off the column, the initial fractions eluted off the column will be free of $\Delta^9$-THC. These fractions free of $\Delta^9$-THC are pooled, thereby producing an extract with $\Delta^9$-THC substantially removed (e.g., in alternative embodiments, "substantially removed" or "substantially fractionated" means at least 85%, 90%, 95%, 98%, 99% or 99.5% or more removed or fractionated).

In some embodiments, when using a continuous chromatography apparatus or device, a series of columns are arranged, for example, 3, 4, 5, 6, 7, 8, 9, or 10 or more, or between 3 and 30, columns are arranged in a continuous rotation traveling through a series of contact points where gradient elution solutions and extract solution are introduced at fixed points for a period of time allowing for continuous loading and elution, and collection of fractions. The first column is loaded with extract solution at the first position (or station). The first column is then moved to the second position where the first gradient elution is introduced (or loaded) while at the same time the second column is loaded with extract solution at position one. The first column then rotates (i.e., is moved) to the third position where the second gradient solvent is introduced, the second column moves to the second position where the first gradient solvent is introduced and the third column is loaded with extract solution at position one. The first column then moves to the fourth position where the third gradient solvent is introduced, the second column moves to the third position where the second gradient solvent is introduced, the third column moves to the second position where the first gradient solvent is introduced and the fourth column is loaded with extract solution at position one. The first column then moves to the fifth position where the fourth gradient solvent is introduced, the second column moves to the fourth position where the third gradient solvent is introduced, the third column moves to the third position where the second gradient solvent is introduced, the fourth column moves to the second position where the first gradient solvent is introduced and the fifth column is loaded with extract solution at position one. The first column then moves to the sixth position where the fifth gradient solvent n is introduced, the second column moves to the fifth position where the fourth gradient solvent is introduced, the third column moves to the fourth position where the third gradient solvent is introduced, the fourth column moves to the third position where the second gradient solvent is introduced, the fifth column moves to the second position where the first gradient solvent is introduced and the sixth column is loaded with extract solution at position one. The first column then moves or returns to the first position where extract solution is loaded, the second column moves to the sixth position where the fifth gradient solvent is introduced, the third column moves to the fifth position where the fourth gradient solvent is introduced, the fourth column moves to the fourth position where the third gradient solvent is introduced, the fifth column moves to the third position where the second gradient solvent is introduced and the sixth column moves to the second position where the first gradient solvent is introduced. In a particular embodiment the first gradient solvent elutes CBD, CBG and CBN and is substantially fractionated in the eluent. For example, in one embodiment, as the extract or pooled fractions from a normal phase, reverse phase and/or ion exchange elution are passed over the column, CBD, CBG and CBN is differentially produced in the eluent (e.g., by use of a gradient elution process). In a particular embodiment second gradient solvent elutes CBD and is substantially fractionated in the eluent. For example, in one embodiment, as the extract or pooled fractions from a normal phase, reverse phase and/or ion exchange elution are passed over the column, CBD is differentially produced in the eluent. In a particular embodiment the third gradient solvent elutes CBD and $\Delta^9$-THC and is substantially fractionated in the eluent. For example, in one embodiment, as the extract or pooled fractions from a normal phase, reverse phase and/or ion exchange elution are passed over the column, CBD and $\Delta^9$-THC is differentially produced in the eluent. In a particular embodiment the fourth gradient elutes $\Delta^9$-THC and is substantially fractionated in the eluent. For example, in one embodiment, as the extract or pooled fractions from a normal phase, reverse phase and/or ion exchange elution are passed over the column, $\Delta^9$-THC is differentially produced in the eluent. In a particular embodiment the fifth gradient elutes CBC, THC-A, terpenes and $\Delta^9$-THC and is substantially fractionated in the eluent. For example, in one embodiment, as the extract or pooled fractions from a normal phase, reverse phase and/or ion exchange elution are passed over the column, CBC, THC-A, terpenes and $\Delta^9$-THC is differentially produced in the eluent.

In some embodiments, when using a continuous chromatography apparatus or device, a series of columns are arranged, for example, 3, 4, 5, 6, 7, 8, 9, or 10 or more, or between 3 and 30, columns are arranged in a continuous rotation traveling through a series of contact points where gradient elution solutions and extract solution are introduced at fixed points for a period of time allowing for continuous loading and elution, and collection of fractions. The first column is loaded with extract solution at the first position (or station). The first column is then moved to the second position where the first gradient elution is introduced (or loaded) while at the same time the second column is loaded with extract solution at position one. The first column then rotates (i.e., is moved) to the third position where the second gradient solvent is introduced, the second column moves to the second position where the first gradient solvent is introduced and the third column is loaded with extract solution at position one. The first column then moves to the fourth position where the third gradient solvent is introduced, the second column moves to the third position where the second gradient solvent is introduced, the third column moves to the second position where the first gradient solvent is introduced and the fourth column is loaded with extract solution at position one. The first column then moves to the fifth position where the fourth gradient solvent is introduced, the second column moves to the fourth position where the third gradient solvent is introduced, the third column moves to the third position where the second gradient solvent is introduced, the fourth column moves to the second position where the first gradient solvent is introduced and the fifth column is loaded with extract solution at position one. The first column then moves to the sixth position where the fifth gradient solvent is introduced, the second column moves to the fifth position where the fourth gradient solvent is introduced, the third column moves to the fourth position where the third gradient solvent is introduced, the fourth column moves to the third position where the second gradient solvent is introduced, the fifth column moves to the second position where the first gradient solvent is introduced and the sixth column is loaded with extract solution at position one. The first column then moves or returns to the first position where extract solution is loaded, the second column moves to the sixth position where the fifth gradient solvent is introduced, the third column moves to the fifth position where the fourth gradient solvent is introduced, the fourth column moves to the fourth position where the third gradient solvent is introduced, the fifth column moves to the third position where the second gradient solvent is introduced and the sixth column moves to the second position where the first gradient solvent is introduced.

In a particular embodiment the first gradient solvent elutes CBD, CBG and CBN and is substantially fractionated in the eluent. For example, in one embodiment, as the extract or pooled fractions from a normal phase, reverse phase and/or ion exchange elution are passed over the column, CBD, CBG and CBN is differentially produced in the eluent (e.g., by use of a gradient elution process). In a particular embodiment second gradient solvent elutes CBD and is substantially fractionated in the eluent. For example, in one embodiment, as the extract or pooled fractions from a normal phase, reverse phase and/or ion exchange elution are passed over the column, CBD is differentially produced in the eluent. In a particular embodiment the third gradient solvent elutes CBD and $\Delta^9$-THC and is substantially fractionated in the eluent. For example, in one embodiment, as the extract or pooled fractions from a normal phase, reverse phase and/or ion exchange elution are passed over the column, CBD and $\Delta^9$-THC is differentially produced in the eluent. In a particular embodiment the fourth gradient elutes $\Delta^9$-THC and is substantially fractionated in the eluent. For example, in one embodiment, as the extract or pooled fractions from a normal phase, reverse phase and/or ion exchange elution are passed over the column, $\Delta^9$-THC is differentially produced in the eluent. In a particular embodiment the fifth gradient solvent elutes CBC, THC-A, terpenes and $\Delta^9$-THC and is substantially fractionated in the eluent. For example, in one embodiment, as the extract or pooled fractions from a normal phase, reverse phase and/or ion exchange elution are passed over the column, CBC, THC-A, terpenes and $\Delta^9$-THC is differentially produced in the eluent. The second gradient solvent containing CBD is combined with a Lewis acid or non-oxidizing acid catalyst, optionally additional CBD or substantially pure CBD and/or ($\Delta$8-THC) and/or $\Delta$9-tetrahydrocannabinol ($\Delta$9-THC) can be added to the reaction mixture, mixing said reaction mixture for a period of time; adding a neutralizing agent to said mixture; filtration of catalyst and neutralizing agent from mixture; optionally allowing mixture to separate into an aqueous and organic phase; optionally adding organic phase to a chromatography column and eluting the ($\Delta$8-THC) and/or $\Delta$9-tetrahydrocannabinol ($\Delta$9-THC) from the organic phase. The tetrahydrocannabinol may then be combined with suitable excipients known in the art, thereby forming a pharmaceutical composition. In one embodiment, the mixture is allowed to separate into an aqueous phase and an organic phase; and optionally the process further comprises removing the organic phase.

In some embodiments, (substantially) only CBD is substantially fractionated out of the eluent. For example, in one embodiment, as the extract or pooled fractions from a previous normal phase, reverse phase and/or ion exchange elution are passed over the column, CBD is differentially retained or detained (e.g., reversibly bound) on the column. As a result, as the extract or pooled previous elution fractions comes off the column, the initial fractions eluted off the column will be (substantially) free of CBD. These fractions free of CBD are pooled, thereby producing an extract with CBD substantially removed (e.g., in alternative embodiments, "substantially removed" or "substantially fractionated" means at least 85%, 90%, 95%, 98%, 99% or 99.5% or more removed or fractionated).

In some embodiments, $\Delta^9$-THC carboxylic acid species or $\Delta^9$-THCA and CBD carboxylic acid species CBDA are fractionated out of out of the eluent. For example, in one embodiment, as the extract or pooled fractions from a first elution are passed over the column, $\Delta^9$-THCA and CBDA are differentially retained or detained (e.g., reversibly bound) on the column. As a result, as the extract or pooled first elution fractions comes off the column, the initial fractions eluted off the column will be (substantially) free of $\Delta^9$-THCA and CBDA. These fractions (substantially) free of $\Delta^9$-THCA and CBDA are pooled, thereby producing an extract with $\Delta^9$-THCA and CBDA substantially removed (e.g., in alternative embodiments, "substantially removed" or "substantially fractionated" means at least 85%, 90%, 95%, 98%, 99% or 99.5% or more removed or fractionated).

In some embodiments, the $\Delta^9$-THC may be eluted from the column, extracted or concentrated, for purifying, or substantially purifying, $\Delta^9$-THC. In alternative embodiments, the chromatographic column is arranged for fractionating (e.g., sequentially fractionating) a specific cannabinoid or groups of cannabinoids or their carboxylic acid species, cannflavin or essential oil or class of cannabinoids, cannflavins or essential oils out of the eluent, for example, cannabidiol (CBD), cannabinol (CBN), cannabigerol (CBG), cannabichromene (CBC), cannabidivarol (CBDV), tetrahydrocannabidiol (THCBD), tetrahydrocannabigerol (THCBG), tetrahydrocannabichromene (THCBC), tetrahydrocannabidivarol (THCBDV), $\Delta^8$-THC, the carboxylic acid precursors of the foregoing compounds, and related naturally occurring compounds and their derivatives. In alternate embodiments, the chromatographic column is arranged for fractionating (e.g., sequentially fractionating) cannflavins and related naturally occurring compounds and their derivatives. In alternate embodiments, the system is arranged to fractionate the components of essential oils. The list of compounds provided herein is not exhaustive and is in no way intended to be limiting. In these embodiments, the compound(s) of interest are retained or detained (e.g., reversibly bound) on the column so that fractions (alternatively, the last fractions) of the extract eluted from the column contain the compounds(s) of interest. In alternative embodiments, fractions containing the compound(s) of interest are pooled. In some embodiments, different compounds may be extracted with different solvents and then combined into a single extract. As will be appreciated by one knowledgeable in the art, in this manner, several different cannabinoids could be purified from a single extract.

In alternative embodiments, the "plant material" or botanical drug substance is derived from one or more cannabis or hemp plants, or from other plants, or a microbial source, including yeast, bacteria, lichen, algae. The term "plant material" encompasses a plant or plant part (e.g. bark, wood, leaves, stems, roots, flowers, fruits, seeds, berries or parts thereof) as well as exudates, and includes material falling within the definition of "botanical raw material" in the Guidance for Industry Botanical Drug Products Draft Guidance, August 2000, US Department of Health and Human Services, Food and Drug Administration Centre for Drug Evaluation and Research. The term "cannabis plant(s)" encompasses wild type *Cannabis sativa* and also variants thereof, including *Cannabis* chemovars (varieties characterized by virtue of chemical composition) which naturally contain different amounts of the individual cannabinoids, also *Cannabis sativa* subspecies *indica* including the variants var. *indica* and var. *kafiristanica, Cannabis indica* and also plants which are the result of genetic crosses, self-crosses or hybrids thereof. The term "*Cannabis* plant material" also can encompass plant material derived from one or more cannabis plants, and can comprise any "cannabis plant material" including, e.g., herbal *Cannabis* and dried *Cannabis* biomass. The term "*Cannabis* plant material" also can encompass "decarboxylated *Cannabis* plant material", which refers to *Cannabis* plant material which has been subject to a decarboxylation step in order to convert cannabinoid acids to the corresponding free cannabinoids.

In alternative embodiments, a starting material for a purification process as provided herein is an extract solution containing a cannabinoid or cannabinoid acid obtained from a natural or a synthetic source, e.g., a plant or a microbial material. In alternative embodiments, the "extract solution containing a cannabinoid or cannabinoid acid" comprises a solvent extract of a plant material. Solvents used for extraction for use in the preparation of extract solutions can comprise non-polar solvents, polar solvents such as ethanol, methanol or water, or organic solvents such as liquid carbon dioxide, and combinations thereof. The solvent may be an organic solvent, selected from the group consisting of: non-polar solvents include liquid non-polar solvents comprising lower C1-C12, for example, C3 to C8, or straight chain or branched chain alkanes, for example, methane, ethane, propane, butane, pentane, toluene, trimethylpentane; a low molecular weight alcohol, polar solvents comprising, for example, ethanol, methanol, water; a low molecular weight chlorinated hydrocarbon, for example, chloroform and dichloromethane or mixtures thereof; or a supercritical fluid such as $CO_2$ with or without an organic solvent modifier.

In alternative embodiments, the extract is prepared by dissolving or partially dissolving natural or synthetic, or the plant or microbial material, in a solvent, removing insoluble material from the resultant solution (optionally by filtration with or without activated carbon, precipitation, centrifugation and the like), and optionally removing some or all of the extraction solvent from the solution (optionally by evaporation, e.g., rotary evaporation) to form an extract or extract solution or concentrate containing a cannabinoid or cannabinoid acid.

In alternative embodiments, extractions can comprise using a technique referred to as accelerated solvent extraction or may use subcritical water or any combination of water and solvent. In one embodiment, when isolating cannabinoid acids, a modified pH gradient elution solution is used. The primary purpose of this pH adjustment (the modified pH gradient) is to promote or prevent ionization of the cannabinoid acid. pH modified gradient elution solutions may be achieved by the additional of a small volume of acid or base to the solvent. It may be sufficient to add a relatively weak acid, such as acetic acid, oxalic acid, glycolic acid, carbonic acid or ammonium hydroxide or a small amount of base or buffering agent such as sodium hydroxide, magnesium hydroxide, sodium carbonate or sodium bicarbonate. For any given purification process the optimal amount and type of acid or base used may be determined empirically. An alternative exemplary acidified solvent is 0.1% acetic acid in ethanol or 0.1% sodium hydroxide in ethanol. In alternative embodiments, the neutralizing agent consists of for example sodium hydroxide, sodium carbonate, potassium carbonate, and potassium t-amylate, sodium bicarbonate.

Acidified non-polar and polar solvents of the types described above can be useful in preparation of gradient elutions using ion exchange chromatography. The solvents used in the conversion can comprise an organic solvent, e.g., a non-polar solvent, including a liquid non-polar solvent comprising lower C1-C12, or C3 to C8, straight chain or branched chain alkanes for example, methane, ethane, propane, butane, pentane, toluene, trimethylpentane, hexane; a low molecular weight alcohol, polar solvents consisting of for example, ethanol; a low molecular weight chlorinated hydrocarbon, for example, chloroform and dichloromethane; a heterocyclic compound or cyclic ether for example, tetrahydrofuran and 2-Methyltetrahydrofuran and aromatic ring hydrocarbons such as benzene, toluene, xylene and ethylbenzene.

In alternative embodiments, the plant material is subjected to a decarboxylation step prior to solvent extraction. The purpose of the decarboxylation step is to convert cannabinoid acids present in the plant material to the corresponding free cannabinoids. In alternative embodiments, the decarboxylation is carried out by heating the plant material to a defined temperature for a suitable length of time. Decarboxylation of cannabinoid acids is a function of time and temperature, thus at higher temperatures a shorter period of time will be taken for complete decarboxylation of a given amount of cannabinoid acid. In alternative embodiments selecting appropriate conditions for decarboxylation consideration include minimizing thermal degradation of the desirable, pharmacological cannabinoids into undesirable degradation products, particularly thermal degradation of $\Delta^9$-THC. In alternative embodiments, the decarboxylation is carried out in a multi-step heating process in which the plant material is: i) heated to a first temperature for a first (relatively short) time period to evaporate off retained water and allow for uniform heating of the plant material; and ii) the temperature is increased to a second temperature for a second time period (typically longer than the first time period) until at least 95% conversion of the acid cannabinoids to their neutral form has occurred.

In alternative embodiments, the "extract containing a cannabinoid or a cannabinoid acid" prepared from the starting plant material comprises a "botanical drug substance" prepared from the plant material, or a polar or non-polar solvent solution of such a botanical drug substance. In the context of this application a "botanical drug substance" is an extract derived from plant material, which extract fulfills the definition of "botanical drug substance" provided in the Guidance for Industry Botanical Drug Products Draft Guidance, August 2000, US Department of Health and Human Services, Food and Drug Administration Centre for Drug Evaluation and Research of: "A drug substance derived from one or more plants, algae, or macroscopic fungi. It is prepared from botanical raw materials by one or more of the following processes: pulverization, decoction, expression, aqueous extraction, ethanolic extraction, or other similar processes." "Botanical drug substances" derived from cannabis plants include primary extracts prepared by such processes as, for example, maceration, percolation, and solvent extraction.

In alternative embodiments, solvent extraction may be carried out using essentially any solvent that dissolves, or substantially dissolves, cannabinoids/cannabinoid acids, such as for example C1 to C5 alcohols (e.g. ethanol, methanol), C5-C12 alkanes (e.g. hexane), norflurane (HFA134a), 1,1,1,2,3,3,3-Heptafluoropropane (or HFA227), chloroform, dichloromethane, dichloroethane and carbon dioxide. When solvents such as those listed above are used, the resultant extract typically contains non-specific lipid-soluble material. This can optionally be removed by a variety of processes including filtration to remove solids, "winterization", which involves for example chilling to −20° C. or lower followed by filtration to remove waxy ballast, extraction with liquid carbon dioxide and by distillation.

In alternative embodiments, any protocol for the preparation of botanical drug substances from cannabis and hemp plant material can be used, e.g., as described in International patent application WO 02/064109. In alternative embodiments, the botanical drug substance is obtained by carbon dioxide ($CO_2$) extraction, polar solvent extraction or non-polar solvent extraction or combinations thereof followed by a filtration. Optionally a secondary extraction is performed to remove a substantial proportion of non-cannabinoid materials, e.g. waxes, wax esters and glycerides, unsaturated fatty acid residues, terpenes, carotenes, and flavonoids and other ballast.

In alternative embodiments, if it is intended to prepare free cannabinoids from the plant or microbial material, e.g., cannabis, then the material is heated to a defined temperature for a defined period of time in order to partially or substantially decarboxylate cannabinoid acids to free cannabinoids prior to extraction of the botanical drug substance. In alternative embodiments, the botanical drug substance is prepared according to a process comprising the following steps: i) optional decarboxylation of the plant material, ii) extraction with polar or non-polar solvent, to produce a crude botanical drug substance, iii) optional precipitation with C1-C5 alcohol to reduce the proportion of non-target materials, iv) removing the precipitate (for example, by filtration, precipitation, centrifugation and the like), v) optional treatment with activated charcoal, and vi) evaporation to remove C1-C5 alcohol and water, thereby producing a final botanical drug substance.

In alternative embodiments, provided are methods for converting substantially purified cannabidiol (CBD) to Δ8-tetrahydrocannabinol (Δ8-THC) and Δ9-tetrahydrocannabinol (Δ9-THC). As will be appreciated by one knowledgeable in the art and as discussed below, the reaction times may be varied somewhat, producing product at different yields and purities. Furthermore, functional equivalents may be substituted where appropriate.

In alternative embodiments, an exemplary method of converting CBD to Δ8-tetrahydrocannabinol (Δ8-THC) and Δ9-tetrahydrocannabinol (Δ9-THC) comprises: providing a reaction mixture comprising a Lewis acid or non-oxidizing acid catalyst in a reaction solvent, adding a substantially pure CBD or substantially pure CBD and/or (Δ8-THC) and/or Δ9-tetrahydrocannabinol (Δ9-THC) to the reaction mixture, mixing said reaction mixture for a period of time; adding a neutralizing agent to said mixture; filtration of catalyst and neutralizing agent from mixture; optionally allowing mixture to separate into an aqueous and organic phase; optionally removing the reaction solvent; optionally dissolving organic phase in a second solvent; adding organic phase to a chromatography column and eluting the tetrahydrocannabinol from the organic phase. The tetrahydrocannabinol may then be combined with suitable excipients known in the art, thereby forming a pharmaceutical composition. In one embodiment, the mixture is allowed to separate into an aqueous phase and an organic phase; and optionally the process further comprises removing the organic phase). In alternative embodiments, the tetrahydrocannabinol at therapeutically effective concentrations or dosages is combined with a pharmaceutically or pharmacologically acceptable carrier, excipient or diluent, either biodegradable or non-biodegradable. Exemplary examples of carriers include, but are by no means limited to, for example, poly(ethylene-vinyl acetate), copolymers of lactic acid and glycolic acid, poly(lactic acid), gelatin, collagen matrices, polysaccharides, poly(D,L lactide), poly(malic acid), poly (caprolactone), celluloses, albumin, starch, casein, dextran, polyesters, ethanol, methacrylate, polyurethane, polyethylene, vinyl polymers, glycols, mixtures thereof and the like. Standard excipients that can be used include gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethycellulose phthalate, non-crystalline cellulose, magnesium aluminum silicate, triethanolamine, polyvinyl alcohol, polyvinylpyrrolidone, sugars and starches. See, for example, Remington: The Science and Practice of Pharmacy, 1995, Gennaro ed.

In some embodiments, the catalyst is a Lewis acid, for example, p-toluenesulfonic acid, boron trifluoride or $BF_3Et_2O$. In some embodiments, the $BF_3Et_2O$ (boron trifluoride diethyl etherate) is in dry methylene chloride, ethyl acetate, ethanol, hexane or other organic solvent. In yet other examples, the catalyst may be hydrochloric acid in ethanol or sulfuric acid in cyclohexane.

In some embodiments, the catalyst is a non-oxidizing acid, for example, formic acid, acetic acid or hydrobromic acid. In some embodiments, the non-oxidizing acid is in dry methylene chloride, ethyl acetate, ethanol, hexane or other organic solvent.

In some embodiments, a base is added to the reaction mixture prior to optionally allowing the reaction mixture to separate into organic and aqueous phases. The base may be an alkali metal hydrogen carbonate, carbonate of an alkali metal, lithium hydroxide (LiOH), sodium hydroxide (NaOH), potassium hydroxide (KOH), rubidium hydroxide (RbOH), cesium hydroxide (CsOH), magnesium hydroxide (Mg(OH)), calcium hydroxide (Ca(OH)), strontium hydroxide (Sr(OH)), barium hydroxide (Ba(OH)).

In some embodiments, the organic layer is dried prior to eluting. In these embodiments, a suitable drying or dehydration compound, for example, MgSO4 or $Na_2SO_4$ is used.

In yet other embodiments, the process may be carried out under an inert atmosphere such as a nitrogen (e.g., $N_2$) atmosphere.

In alternative embodiments, and as discussed below, yield is determined by looking at the peak area for the isolated compound in the gas chromatography-mass spectra analysis of the crude reaction product mixture and the final reaction product mixture. It is important to note that in the prior art, yield is often calculated on the basis of first isolated crude product before final purification. In some embodiments of processes provided herein yield of Δ8-THC and Δ9-THC is at least about 75%; in other embodiments, the yield of Δ8-THC and Δ9-THC is at least about 90%; and in other embodiments, yield of Δ8-THC and Δ9-THC is at least about 98%; and in yet other embodiments, yield of Δ8-THC and Δ9-THC is between about 75 to 98% or 99%.

In alternative embodiments, purity is determined by Gas Chromatography-Mass Spectrometry (GC-MS) and/or by analytical high-performance liquid chromatography (HPLC). The total ion chromatogram from the GC-MS gives information similar to that provided by a flame ionization detector (FID)-GC in that the peak area is proportional to the mass of the analytes detected. Total peak area and the peak areas of the individual analytes can be compared in the GC-MS case as long as the masses are in generally the same range. As discussed below, in some embodiments, purity of the Δ8-THC and Δ9-THC mixture isolated by the process is greater than about 90%, 95%, 97% or 98%, or purity is greater that about 98% to 99%.

Continuous Chromatography Apparatus or Devices

In alternative embodiments, processes and methods as provided herein comprise use of continuous chromatography apparatus or devices, and associated robots and software. Any continuous chromatography apparatus or device known in the art can be used, e.g., as described in: Challener, BioPharm International, Vol 31, Issue 4, pg 14-18; Zobel et al Ind. Eng. Chem. Res., 2014, 53 (22), pp 9169-9185; Horvath et al Org. Process Res. Dev., 2015, 19 (6), pp 624-634; or as manufactured e.g., by Ionex, Calgon, ThermoFischer Scientific.

Any of the above aspects and embodiments can be combined with any other aspect or embodiment as disclosed here in the Summary, Figures and/or Detailed Description sections.

As used in this specification and the claims, the singular forms "a," "an" and "the" include plural referents unless the context clearly dictates otherwise.

Unless specifically stated or obvious from context, as used herein, the term "or" is understood to be inclusive and covers both "or" and "and".

Unless specifically stated or obvious from context, as used herein, the term "about" is understood as within a range of normal tolerance in the art, for example within 2 standard deviations of the mean. About can be understood as within 20%, 19%, 18%, 17%, 16%, 15%, 14%, 13%, 12% 11%, 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Unless specifically stated or obvious from context, as used herein, the terms "substantially all", "substantially most of", "substantially all of" or "majority of" encompass at least about 90%, 95%, 97%, 98%, 99% or 99.5%, or more of a referenced amount of a composition.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Incorporation by reference of these documents, standing alone, should not be construed as an assertion or admission that any portion of the contents of any document is considered to be essential material for satisfying any national or regional statutory disclosure requirement for patent applications. Notwithstanding, the right is reserved for relying upon any of such documents, where appropriate, for providing material deemed essential to the claimed subject matter by an examining authority or court.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention. Embodiments of the invention are set forth in the following claims.

The invention will be further described with reference to the examples described herein; however, it is to be understood that the invention is not limited to such examples.

EXAMPLES

Example 1: Exemplary Methods

In alternative embodiments, the "extract, aliquot or sample comprising or containing a cannabinoid or a cannabinoid acid" is dissolved in a gradient elution solution and subjected to a chromatographic purification step to produce substantially pure cannabinoids and a product enriched in a given cannabinoid. The purpose of this step is to first remove the targeted non-cannabinoid material comprising for example terpenes, carotenes, and flavonoids and also to provide a degree of separation/fractionation of the various cannabinoid/cannabinoid acid components of the extract.

In alternative embodiments, the product of the gradient elution chromatographic step is collected in multiple fractions, which may then be tested for the presence of the desired cannabinoid/cannabinoid acid using any suitable analytical technique. Fractions enriched in the desired cannabinoid and/or cannabinoid acid may then be selected for further purification. Optionally the gradient elution solution is removed from the selected fractions or optionally additional gradient solvent solution is added to change the polarity or hydrogen potential of the gradient solvent solution contained in the selected fraction. The selected fraction can then be subjected to one or more additional chromatographic steps and one or more gradient elution solutions modifications.

In alternative embodiments, the chromatographic step comprises a column chromatography in a fixed or a continuous mode, and is can be based on molecular sizing, polarity and/or hydrogen potentiality. In alternative embodiments, the column matrix materials are, for example; silica (or silica gel) and/or alumina normal phase and reverse phase such as for example C18, C8, C4, C2, amino, cyano, phenyl, diol, WAX, SAX, WCX, SCX, thiol; acidic, basic and neutral, styrenic, divinylbenzene, polystyrene/divinylbenzene, brominated styrenic; ion exchange resins such as strongly acidic, typically featuring sulfonic acid groups, e.g. sodium polystyrene sulfonate or polyAMPS; strongly basic, typically featuring quaternary amino groups, for example, trimethylammonium groups, e.g. polyAPTAC); weakly acidic, typically featuring carboxylic acid groups; weakly basic, typically featuring primary, secondary, and/or tertiary amino groups, e.g. polyethylene amine.

In alternative embodiments, various different elution solutions are used in combination with this type of matrix, for example dimethyl sulfoxide, pyridine water, dimethylformamide, methanol, ethylene dichloride, chloroform, propanol, ethanol, isobutanol, formamide, methylene dichloride, butanol, isopropanol, tetrahydrofuran, dioxane, hexane, butane, pentane, heptane, octane, terpene, hemiterpene, monoterpene, diterpene, limonene, humulene, pinene, myrcene, caryophylene, carbon tetrachloride, and equivalents, or any combination thereof.

In alternative embodiments, the chromatographic step comprises column chromatography on for example, a silica (or silica gel) or an alumina column, and the step can comprise eluting with a 5:1; 4:1; 3:1; 2:1; 1.9:1; 1.8:1; 1.7:1; 1.6:1; 1.5:1; 1.4:1; 1.3:1; 1.2:1; 1.1:1; 1.01:1; 1:1; 0.9:1; 0.5:1; 0.1:1 mixture of elution solutions such as heptane, hexane, pentane, butane, terpene, hemiterpene, monoterpene, diterpene, limonene, humulene, pinene, myrcene, caryophylene, chloroform, methylene dichloride, ethylene dichloride, methanol, ethanol, propanol and/or water. Any suitable combination of normal phase column packing material and solvent having separation characteristics suitable for use in separation (fractionation) of cannabinoids and/or cannabinoid acids can be used with equivalent effect.

In alternative embodiments, the column gradient eluate is collected in several fractions. The fractions are tested for the presence of the desired cannabinoid and/or cannabinoid acid using a suitable analytical technique, and those fractions containing the highest amounts of the desired cannabinoid and/or cannabinoid acid selected for further processing. Solvent can be then removed from the selected fractions, for example, by evaporation, e.g., rotary evaporation or equivalents.

In alternative embodiments, the fractions enriched in a given cannabinoid obtained from the gradient elution normal phase chromatographic step are mixed with a solvent of the opposite polarity thereby causing a concentration of the cannabinoids in the second solvent phase. In alternative embodiments, the solvent is then removed.

In alternative embodiments, the fractions containing a product enriched in a given cannabinoid obtained from the gradient elution normal phase chromatographic step or steps are re-dissolved in a gradient elution solution. In alternative embodiments, the fractions containing a product enriched in a given cannabinoid such as mixtures comprising CBD and THC, or mixtures of CBD and CBG or mixtures of CBG and CBC, are dissolved in a gradient elution solution and subjected to a reverse phase chromatographic purification step to produce substantially pure extracts.

In alternative embodiments, the product of the reverse phase chromatographic step is collected in multiple fractions, which may then be tested for the presence of the desired cannabinoid and/or cannabinoid acid using any suitable analytical technique.

Fractions enriched in the desired cannabinoid or cannabinoid acid may then be selected for further purification. In alternative embodiments, the elution solution is removed from the selected fractions or optionally additional solution is added to change the polarity of the solution contained in the selected fraction.

An exemplary embodiment comprises: fractions enriched in a given cannabinoid obtained from the elution of a reverse phase chromatographic step are mixed with a solvent of the opposite polarity thereby causing a concentration of the cannabinoids in the second solvent phase. In alternative embodiments, the solvent is then removed. In alternative embodiments, the selected fraction is then subjected to one or more additional reverse phase chromatographic steps and one or more elution solutions modifications. In alternative embodiments, the reverse phase chromatographic step comprises a column chromatography in fixed or continuous mode, and can be based on polarity. Examples of reverse phase column chromatography include but are not limited to pure silica, alkyl chain-bonded silica, cyano-bonded silica, and phenyl-bonded silica, alkyl chain-bonded silica, cyano-bonded silica, and phenyl-bonded silica, C18, C8, C4, C2, amino, cyano, phenyl, diol, WAX, SAX, WCX, SCX, thiol; acidic, basic and neutral, styrenic, divinylbenzene, polystyrene/divinylbenzene, brominated styrenic and equivalents and combinations thereof.

In alternative embodiments, various different elution solutions may be used in combination with this type of matrix, for example dimethyl sulfoxide, water, dimethylformamide, methanol, saline chloroform, propanol, ethanol, isobutanol, formamide, butanol, isopropanol, tetrahydrofuran, dioxane, dichloromethane, dichloroethane, etc.

In alternative embodiments, the chromatographic step comprises column chromatography using an ion exchange resin such as but not limited to RediSep® Rf SAX, Dowex® Marathon C Na, Marathon C H, Marathon MSC-1 or Dowex Marathon WBA™ column, and eluting can be with a 20:1; 15:1; 10:1, 5:1; 4.5:1; 4:1; 3.5:1; 3:1 2:1; 1.9:1; 1.8:1; 1.7:1; 1.6:1; 1.5:1; 1.4:1; 1.3:1; 1.2:1; 1.1:1; 1.01:1; 1.001:1; 0.1:1 mixture of elution solvents such as chloroform, dichloromethane, dichloroethane, ethanol, propanol, dimethyl sulfoxide, water, dimethylformamide, methanol, saline chloroform, propanol, ethanol, isobutanol, formamide, butanol, isopropanol, tetrahydrofuran, dioxane, dichloromethane, dichloroethane, acetic acid, carbonic acid, glycolic acid, benzoic acid, formic acid, oxalic acid, sodium hydroxide, potassium hydroxide, ammonium hydroxide, ammonium carbonate, and the like, and/or water. Any suitable combination of ion exchange phase column packing material and solvent having separation characteristics suitable for use in purification of cannabinoids and cannabinoids acid can be used with equivalent effect.

In alternative embodiments, the column eluate is collected in several fractions.

In alternative embodiments, the fractions are tested for the presence of the desired cannabinoid or cannabinoid acid using a suitable analytical technique, and those fractions containing the highest amounts of the desired cannabinoid or cannabinoid acid. In alternative embodiments, solvent is then removed from the selected fractions, optionally by evaporation, e.g., rotary evaporation.

In alternative embodiments, the fractions containing a product are enriched in a given cannabinoid acid obtained from the elution chromatographic step or steps, and the fractions containing a product enriched in a given cannabinoid acid obtained from elution reverse phase step or steps are re-dissolved in an elution solution. In alternative embodiments, the fractions containing a product enriched in a given cannabinoid acid such as tetrahydrocannabinolic acid (THCA), are dissolved in an elution solution and subjected to an ion exchange chromatographic purification step to produce substantially pure extracts. In alternative embodiments, the product of the ion exchange chromatographic step is collected in multiple fractions, which may then be tested for the presence of the desired cannabinoid or cannabinoid acid using any suitable analytical technique. Fractions enriched in the desired cannabinoid or cannabinoid acid may then be selected for further purification. In alternative embodiments, the elution solution is removed from the selected fractions or optionally additional solution is added to change the polarity and/or hydrogen potential of the solution contained in the selected fraction. An exemplary embodiment comprises having the fractions enriched in a given cannabinoid obtained from the elution ion exchange chromatographic step mixed with a solvent of the opposite polarity thereby causing a concentration of the cannabinoids in the second solvent phase. The solvent can then be removed.

In alternative embodiments, the selected fraction is then subjected to one or more additional ion exchange chromatographic steps and one or more isocratic or gradient elution solutions modifications. The ion exchange chromatographic step can comprise column chromatography in fixed or continuous mode, and can be based on molecular sizing and polarity ion exchange resin such as but not limited to RediSep® Rf SAX, Dowex® Marathon C Na, Marathon C H, Marathon MSC-1 or Dowex Marathon WBA™.

In alternative embodiments, various different elution solutions may be used in combination with this type of matrix, for example dimethyl sulfoxide, water, dimethylformamide, methanol, ethylene dichloride, chloroform, propanol, ethanol, isobutanol, formamide, methylene dichloride, butanol, isopropanol, tetrahydrofuran, dioxane, acetic acid, carbonic acid, glycolic acid, benzoic acid, formic acid, oxalic acid, sodium hydroxide, potassium hydroxide, ammonium hydroxide, ammonium carbonate, etc.

In alternative embodiments, essential features of the process are the same for purification of all cannabinoids and cannabinoid acids. *Cannabis* plants generally contain complex mixtures of cannabinoid acids and cannabinoids, although depending on the variety of cannabis one type of cannabinoid may pre-dominate. The purpose of the elution (e.g., gradient elution) chromatographic steps (ii) is to separate the various cannabinoid and/or cannabinoid/cannabinoid acid components of the crude plant extract loaded in step (i), as described above, into substantially pure fractions or substantially pure mixtures of fractions which are then optionally subjected to isomerization reactions and/or elimination reactions and/or additional gradient elution chromatography comprising normal phase, reverse phase and/or ion exchange.

In alternative embodiments, the product of the chromatographic step is collected in multiple fractions, which may then be tested for the presence of the desired cannabinoid/cannabinoid acid using any suitable analytical technique.

Fractions enriched in the desired cannabinoid/cannabinoid acid may then be selected for further purification. Hence, the same simple process steps may be adapted for purification of essentially any plant-derived cannabinoid or cannabinoid acid.

Selectivity for different cannabinoids or cannabinoid acids may be enhanced by selection of appropriate starting plant material. By way of example, if it is desired to prepare substantially pure $\Delta^9$ THC or $\Delta^9$ THCA then "high THC" cannabis plants can be selected as the starting material. Alternatively, if it is desired to prepare substantially pure CBD or CBDA then "high CBD" cannabis plants can be selected as the starting material. It is to be understood that the processes as provided herein are of general utility and are not limited to the use of particular *Cannabis* varieties as the starting material. The precise cannabinoid content of any particular *Cannabis* plant material can be qualitatively and quantitatively determined using analytical techniques well known to those skilled in the art, such as thin-layer chromatography or high-performance liquid chromatography (HPLC). Thus, one can screen a range of various *Cannabis* plants and select those having a high content of the desired cannabinoid acid or cannabinoid for use as starting material in a process as provided herein.

With the use of conventional selective breeding techniques it is possible to develop cannabis varieties (chemovars) having varying cannabinoid content. Select cannabis varieties (chemovars) have relatively high content of CBD, or of the minor cannabinoids $\Delta^9$-tetrahydrocannabivarin ($\Delta^9$-THCV), cannabigerol (CBG) or cannabichromene (CBC). General protocols for growing of medicinal cannabis and for testing the cannabinoid content of cannabis plants are described in International patent application WO 02/064109.

In alternative embodiments, methods further provide for the generation of a substantially pure preparation of $\Delta^9$ THC having a chromatographic purity of greater than about 75%, 80%, 90%, 95%, 96%, 97%, 98%, or 99% or more by area normalization of an HPLC profile. The preparation can be a semi-solid at room temperature. The preparation can comprise less than about 1.5%, less than about 0.4%, or less than about 0.2%; or, less than about 0.1% CBD (w/w), less than about 0.5%, less than about 0.4%, or less than about 0.2%, or less than about 0.1% CBD (w/w) as analyzed by HPLC.

In alternative embodiments, the pure $\Delta^8$-THC and $\Delta^9$-THC provided by exemplary methods as provided herein have utility as an active pharmaceutical agent, and is also useful as a chromatographic standard, particularly as a comparative standard in the qualitative analysis of botanical drug substances derived from cannabis. The availability of highly pure $\Delta^8$-THC and $\Delta^9$-THC will also facilitate studies of the pharmacology of $\Delta^8$-THC and $\Delta^9$-THC mixtures.

In alternative embodiments, an exemplary method for preparation of substantially pure $\Delta^8$-THC and $\Delta^9$ THC comprises:

i) obtaining an ethanol, hexane or terpene extraction solution of a botanical drug substance from cannabis or hemp plant material, ii) passing the solution obtained in step i) through a filter, and collecting the eluate, iii) optionally substantially remove solvent from the eluate by evaporation, e.g., rotary evaporation, to give a cannabinoid enriched fraction, iv) optionally adding solvent to the eluate, v) passing a solution of the resulting cannabinoid enriched extract through a column packed with a stationary phase resin such as DOWEX® MARATHON C Na™, MARATHON C H™, and conducting a gradient elution of 50:1; 20:1; 10:1; 9:1; 8:1; 7:1; 6:1; 5:1; 4:1; 3:1; 2:1; 1; 1; 0.5:1; 0.005:1; 0.0005:1 chloroform/methanol or ethanol, vi) adjusting hydrogen potential of said solution, vii) collecting $\Delta^9$-THC and CBD enriched fractions and optionally removing solvent, e.g., by evaporation, e.g., rotary evaporation, viii) mixing the collected $\Delta^9$ THC and CBD with a reaction solvent and a catalyst for a period of time and adding a neutralizing agent and removing catalyst and neutralizing agent by filtration to generate a reduced CBD and enriched $\Delta^8$-THC and $\Delta^9$-THC mixture, optionally removing reaction solvent, ix) mixing reduced CBD and enriched $\Delta^8$-THC and $\Delta^9$-THC mixture with optionally additional reaction solvent and a stabilizing agent, mixing stabilizing agent for a period of time x) optionally removing the reaction solvent, x) optionally re-dissolving the enriched $\Delta^8$ THC, $\Delta^9$ THC and reduced CBD prepared in steps viii) through x) and passing the solution through a column packed with reverse phase resin, and conducting a gradient elution of 10:1; 9:1; 8:1; 7:1; 6:1; 5:1; 4:1; 3:1; 2:1; 1; 1 methanol/water, xiii) optionally re-dissolving the crude $\Delta^8$ THC, $\Delta^9$ THC and reduced CBD prepared in steps viii) through x) and passing the solution through a column packed with an ion exchange resin such as DOWEX® MARATHON C Na™, MARATHON C H™, and conducting an elution of 50:1; 20:1; 10:1; 9:1; 8:1; 7:1; 6:1; 5:1; 4:1; 3:1; 2:1; 1; 1; 0.5:1; 0.005:1; 0.0005:1 chloroform and polar solvent mixture.

xiv) adjusting hydrogen potential of said solution xv) collecting the THC enriched fractions and removing solvent, e.g., by evaporation, e.g., rotary evaporation, to give a semi-solid preparation of THC.

Example 2: Conversion of CBD to $\Delta^8$-THC and $\Delta^9$-THC

This Example describes an exemplary method for the conversion of CBD to $\Delta^8$-THC and $\Delta^9$-THC.

CBD (1 g) was added to 6.4 ml of reaction solvent and 1% p-toluenesulfonic acid. In this example, the mixture was reacted for 48 hours, although other time periods can also be used, as discussed below. It was then diluted with ether (20 ml) and poured into water, the upper layer was separated, washed with aqueous 5% NaHCO$_3$, then with water, dried over MgSO$_4$ and evaporated. GC-MS analysis on the crude product, showed the presence of 1.1% CBD; 18.4% $\Delta^8$-THC and 80.0% $\Delta^9$-THC. The crude product was then subjected to column chromatography. In the example described above, normal phase HPLC separation is used wherein the column is for example a silica gel and the mobile phase is an organic solvent mixture introduced as a gradient described in the invention. In other embodiments, reverse phase HPLC separation is used.

The p-toluenesulfonic acid is used as a catalyst in the above example. It is of note that boron trifluoride could also be used as a catalyst, as could a number of other Lewis acids or non-oxidizing acid catalysts. The exact proportion is not essential to the reaction proceeding. Other solvents can also be used, for example, benzene, toluene, chloroform, dichloromethane, etc.

In other embodiments, anhydrous MgSO$_4$ or another suitable agents such as Na$_2$SO$_4$, CaSO$_4$, and CaCl$_2$), known in the art is used in place of the MgSO$_4$.

Example 3: Conversion of CBD to $\Delta^8$-THC and $\Delta^9$-THC

This Example describes an exemplary method for the conversion of CBD to $\Delta^8$-THC and $\Delta^9$-THC.

A hemp extract was obtained by extraction of hemp in ethanol. The hemp extract was composed of CBD, THC, cannabinoids and other components and subjected to conversion of CBD to THC without further purification. The hemp extract and 1-5 mol % p-toluenesulfonic acid were sequentially added to 6.4 mL reaction solvent. In this example, the reaction mixture was stirred at room temperature for 24 hours, although other time periods can also be used, as discussed below. At some time intervals, the reaction mixture was diluted with ether (20 mL) and poured into water. The upper layer was separated, washed with aqueous 5% NaHCO$_3$, dried over MgSO$_4$ and concentrated on a rotary evaporator. GC-MS analysis on the crude product showed the conversion of CBD to $\Delta^8$-THC and $\Delta^8$-THC, for example, 0% CBD; 98% $\Delta^9$-THC; 2% $\Delta^8$-THC after 24 hours in the presence of 3 mol % p-toluenesulfonic acid. The crude product was then subjected to column chromatography. In the example described above, normal phase HPLC separation is used wherein the column is for example a silica gel and the mobile phase is an organic solvent mixture introduced as a gradient described in the invention. In other embodiments, reverse phase HPLC separation is used.

The p-toluenesulfonic acid is used as a catalyst in the above example. Boron trifluoride could also be used as a catalyst, as could a number of other Lewis acids or non-oxidizing acids known in the art. Other solvents can also be used, for example, benzene, toluene, chloroform, dichloromethane, etc.

In other embodiments, anhydrous MgSO$_4$ or another suitable agents such as Na$_2$SO$_4$, CaSO$_4$, and CaCl$_2$), known in the art is used in place of the MgSO$_4$.

Example 4: Exemplary Methods

In alternative embodiments, the "extract containing a cannabinoid or a cannabinoid acid" is dissolved in a gradient elution solution and subjected to a chromatographic purification step to produce substantially pure cannabinoids and a product enriched in a given cannabinoid. The purpose of this step is to first remove the targeted non-cannabinoid material comprising for example terpenes, carotenes, and flavonoids and also to provide a degree of separation/fractionation of the various cannabinoid/cannabinoid acid components of the extract.

In alternative embodiments, the product of the chromatographic step is collected in multiple fractions, which can then be tested for the presence of the desired cannabinoid/cannabinoid acid using any suitable analytical technique.

Fractions enriched in the desired cannabinoid and/or cannabinoid acid can then be selected for further purification. Optionally the gradient elution solution is removed from the selected fractions or optionally additional gradient solvent is added to change the polarity or hydrogen potential of the gradient solvent contained in the selected fraction. The selected fraction can then be subjected to one or more additional chromatographic steps and one or more gradient elution solutions modifications.

In alternative embodiments, the chromatographic step comprises a column chromatography in a fixed or a continuous mode, and is can be based on molecular sizing, polarity and/or hydrogen potentiality. In alternative embodiments, the column matrix materials are, for example; silica (or silica gel) and alumina normal phase and reverse phase such as for example C18, C8, C4, C2, Amino, Cyano, Phenyl, Diol, WAX, SAX, WCX, SCX, thiol; acidic, basic and neutral, styrenic, divinylbenzene, polystyrene/divinylbenzene, brominated styrenic; ion exchange resins such as strongly acidic, typically featuring sulfonic acid groups, e.g. sodium polystyrene sulfonate or polyAMPS; strongly basic, typically featuring quaternary amino groups, for example, trimethylammonium groups, e.g. polyAPTAC); weakly acidic, typically featuring carboxylic acid groups; weakly basic, typically featuring primary, secondary, and/or tertiary amino groups, e.g. polyethylene amine.

In alternative embodiments, various different elution solutions can be used in combination with this type of matrix, for example dimethyl sulfoxide, water, dimethylformamide, methanol, ethylene dichloride, chloroform, propanol, ethanol, isobutanol, formamide, methylene dichloride, butanol, isopropanol, tetrahydrofuran, dioxane, hexane, butane, pentane, heptane, octane, terpene, hemiterpene, monoterpene, diterpene, limonene, humulene, pinene, myrcene, caryophylene, carbon tetrachloride, and equivalents, or any combination thereof.

In alternative embodiments, the chromatographic step comprises column chromatography on for example, a silica (or silica gel) or an alumina column, and the step can comprise eluting with a 5:1; 4:1; 3:1; 2:1; 1.9:1; 1.8:1; 1.7:1; 1.6:1; 1.5:1; 1.4:1; 1.3:1; 1.2:1; 1.1:1; 1.01:1; 1:1; 0.9:1; 0.5:1; 0.1:1 mixture of elution solutions such as heptane, hexane, pentane, butane, terpene, hemiterpene, monoterpene, diterpene, limonene, humulene, pinene, myrcene, caryophylene, chloroform, methylene dichloride, ethylene dichloride, methanol, ethanol, propanol and/or water. Any suitable combination of normal phase column packing material and solvent having separation characteristics suitable for use in separation (fractionation) of cannabinoids and/or cannabinoid acids can be used with equivalent effect.

In alternative embodiments, the column gradient eluate is collected in several fractions. The fractions are tested for the presence of the desired cannabinoid and/or cannabinoid acid using a suitable analytical technique, and those fractions containing the highest amounts of the desired cannabinoid and/or cannabinoid acid selected for further processing. Solvent can be then removed from the selected fractions, e.g., by evaporation, e.g., rotary evaporation or equivalents.

In alternative embodiments, the fractions enriched in a given cannabinoid obtained from the gradient elution normal phase chromatographic step are mixed with a solvent of the opposite polarity thereby causing a concentration of the cannabinoids in the second solvent phase. In alternative embodiments, the solvent is then removed.

In alternative embodiments, the fractions containing a product enriched in a given cannabinoid obtained from the gradient elution normal phase chromatographic step or steps are re-dissolved in a gradient elution solution. In alternative embodiments, the fractions containing a product enriched in a given cannabinoid such as mixtures comprising CBD and THC, or mixtures of CBD and CBG or mixtures of CBG and CBC, are dissolved in a gradient elution solution and subjected to a reverse phase chromatographic purification step to produce substantially pure extracts.

In alternative embodiments, the product of the reverse phase chromatographic step is collected in multiple fractions, which can then be tested for the presence of the desired cannabinoid and/or cannabinoid acid using any suitable analytical technique. Fractions enriched in the desired cannabinoid or cannabinoid acid can then be selected for further purification. In alternative embodiments, the gradient elution solution is removed from the selected fractions or optionally additional gradient solvent is added to change the polarity of the gradient solvent contained in the selected fraction.

An exemplary embodiment comprises: fractions enriched in a given cannabinoid obtained from the gradient elution reverse phase chromatographic step are mixed with a solvent of the opposite polarity thereby causing a concentration of the cannabinoids in the second solvent phase. In alternative embodiments, the solvent is then removed. In alternative embodiments, the selected fraction is then subjected to one or more additional reverse phase chromatographic steps and one or more gradient elution solutions modifications. In alternative embodiments, the reverse phase chromatographic step comprises a column chromatography in fixed or continuous mode, and is can be based on polarity. Examples of reverse phase column chromatography include but are not limited to pure silica, al kyl chain-bonded silica, cyano-bonded silica, and phenyl-bonded silica, alkyl chain-bonded silica, cyano-bonded silica, and phenyl-bonded silica, C18, C8, C4, C2, amino, cyano, phenyl, diol, WAX, SAX, WCX, SCX, thiol; acidic, basic and neutral, styrenic, divinylbenzene, polystyrene/divinylbenzene, brominated styrenic and equivalents and combinations thereof.

In alternative embodiments, various different elution solutions can be used in combination with this type of matrix, for example dimethyl sulfoxide, water, dimethylformamide, methanol, saline chloroform, propanol, ethanol, isobutanol, formamide, butanol, isopropanol, tetrahydrofuran, dioxane, dichloromethane, dichloroethane, etc.

In alternative embodiments, the chromatographic step comprises column chromatography using an ion exchange resin such as but not limited to RediSep® Rf SAX, Dowex® Marathon C Na™, Marathon C H™, Marathon MSC-1™ or Dowex Marathon WBA™ column, and eluting can be with a 20:1; 15:1; 10:1, 5:1; 4.5:1; 4:1; 3.5:1; 3:1 2:1; 1.9:1; 1.8:1; 1.7:1; 1.6:1; 1.5:1; 1.4:1; 1.3:1; 1.2:1; 1.1:1; 1.01:1; 1.001:1; 0.1:1 mixture of elution solutions such as chloroform, dichloromethane, dichloroethane methanol, ethanol, propanol, dimethyl sulfoxide, pyridine water, dimethylformamide, methanol, ethylene dichloride, chloroform, propanol, ethanol, isobutanol, formamide, butanol, isopropanol, tetrahydrofuran, dioxane, dichloromethane, dichloroethane, acetic acid, carbonic acid, glycolic acid, benzoic acid, formic acid, oxalic acid, sodium hydroxide, potassium hydroxide, ammonium hydroxide, ammonium carbonate, etc, and/or water. Any suitable combination of ion exchange phase column packing material and solvent having separation characteristics suitable for use in purification of cannabinoids and cannabinoids acid can be used with equivalent effect.

In alternative embodiments, the column gradient eluate is collected in several fractions. In alternative embodiments, the fractions are tested for the presence of the desired cannabinoid or cannabinoid acid using a suitable analytical technique, and those fractions containing the highest amounts of the desired cannabinoid or cannabinoid acid. In alternative embodiments, solvent is then removed from the selected fractions, optionally by evaporation, e.g., rotary evaporation.

In alternative embodiments, the fractions containing a product are enriched in a given cannabinoid acid obtained from the gradient elution chromatographic step or steps, and the fractions containing a product enriched in a given cannabinoid acid obtained from gradient elution reverse phase step or steps are re-dissolved in a gradient elution solution. In alternative embodiments, the fractions containing a product enriched in a given cannabinoid acid such as tetrahydrocannabinolic acid (THCA), are dissolved in a gradient elution solution and subjected to an ion exchange chromatographic purification step to produce substantially pure extracts. In alternative embodiments, the product of the ion exchange chromatographic step is collected in multiple fractions, which can then be tested for the presence of the desired cannabinoid or cannabinoid acid using any suitable analytical technique. Fractions enriched in the desired cannabinoid or cannabinoid acid can then be selected for further purification. In alternative embodiments, the gradient elution solution is removed from the selected fractions or optionally additional gradient solvent is added to change the polarity and/or hydrogen potential of the gradient solvent contained in the selected fraction. An exemplary embodiment comprises: the fractions enriched in a given cannabinoid obtained from the gradient elution ion exchange chromatographic step are mixed with a solvent of the opposite polarity thereby causing a concentration of the cannabinoids in the second solvent phase. The solvent can then be removed.

In alternative embodiments, the selected fraction is then subjected to one or more additional ion exchange chromatographic steps and one or more gradient elution solutions modifications. The ion exchange chromatographic step can comprise column chromatography in fixed or continuous mode, and can be based on molecular sizing and polarity ion exchange resin such as but not limited to RediSep® Rf SAX, Dowex® Marathon C Na, Marathon C H, Marathon MSC-1 or Dowex Marathon WBA™ In alternative embodiments, various different elution solutions can be used in combination with this type of matrix, for example dimethyl sulfoxide, water, dimethylformamide, methanol, ethylene dichloride, propanol, ethanol, isobutanol, formamide, methylene dichloride, butanol, isopropanol, tetrahydrofuran, dioxane, chloroform, acetic acid, carbonic acid, glycolic acid, benzoic acid, formic acid, oxalic acid, sodium hydroxide, potassium hydroxide, ammonium hydroxide, ammonium carbonate, etc.

In alternative embodiments, essential features of the process are the same for purification of all cannabinoids and cannabinoid acids. Cannabis plants generally contain complex mixtures of cannabinoid acids and cannabinoids, although depending on the variety of cannabis one type of cannabinoid may pre-dominate. The purpose of the gradient elution chromatographic steps (ii) is to separate the various cannabinoid and/or cannabinoid/cannabinoid acid components of the crude plant extract loaded in step (i), as described above, into substantially pure fractions or substantially pure mixtures of fractions which are then optionally subjected to isomerization reactions and/or elimination reactions and/or additional gradient elution chromatography comprising normal phase, reverse phase and/or ion exchange.

In alternative embodiments, the product of the chromatographic step is collected in multiple fractions, which can then be tested for the presence of the desired cannabinoid/cannabinoid acid using any suitable analytical technique.

Fractions enriched in the desired cannabinoid/cannabinoid acid can then be selected for further purification. Hence, the same simple process steps can be adapted for purification of essentially any plant-derived cannabinoid or cannabinoid acid.

Selectivity for different cannabinoids or cannabinoid acids can be enhanced by selection of appropriate starting plant material. By way of example, if it is desired to prepare substantially pure $\Delta^9$ THC or $\Delta^9$ THCA then "high THC" cannabis plants can be selected as the starting material. Alternatively, if it is desired to prepare substantially pure CBD or CBDA then "high CBD" cannabis plants can be selected as the starting material. It is to be understood that processes as provided herein are of general utility and are not limited to the use of particular Cannabis varieties as the starting material. The precise cannabinoid content of any particular Cannabis plant material can be qualitatively and quantitatively determined using analytical techniques well known to those skilled in the art, such as thin-layer chromatography or high-performance liquid chromatography (HPLC). Thus, one may screen a range of various Cannabis plants and select those having a high content of the desired cannabinoid acid or cannabinoid for use as starting material in a process as provided herein.

With the use of conventional selective breeding techniques it is possible to develop cannabis varieties (chemovars) having varying cannabinoid content. Select cannabis varieties (chemovars) have relatively high content of CBD, or of the minor cannabinoids $\Delta^9$-tetrahydrocannabivarin ($\Delta^9$-THCV), cannabigerol (CBG) or cannabichromene (CBC). General protocols for growing of medicinal cannabis and for testing the cannabinoid content of cannabis plants are described in International patent application WO 02/064109.

In alternative embodiments, methods further provide for the generation of a substantially pure preparation of $\Delta^9$ THC having a chromatographic purity of greater than about 75%, 80%, 90%, 95%, 96%, 97%, 98%, or 99% or more by area normalization of an HPLC profile. The preparation can be a semi-solid at room temperature. The preparation can comprises less than about 1.5%, less than about 0.4%, or less than about 0.2%; or, less than about 0.1% CBD (w/w), less than about 0.5%, less than about 0.4%, or less than about 0.2%, or less than about 0.1% CBD (w/w) as analyzed by HPLC.

In alternative embodiments, the pure $\Delta^9$-THC provided by exemplary methods as provided herein have utility as an active pharmaceutical agent, and is also useful as a chromatographic standard, particularly as a comparative standard in the qualitative analysis of botanical drug substances derived from cannabis. The availability of highly pure $\Delta^9$-THC will also facilitate studies of the pharmacology of $\Delta^9$-THC.

In alternative embodiments, an exemplary method for preparation of substantially pure $\Delta^9$ THC comprises:
  i) obtaining an ethanolic solution of a botanical drug substance from cannabis or hemp plant material,
  ii) passing the solution obtained in step i) through a filter, and collecting the eluate,
  iii) optionally substantially remove solvent from the eluate, e.g., by evaporation, e.g., rotary evaporation, to give a cannabinoid enriched fraction,
  iv) optionally adding solvent to the eluate,
  v) passing a solution of the resulting cannabinoid enriched extract through a column packed with a stationary phase resin such as DOWEX® MARATHON C Na™, MARATHON C H™, and conducting a gradient elution of 50:1; 20:1; 10:1; 9:1; 8:1; 7:1; 6:1; 5:1; 4:1; 3:1; 2:1; 1; 1; 0.5:1; 0.005:1; 0.0005:1 chloroform/methanol or ethanol,
  vi) adjusting hydrogen potential of said gradient solvent solution,
  vii) collecting $\Delta^9$-THC and CBD enriched fractions and optionally removing solvent, e.g., by evaporation, e.g., rotary evaporation,
  viii) mixing the collected $\Delta^9$ THC and CBD with a reaction solvent and a catalyst for a period of time and adding a neutralizing agent and removing catalyst and neutralizing agent by filtration to generate a CBD reduced A-THC and $\Delta^9$-THC mixture, optionally removing reaction solvent,
  ix) mixing CBD reduced $\Delta^8$-THC and $\Delta^9$-THC mixture with optionally additional reaction solvent and a stabilizing agent, mixing stabilizing agent for a period of time,
  x) mixing CBD reduced $\Delta^8$-THC and $\Delta^9$-THC and stabilizing agent mixture with an elimination agent.
  xi) separation of elimination agent and stabilizing agent from substantially $\Delta^9$ THC,
  xii) optionally re-dissolving the crude $\Delta^9$ THC and CBD prepared in step xi) and passing the solution through a column packed with reverse phase resin, and conducting a gradient elution of 10:1; 9:1; 8:1; 7:1; 6:1; 5:1; 4:1; 3:1; 2:1; 1; 1 methanol/water,
  xiii) optionally re-dissolving the crude $\Delta^9$ THC and CBD prepared in step xi) such as DOWEX® MARATHON C Na™, MARATHON C H™, and conducting a gradient elution of 50:1; 20:1; 10:1; 9:1; 8:1; 7:1; 6:1; 5:1; 4:1; 3:1; 2:1; 1; 1; 0.5:1; 0.005: 1; 0.0005:1 chloroform and polar solvent mixture.
  vi) adjusting hydrogen potential of said gradient solvent solution
  vii) collecting the $\Delta^9$ THC enriched fractions and removing solvent, e.g., by evaporation, e.g., rotary evaporation, to give a semi-solid preparation of $\Delta^9$ THC.
  (viii) collecting the CBD enriched fractions and removing solvent, e.g., by evaporation, e.g., rotary evaporation, to give a semi-solid preparation of CBD.

Example 5: Conversion of CBD to $\Delta^8$-THC and $\Delta^9$-THC

This Example describes an exemplary method for the conversion of CBD to $\Delta^8$-THC and $\Delta^9$-THC.

CBD (1 g) was added to 6.4 ml of reaction solvent and 1% p-toluenesulfonic acid. In this example, the mixture was reacted for 48 hours, although other time periods can also be used, as discussed below. It was then diluted with ether (20 ml) and poured into water, The upper layer was separated, washed with aqueous 5% $NaHCO_3$, then with water, dried over $MgSO_4$ and evaporated. GC-MS analysis on the crude product, showed the presence of 1.1% CBD; 18.4% $\Delta^8$-THC and 80.0% $\Delta^9$-THC. The crude product was then subjected to column chromatography. In the example described above, normal phase HPLC separation is used wherein the column is for example a silica gel and the mobile phase is an organic solvent mixture introduced as a gradient described in the invention. In other embodiments, reverse phase HPLC separation is used.

The p-toluenesulfonic acid is used as a catalyst in the above example. It is of note that boron trifluoride could also be used as a catalyst, as could a number of other Lewis acids or non-oxidizing acid catalysts. The exact proportion is not essential to the reaction proceeding. Other solvents can also be used, for example, benzene, toluene, chloroform, dichloromethane, etc.

In other embodiments, anhydrous $MgSO_4$ or another suitable agents such as $Na_2SO_4$, $CaSO_4$, and $CaCl_2$, known in the art is used in place of the $MgSO_4$.

Example 6: Conversion of $\Delta^8$ THC and $\Delta^9$ THC, and Purification of $\Delta^9$ THC This Example describes an exemplary method for the conversion of $\Delta^8$-THC and $\Delta^9$-THC, and the purification of $\Delta^9$ THC.

A mixture containing 1.1% CBD; 18.4% $\Delta^8$-THC and 80.0% $\Delta^9$-THC (1 g) was added to 20 mL of reaction solvent and then 65 mol % protection agent was added to the solution. The colorless solution was saturated with hydrogen chloride at 0° C. in a dry apparatus and stirred. The mixture was washed with water and treated with sodium bicarbonate. The solvent layer was concentrated and dried under high vacuum. 3 equivalents of elimination agent was then added to the mixture in a dry solvent and heated up to 65° C. for 15 min. The mixture was mixed with solvent and washed with water and treated with sodium bicarbonate. The organic layer was dried over sodium sulfate and concentrated and dried under high vacuum. GC-MS analysis on the crude product, showed the presence of 1% CBD; 3% $\Delta^8$-THC and 96% $\Delta^9$-THC. The crude product was then subjected to column chromatography. In the example described above, normal phase HPLC separation is used wherein the column is for example a silica gel and the mobile phase is an organic solvent mixture introduced as a gradient described in the invention. In other embodiments, reverse phase HPLC separation is used.

The zinc chloride is used as the protection agent in the above example. The exact proportion is not essential to the reaction proceeding. Other solvents can also be used, for example, benzene, toluene, chloroform, dichloromethane, etc.

Example 7: Conversion of CBD to $\Delta^8$-THC and $\Delta^9$-THC

This Example describes an exemplary method for the conversion of CBD to $\Delta^8$-THC and $\Delta^9$-THC.

A hemp extract was obtained by extraction of hemp in ethanol. The hemp extract was composed of CBD, THC, cannabinoids and other components and subjected to conversion of CBD to THC without further purification. The hemp extract and 1-5 mol % p-toluenesulfonic acid were sequentially added to 6.4 mL reaction solvent. In this example, the reaction mixture was stirred at room temperature for 24 hours, although other time periods can also be used, as discussed below. At some time intervals, the reaction mixture was diluted with ether (20 mL) and poured into water. The upper layer was separated, washed with aqueous 5% $NaHCO_3$, dried over $MgSO_4$ and concentrated on a rotary evaporator. GC-MS analysis on the crude product showed the conversion of CBD to $\Delta^8$-THC and $\Delta^8$-THC, for example, 0% CBD; 98% $\Delta^9$-THC; 2% $\Delta^8$-THC after 24 hours in the presence of 3 mol % p-toluenesulfonic acid. The crude product was then subjected to column chromatography. In the example described above, normal phase HPLC separation is used wherein the column is for example a silica gel and the mobile phase is an organic solvent mixture introduced as a gradient described in the invention. In other embodiments, reverse phase HPLC separation is used.

The p-toluenesulfonic acid is used as a catalyst in the above example. Boron trifluoride could also be used as a catalyst, as could a number of other Lewis acids or non-oxidizing acids known in the art. Other solvents can also be used, for example, benzene, toluene, chloroform, dichloromethane, etc.

In other embodiments, anhydrous $MgSO_4$ or another suitable agents such as $Na_2SO_4$, $CaSO_4$, and $CaCl_2$), known in the art is used in place of the $MgSO_4$.

Example 8: Exemplary Methods

In alternative embodiments, the "extract containing a cannabinoid or a cannabinoid acid" is dissolved in a gradient elution solution and subjected to a chromatographic purification step to produce substantially pure cannabinoids and a product enriched in a given cannabinoid. The purpose of this step is to first remove the targeted non-cannabinoid material comprising for example terpenes, carotenes, and flavonoids and also to provide a degree of separation/fractionation of the various cannabinoid/cannabinoid acid components of the extract.

In alternative embodiments, the product of the chromatographic step is collected in multiple fractions, which may then be tested for the presence of the desired cannabinoid/cannabinoid acid using any suitable analytical technique.

Fractions enriched in the desired cannabinoid and/or cannabinoid acid can then be selected for further purification. Optionally the gradient elution solution is removed from the selected fractions or optionally additional gradient solvent is added to change the polarity or hydrogen potential of the gradient solvent contained in the selected fraction. The selected fraction can then be subjected to one or more additional continuous chromatographic steps and one or more gradient elution solutions modifications.

In alternative embodiments, the chromatographic step comprises a column chromatography in a fixed or a continuous mode, and is can be based on molecular sizing, polarity and/or hydrogen potentiality. In alternative embodiments, the column matrix materials are, for example; silica (or silica gel) and alumina normal phase and reverse phase such as for example C18, C8, C4, C2, Amino, Cyano, Phenyl, Diol, WAX, SAX, WCX, SCX, thiol; acidic, basic and neutral, styrenic, divinylbenzene, polystyrene/divinylbenzene, brominated styrenic; ion exchange resins such as strongly acidic, typically featuring sulfonic acid groups, e.g. sodium polystyrene sulfonate or polyAMPS; strongly basic, typically featuring quaternary amino groups, for example, trimethylammonium groups, e.g. polyAPTAC); weakly acidic, typically featuring carboxylic acid groups; weakly basic, typically featuring primary, secondary, and/or tertiary amino groups, e.g. polyethylene amine.

In alternative embodiments, various different elution solutions can be used in combination with this type of matrix, for example dimethyl sulfoxide, pyridine water, dimethylformamide, methanol, ethylene dichloride, chloroform, propanol, ethanol, isobutanol, formamide, methylene dichloride, butanol, isopropanol, tetrahydrofuran, dioxane, hexane, butane, pentane, heptane, octane, terpene, hemiterpene, monoterpene, diterpene, limonene, humulene, pinene, myrcene, caryophylene, carbon tetrachloride, and equivalents, or any combination thereof.

In alternative embodiments, the chromatographic step comprises column chromatography on for example, a silica (or silica gel) or an alumina column, and the step can comprise eluting with a 5:1; 4:1; 3:1; 2:1; 1.9:1; 1.8:1; 1.7:1; 1.6:1; 1.5:1; 1.4:1; 1.3:1; 1.2:1; 1.1:1; 1.01:1; 1:1; 0.9:1; 0.5:1; 0.1:1 mixture of elution solutions such as heptane, hexane, pentane, butane, terpene, hemiterpene, monoterpene, diterpene, limonene, humulene, pinene, myrcene, caryophylene, chloroform, methylene dichloride, ethylene dichloride, methanol, ethanol, propanol and/or water. Any suitable combination of normal phase column packing material and solvent having separation characteristics suitable for use in separation (fractionation) of cannabinoids and/or cannabinoid acids can be used with equivalent effect.

In alternative embodiments, the column gradient eluate is collected in several fractions. The fractions are tested for the presence of the desired cannabinoid and/or cannabinoid acid using a suitable analytical technique, and those fractions containing the highest amounts of the desired cannabinoid and/or cannabinoid acid selected for further processing. Solvent can be then removed from the selected fractions, e.g., by evaporation, e.g., rotary evaporation or equivalents.

In alternative embodiments, the fractions enriched in a given cannabinoid obtained from the gradient elution normal phase chromatographic step are mixed with a solvent of the opposite polarity thereby causing a concentration of the cannabinoids in the second solvent phase. In alternative embodiments, the solvent is then removed.

In alternative embodiments, the fractions containing a product enriched in a given cannabinoid obtained from the gradient elution normal phase chromatographic step or steps are re-dissolved in a gradient elution solution. In alternative embodiments, the fractions containing a product enriched in a given cannabinoid such as mixtures comprising CBD and THC, or mixtures of CBD and CBG or mixtures of CBG and CBC, are dissolved in a gradient elution solution and subjected to a reverse phase chromatographic purification step to produce substantially pure extracts.

In alternative embodiments, the product of the reverse phase chromatographic step is collected in multiple fractions, which can then be tested for the presence of the desired cannabinoid and/or cannabinoid acid using any suitable analytical technique. Fractions enriched in the desired cannabinoid or cannabinoid acid can then be selected for further purification. In alternative embodiments, the gradient elution solution is removed from the selected fractions or optionally additional gradient solvent is added to change the polarity of the gradient solvent contained in the selected fraction.

An exemplary embodiment comprises: fractions enriched in a given cannabinoid obtained from the gradient elution reverse phase chromatographic step are mixed with a solvent of the opposite polarity thereby causing a concentration of the cannabinoids in the second solvent phase. In alternative embodiments, the solvent is then removed. In alternative embodiments, the selected fraction is then subjected to one or more additional reverse phase chromatographic steps and one or more gradient elution solutions modifications. In alternative embodiments, the reverse phase chromatographic step comprises a column chromatography in fixed or continuous mode, and is can be based on polarity. Examples of reverse phase column chromatography include but are not limited to pure silica, alkyl chain-bonded silica., cyano-bonded silica, and phenyl-bonded silica, alkyl chain-bonded silica, cyano-bonded silica, and phenyl-bonded silica, C18, C8, C4, C2, amino, cyano, phenyl, diol, WAX, SAX, WCX, SCX, thiol; acidic, basic and neutral, styrenic, divinylbenzene, polystyrene/divinylbenzene, brominated styrenic and equivalents and combinations thereof.

In alternative embodiments, various different elution solutions can be used in combination with this type of matrix, for example dimethyl sulfoxide, pyridine water, dimethylformamide, methanol, saline chloroform, propanol, ethanol, isobutanol, formamide, butanol, isopropanol, tetrahydrofuran, dioxane, dichloromethane, dichloroethane, etc.

In alternative embodiments, the chromatographic step comprises column chromatography using an ion exchange resin such as but not limited to RediSep® Rf SAX, Dowex® Marathon C Na, Marathon C H, Marathon MSC-1 or Dowex Marathon WBA™ column, and eluting can be with a 20:1; 15:1; 10:1, 5:1; 4.5:1; 4:1; 3.5:1; 3:1 2:1; 1.9:1; 1.8:1; 1.7:1; 1.6:1; 1.5:1; 1.4:1; 1.3:1; 1.2:1; 1.1:1; 1.01:1; 1.001:1; 0.1:1 mixture of elution solutions such as chloroform, dichloromethane, dichloroethane, methanol, ethanol, propanol, dimethyl sulfoxide, pyridine water, dimethylformamide, methanol, ethylene dichloride, chloroform, propanol, ethanol, isobutanol, formamide, butanol, isopropanol, tetrahydrofuran, dioxane, chloroform dichloromethane, dichloroethane, acetic acid, carbonic acid, glycolic acid, benzoic acid, formic acid, oxalic acid, sodium hydroxide, potassium hydroxide, ammonium hydroxide, ammonium carbonate, etc, and/or water. Any suitable combination of ion exchange phase column packing material and solvent having separation characteristics suitable for use in purification of cannabinoids and cannabinoids acid can be used with equivalent effect.

In alternative embodiments, the column gradient eluate is collected in several fractions. In alternative embodiments, the fractions are tested for the presence of the desired cannabinoid or cannabinoid acid using a suitable analytical technique, and those fractions containing the highest amounts of the desired cannabinoid or cannabinoid acid. In alternative embodiments, solvent is then removed from the selected fractions, optionally by evaporation, e.g., rotary evaporation.

In alternative embodiments, the fractions containing a product are enriched in a given cannabinoid acid obtained from the gradient elution chromatographic step or steps, and the fractions containing a product enriched in a given cannabinoid acid obtained from gradient elution reverse phase step or steps are re-dissolved in a gradient elution solution. In alternative embodiments, the fractions containing a product enriched in a given cannabinoid acid such as tetrahydrocannabinolic acid (THCA), are dissolved in a gradient elution solution and subjected to an ion exchange chromatographic purification step to produce substantially pure extracts. In alternative embodiments, the product of the ion exchange chromatographic step is collected in multiple fractions, which can then be tested for the presence of the desired cannabinoid or cannabinoid acid using any suitable analytical technique. Fractions enriched in the desired cannabinoid or cannabinoid acid can then be selected for further purification. In alternative embodiments, the gradient elution solution is removed from the selected fractions or optionally additional gradient solvent is added to change the polarity and/or hydrogen potential of the gradient solvent contained in the selected fraction. An exemplary embodiment comprises: the fractions enriched in a given cannabinoid obtained from the gradient elution ion exchange chromatographic step are mixed with a solvent of the opposite polarity thereby causing a concentration of the cannabinoids in the second solvent phase. The solvent can then be removed.

In alternative embodiments, the selected fraction is then subjected to one or more additional ion exchange chromatographic steps and one or more gradient elution solutions modifications. The ion exchange chromatographic step can comprise column chromatography in fixed or continuous mode, and can be based on molecular sizing and polarity ion exchange resin such as but not limited to RediSep® Rf SAX, Dowex® Marathon C Na, Marathon C H, Marathon MSC-1 or Dowex Marathon WBA™ In alternative embodiments, various different elution solutions can be used in combination with this type of matrix, for example dimethyl sulfoxide, pyridine water, dimethylformamide, methanol, ethylene dichloride, chloroform, propanol, ethanol, isobutanol, formamide, methylene dichloride, butanol, isopropanol, tetrahydrofuran, dioxane, acetic acid, carbonic acid, glycolic acid, benzoic acid, formic acid, oxalic acid, sodium hydroxide, potassium hydroxide, ammonium hydroxide, ammonium carbonate, etc.

In alternative embodiments, essential features of the process are the same for purification of all cannabinoids and cannabinoid acids. *Cannabis* plants generally contain complex mixtures of cannabinoid acids and cannabinoids, although depending on the variety of cannabis one type of cannabinoid may pre-dominate. The purpose of the gradient elution chromatographic steps (ii) is to separate the various cannabinoid and/or cannabinoid/cannabinoid acid components of the crude plant extract loaded in step (i), as described above, into substantially pure fractions or substantially pure mixtures of fractions which are then optionally subjected to isomerization reactions and/or elimination reactions and/or additional gradient elution chromatography comprising normal phase, reverse phase and/or ion exchange.

In alternative embodiments, the product of the chromatographic step is collected in multiple fractions, which can then be tested for the presence of the desired cannabinoid/cannabinoid acid using any suitable analytical technique.

Fractions enriched in the desired cannabinoid/cannabinoid acid can then be selected for further purification. Hence, the same simple process steps can be adapted for purification of essentially any plant-derived cannabinoid or cannabinoid acid.

Selectivity for different cannabinoids or cannabinoid acids can be enhanced by selection of appropriate starting plant material. By way of example, if it is desired to prepare substantially pure $\Delta^8$ THC then high CBD and/or high $\Delta^9$ THC and/or $\Delta^9$ THCA cannabis plants can be selected as the starting material. Alternatively, if it is desired to prepare substantially pure CBD or CBDA then "high CBD" cannabis plants can be selected as the starting material. I is to be understood that processes as provided herein are of general utility and are not limited to the use of particular *Cannabis* varieties as the starting material. The precise cannabinoid content of any particular *Cannabis* plant material can be qualitatively and quantitatively determined using analytical techniques well known to those skilled in the art, such as thin-layer chromatography or high-performance liquid chromatography (HPLC). Thus, one can screen a range of various *Cannabis* plants and select those having a high content of the desired cannabinoid acid or cannabinoid for use as starting material in a process as provided herein.

With the use of conventional selective breeding techniques it is possible to develop cannabis varieties (chemovars) having varying cannabinoid content. Select cannabis varieties (chemovars) have relatively high content of CBD, or of the minor cannabinoids $\Delta^9$-tetrahydrocannabivarin ($\Delta^9$-THCV), cannabigerol (CBG) or cannabichromene (CBC). General protocols for growing of medicinal cannabis and for testing the cannabinoid content of cannabis plants are described in International patent application WO 02/064109.

In alternative embodiments, methods further provide for the generation of a substantially pure preparation of $\Delta^8$ THC having a chromatographic purity of greater than about 75%, 80%, 90%, 95%, 96%, 97%, 98%, or 99% or more by area normalization of an HPLC profile. The preparation can be a semi-solid at room temperature. The preparation can comprises less than about 1.5%, less than about 0.4%, or less than about 0.2%; or, less than about 0.1% CBD (w/w), less than about 0.5%, less than about 0.4%, or less than about 0.2%, or less than about 0.1% CBD (w/w) as analyzed by HPLC.

In alternative embodiments, the pure $\Delta^8$-THC provided by exemplary methods as provided herein have utility as an active pharmaceutical agent, and is also useful as a chromatographic standard, particularly as a comparative standard in the qualitative analysis of botanical drug substances derived from cannabis. The availability of highly pure $\Delta^8$-THC will also facilitate studies of the pharmacology of $\Delta^8$-THC.

In alternative embodiments, an exemplary method for preparation of substantially pure $\Delta^9$ THC comprises:
 i) obtaining an ethanolic solution of a botanical drug substance from cannabis or hemp plant material,
 ii) passing the solution obtained in step i) through a filter, and collecting the eluate,
 iii) optionally substantially remove solvent from the eluate, e.g., by evaporation, e.g., rotary evaporation, to give a cannabinoid enriched fraction,
 iv) optionally adding solvent to the eluate,
 v) passing a solution of the resulting cannabinoid enriched extract through a column packed with a stationary phase resin such as DOWEX® MARATHON C Na™, MARATHON C H™, and conducting a gradient elution of 50:1; 20:1; 10:1; 9:1; 8:1; 7:1; 6:1; 5:1; 4:1; 3:1; 2:1; 1; 1; 0.5:1; 0.005:1; 0.0005:1 chloroform/methanol or ethanol,
 vi) adjusting hydrogen potential of said gradient solvent solution,
 vii) collecting $\Delta^8$-THC, $\Delta^9$-THC and CBD enriched fractions and optionally removing solvent, e.g., by evaporation, e.g., rotary evaporation, viii) mixing the collected $\Delta^8$-THC, $\Delta^9$ THC and CBD with a reaction solvent and a catalyst for a period of time and adding a neutralizing agent and removing catalyst and neutralizing agent by filtration to generate a substantially pure $\Delta^8$-THC product with a reduced CBD and $\Delta^9$-THC content, optionally removing reaction solvent, viii) optionally re-dissolving the substantially $\Delta^8$ THC mixture prepared in step viii) and passing the solution through a column packed with reverse phase resin, and conducting a gradient elution of 10:1; 9:1; 8:1; 7:1; 6:1; 5:1; 4:1; 3:1; 2:1; 1; 1 methanol/water, x) optionally re-dissolving the substantially $\Delta^8$ THC prepared in step viii) such as DOWEX® MARATHON C Na™, MARATHON C H™, and conducting a gradient elution of 50:1; 20:1; 10:1; 9:1; 8:1; 7:1; 6:1; 5:1; 4:1; 3:1; 2:1; 1; 1; 0.5:1; 0.005: 1; 0.0005:1 chloroform and polar solvent mixture.

xi) adjusting hydrogen potential of said gradient solvent solution xii) collecting the $\Delta^8$ THC enriched fractions and removing solvent, e.g., by evaporation, e.g., rotary evaporation to give a semi-solid preparation of $\Delta 8$ THC.

Example 9: Conversion of CBD to $\Delta^8$-THC and $\Delta^9$-THC

This Example describes an exemplary method for the conversion of CBD to $\Delta^8$-THC.

CBD (15 g) was added to 240 ml of reaction solvent and p-toluenesulfonic acid. In this example, the mixture was reacted for 27 hours, although other time periods can also be used, as discussed below. It was then diluted with ether (20 ml) and poured into water. The upper layer was separated, washed with aqueous 5% NaHCO$_3$, then with water, dried over MgSO$_4$ and evaporated. GC-MS analysis on the crude product, showed the presence of 96.5% $\Delta^8$-THC and 2.5% $\Delta^9$-THC. The crude product was then subjected to column chromatography. In the example described above, normal phase HPLC separation is used wherein the column is for example a silica gel and the mobile phase is an organic solvent mixture introduced as a gradient described in the invention. In other embodiments, reverse phase HPLC separation is used.

The p-toluenesulfonic acid is used as a catalyst in the above example. It is of note that boron trifluoride could also be used as a catalyst, as could a number of other Lewis acids or non-oxidizing acid catalysts. The exact proportion is not essential to the reaction proceeding. Other solvents can also be used, for example, benzene, toluene, chloroform, dichloromethane, etc.

In other embodiments, anhydrous MgSO$_4$ or another suitable agents such as Na$_2$SO$_4$, CaSO$_4$, and CaCl$_2$), known in the art is used in place of the MgSO$_4$.

Example 10: Exemplary Methods

In alternative embodiments, the "extract containing a cannabinoid or a cannabinoid acid" is dissolved in a gradient elution solution and subjected to one or multiple continuous chromatographic purification step to produce substantially pure cannabinoids and a product enriched in a given cannabinoid. The purpose of this step is to first remove the targeted non-cannabinoid material comprising for example terpenes, carotenes, and flavonoids and also to provide a degree of separation/fractionation of the various cannabinoid/cannabinoid acid components of the extract.

In alternative embodiments, the product of one or more continuous chromatographic steps is collected in multiple fractions, which may then be tested for the presence of the desired cannabinoid/cannabinoid acid using any suitable analytical technique. Fractions enriched in the desired cannabinoid and/or cannabinoid acid can then be selected for further purification. Optionally the gradient elution solution is removed from the selected fractions or optionally additional gradient solvent is added to change the polarity or hydrogen potential of the gradient solvent contained in the selected fraction. The selected fraction can then be subjected to one or more additional chromatographic steps and one or more gradient elution solutions modifications.

In alternative embodiments, the chromatographic step comprises a column chromatography in a continuous mode, and is based on molecular sizing, polarity and/or hydrogen potentiality. In alternative embodiments, the column matrix materials are, for example; silica (or silica gel), alumina and reverse phase for example C18, C8, C4, C2, Amino, Cyano, Phenyl, Diol, WAX, SAX, WCX, SCX, thiol; acidic, basic and neutral, styrenic, divinylbenzene, polystyrene/divinylbenzene, brominated styrenic; ion exchange resins such as strongly acidic, typically featuring sulfonic acid groups, e.g. sodium polystyrene sulfonate or polyAMPS; strongly basic, typically featuring quaternary amino groups, for example, trimethylammonium groups, e.g. polyAPTAC); weakly acidic, typically featuring carboxylic acid groups; weakly basic, typically featuring primary, secondary, and/or tertiary amino groups, e.g. polyethylene amine.

In alternative embodiments, various different elution solutions can be used in combination with this type of matrix, for example dimethyl sulfoxide, pyridine, water, dimethylformamide, methanol, saline, ethylene dichloride, chloroform, propanol, ethanol, isobutanol, formamide, methylene dichloride, butanol, isopropanol, tetrahydrofuran, dioxane, hexane, butane, pentane, heptane, octane, terpene, hemiterpene, monoterpene, diterpene, limonene, humulene, pinene, myrcene, caryophylene, carbon tetrachloride, and equivalents, or any combination thereof c. In alternative embodiments, the chromatographic step comprises continuous column chromatography on for example, a silica (or silica gel) or an alumina column, and the step can comprise eluting with a 5:1; 4:1; 3:1; 2:1; 1.9:1; 1.8:1; 1.7:1; 1.6:1; 1.5:1; 1.4:1; 1.3:1; 1.2:1; 1.1:1; 1.01:1; 1:1; 0.9:1; 0.5:1; 0.1:1 mixture of elution solutions such as heptane, hexane, pentane, butane, terpene, hemiterpene, monoterpene, diterpene, limonene, humulene, pinene, myrcene, caryophylene, chloroform, methylene dichloride, ethylene dichloride, methanol, ethanol, propanol and/or water. Any suitable combination of normal phase column packing material and solvent having separation characteristics suitable for use in separation (fractionation) of cannabinoids and/or cannabinoid acids can be used with equivalent effect.

In alternative embodiments, the column gradient eluate is collected in several fractions. The fractions are tested for the presence of the desired cannabinoid and/or cannabinoid acid using a suitable analytical technique, and those fractions containing the highest amounts of the desired cannabinoid and/or cannabinoid acid selected for further processing. Solvent can be then removed from the selected fractions, e.g., by evaporation, e.g., rotary evaporation or equivalents.

In alternative embodiments, the fractions enriched in a given cannabinoid obtained from the gradient elution normal phase chromatographic step are mixed with a solvent of the opposite polarity thereby causing a concentration of the cannabinoids in the second solvent phase. In alternative embodiments, the solvent is then removed.

In alternative embodiments, the fractions containing a product enriched in a given cannabinoid obtained from the gradient elution normal phase continuous chromatographic step or steps are re-dissolved in a gradient elution solution. In alternative embodiments, the fractions containing a product enriched in a given cannabinoid such as mixtures comprising CBD and THC, or mixtures of CBD and CBG or mixtures of CBG and CBC, are dissolved in a gradient elution solution and subjected to a continuous reverse phase chromatographic purification step to produce substantially pure extracts.

In alternative embodiments, the product of the reverse phase chromatographic step is collected in multiple fractions, which can then be tested for the presence of the desired cannabinoid and/or cannabinoid acid using any suitable analytical technique. Fractions enriched in the desired cannabinoid or cannabinoid acid can then be selected for further purification. In alternative embodiments, the gradient elution solution is removed from the selected fractions or optionally additional gradient solvent is added to change the polarity of the gradient solvent contained in the selected fraction.

An exemplary embodiment comprises: fractions enriched in a given cannabinoid obtained from the gradient elution reverse phase chromatographic step are mixed with a solvent of the opposite polarity thereby causing a concentration of the cannabinoids in the second solvent phase. In alternative embodiments, the solvent is then removed. In alternative embodiments, the selected fraction is then subjected to one or more additional reverse phase chromatographic steps and one or more gradient elution solutions modifications. In alternative embodiments, the reverse phase chromatographic step comprises a column chromatography continuous mode, and can be based on polarity or affinity.

In alternative embodiments, various different elution solutions can be used in combination with this type of matrix, for example dimethyl sulfoxide, pyridine water, dimethylformamide, methanol, saline chloroform, propanol, ethanol, isobutanol, formamide, butanol, isopropanol, tetrahydrofuran, dioxane, dichloromethane, dichloroethane, etc.

In alternative embodiments, the chromatographic step comprises continuous column chromatography using an ion exchange resin such as but not limited to RediSep® Rf SAX, Dowex® Marathon C Na, Marathon C H, Marathon MSC-1 or Dowex Marathon WBA™ column, and eluting can be with a 20:1; 15:1; 10:1, 5:1; 4.5:1; 4:1; 3.5:1; 3:1 2:1; 1.9:1; 1.8:1; 1.7:1; 1.6:1; 1.5:1; 1.4:1; 1.3:1; 1.2:1; 1.1:1; 1.01:1; 1.001:1; 0.1:1 mixture of elution solutions such as chloroform, dichloromethane, dichloroethane methanol, ethanol, propanol, dimethyl sulfoxide, water, dimethylformamide, methanol, ethylene dichloride, chloroform, propanol, ethanol, isobutanol, formamide, butanol, isopropanol, tetrahydrofuran, dioxane, chloroform dichloromethane, dichloroethane, acetic acid, carbonic acid, glycolic acid, benzoic, methanoic, formic acid, oxalic acid, sodium hydroxide, potassium hydroxide, ammonium hydroxide, ammonium carbonate, etc, and/or water. Any suitable combination of ion exchange phase column packing material and solvent having separation characteristics suitable for use in purification of cannabinoids and cannabinoids acid can be used with equivalent effect.

In alternative embodiments, the column gradient eluate is collected in several fractions. In alternative embodiments, the fractions are tested for the presence of the desired cannabinoid or cannabinoid acid using a suitable analytical technique, and those fractions containing the highest amounts of the desired cannabinoid or cannabinoid acid. In alternative embodiments, solvent is then removed from the selected fractions, optionally by evaporation, e.g., rotary evaporation.

In alternative embodiments, the fractions containing a product are enriched in a given cannabinoid acid obtained from the continuous gradient elution chromatographic step or steps, and the fractions containing a product enriched in a given cannabinoid acid obtained from gradient elution reverse phase step or steps are re-dissolved in a gradient elution solution. In alternative embodiments, the fractions containing a product enriched in a given cannabinoid acid such as tetrahydrocannabinolic acid (THCA), are dissolved in a gradient elution solution and subjected to a continuous ion exchange chromatographic purification step to produce substantially pure extracts. In alternative embodiments, the product of the ion exchange chromatographic step is collected in multiple fractions, which can then be tested for the presence of the desired cannabinoid or cannabinoid acid using any suitable analytical technique. Fractions enriched in the desired cannabinoid or cannabinoid acid can then be selected for further purification. In alternative embodiments, the gradient elution solution is removed from the selected fractions or optionally additional gradient solvent is added to change the polarity and/or hydrogen potential of the gradient solvent contained in the selected fraction. An exemplary embodiment comprises: the fractions enriched in a given cannabinoid obtained from the gradient elution ion exchange chromatographic step are mixed with a solvent of the opposite polarity thereby causing a concentration of the cannabinoids in the second solvent phase. The solvent can then be removed.

In alternative embodiments, the selected fraction is then subjected to one or more additional continuous ion exchange chromatographic steps and one or more gradient elution solutions modifications. The continuous ion exchange chromatographic step can comprise column chromatography in fixed or continuous mode, and can be based on molecular sizing and polarity ion exchange resin such as but not limited to RediSep® Rf SAX, Dowex® Marathon C Na, Marathon C H, Marathon MSC-1 or Dowex Marathon WBA™.

In alternative embodiments, various different elution solutions can be used in combination with this type of matrix, for example dimethyl sulfoxide, pyridine, water, dimethylformamide, methanol, saline, ethylene dichloride, chloroform, propanol, ethanol, isobutanol, formamide, methylene dichloride, butanol, isopropanol, tetrahydrofuran, dioxane, chloroform, acetic acid, carbonic acid, glycolic acid, benzoic acid, formic acid, oxalic acid, sodium hydroxide, potassium hydroxide, ammonium hydroxide, ammonium carbonate, etc.

In alternative embodiments, essential features of the process are the same for purification of all cannabinoids and cannabinoid acids. *Cannabis* plants generally contain complex mixtures of cannabinoid acids and cannabinoids, although depending on the variety of cannabis one type of cannabinoid may pre-dominate. The purpose of the gradient elution chromatographic steps (ii) is to continuously separate the various cannabinoid and/or cannabinoid/cannabinoid acid components of the crude plant extract loaded in step (i), as described above, into substantially pure fractions or substantially pure mixtures of fractions which are then optionally subjected to additional gradient elution chromatography comprising normal phase, reverse phase and/or ion exchange.

In alternative embodiments, the product of the chromatographic step is collected in multiple fractions, which can then be tested for the presence of the desired cannabinoid/cannabinoid acid using any suitable analytical technique.

Fractions enriched in the desired cannabinoid/cannabinoid acid can then be selected for further purification. Hence, the same simple process steps can be adapted for purification of essentially any plant-derived cannabinoid or cannabinoid acid.

Selectivity for different cannabinoids or cannabinoid acids can be enhanced by selection of appropriate starting plant material. By way of example, if it is desired to prepare substantially pure $\Delta^9$ THC or $\Delta^9$ THCA then "high THC" cannabis plants can be selected as the starting material. Alternatively, if it is desired to prepare substantially pure CBD or CBDA then "high CBD" cannabis plants can be selected as the starting material. It is to be understood that processes are provided herein are of general utility and are not limited to the use of particular *Cannabis* varieties as the starting material. The precise cannabinoid content of any particular *Cannabis* plant material can be qualitatively and quantitatively determined using analytical techniques well known to those skilled in the art, such as thin-layer chromatography or high-performance liquid chromatography (HPLC). Thus, one may screen a range of various *Cannabis* plants and select those having a high content of the desired cannabinoid acid or cannabinoid for use as starting material in a process as provided herein.

With the use of conventional selective breeding techniques it is possible to develop cannabis varieties (chemovars) having varying cannabinoid content. Select cannabis varieties (chemovars) have relatively high content of CBD, or of the minor cannabinoids $\Delta^9$-tetrahydrocannabivarin ($\Delta^9$-THCV), cannabigerol (CBG) or cannabichromene (CBC). General protocols for growing of medicinal cannabis and for testing the cannabinoid content of cannabis plants are described in International patent application WO 02/064109.

In alternative embodiments, methods further provide for the generation of a substantially pure preparation of $\Delta^9$ THC having a chromatographic purity of greater than about 75%, 80%, 90%, 95%, 96%, 97%, 98%, or 99% or more by area normalization of an HPLC profile. The preparation can be a semi-solid at room temperature. The preparation can comprises less than about 1.5%, less than about 0.4%, or less than about 0.2%; or, less than about 0.1% CBD (w/w), less than about 0.5%, less than about 0.4%, or less than about 0.2%, or less than about 0.1% CBD (w/w) as analyzed by HPLC.

In alternative embodiments, the pure $\Delta^9$-THC provided by exemplary methods as provided herein have utility as an active pharmaceutical agent, and is also useful as a chromatographic standard, particularly as a comparative standard in the qualitative analysis of botanical drug substances derived from cannabis. The availability of highly pure $\Delta^9$-THC will also facilitate studies of the pharmacology of $\Delta^9$-THC.

Exemplary method
i) obtaining an ethanolic solution of a botanical drug substance from cannabis or hemp plant material,
ii) passing the solution obtained in step i) through a filter, and collecting the eluate,
iii) optionally substantially remove solvent from the eluate, e.g., by evaporation, e.g., rotary evaporation to give a cannabinoid enriched fraction,
iv) optionally adding solvent to the eluate,
v) continuously loading a solution of the resulting cannabinoid enriched extract onto a column packed with a stationary phase resin such as DOWEX® MARA-THON C Na™, MARATHON C H™, and continuously conducting a gradient elution of 50:1; 20:1; 10:1; 9:1; 8:1; 7:1; 6:1; 5:1; 4:1; 3:1; 2:1; 1; 1; 0.5:1; 0.005:1; 0.0005:1 chloroform/methanol or ethanol,
vi) adjusting hydrogen potential of said gradient solvent solution,
vii) collecting $\Delta^9$-THC and CBD enriched fractions and optionally removing solvent, e.g., by evaporation, e.g., rotary evaporation,
viii) optionally re-dissolving the crude $\Delta^9$ THC and CBD prepared in step vii) and continuously loading the solution on a column packed with a normal phase reverse phase resin, and continuously conducting a gradient elution of 10:1; 9:1; 8:1; 7:1; 6:1; 5:1; 4:1; 3:1; 2:1; 1; 1 methanol/water,
xiii) optionally re-dissolving the crude $\Delta^9$ THC and CBD prepared in step vii) such as DOWEX® MARATHON C Na™, MARATHON C H™, and conducting a gradient elution of 50:1; 20:1; 10:1; 9:1; 8:1; 7:1; 6:1; 5:1; 4:1; 3:1; 2:1; 1; 1; 0.5:1; 0.005: 1; 0.0005:1 chloroform and polar solvent mixture.
vi) adjusting hydrogen potential of said gradient solvent solution
vii) collecting the $\Delta^9$ THC enriched fractions and removing solvent, e.g., by evaporation, e.g., rotary evaporation to give a semi-solid preparation of $\Delta^9$ THC.
(viii) collecting the CBD enriched fractions and removing solvent, e.g., by evaporation, e.g., rotary evaporation to give a semi-solid preparation of CBD.

Example 11: Exemplary Methods

In alternative embodiments, the "extract containing a cannabinoid or a cannabinoid acid" is dissolved in a gradient elution solution and subjected to a chromatographic purification step to produce substantially pure cannabinoids and a product enriched in a given cannabinoid. The purpose of this step is to first remove the targeted non-cannabinoid material comprising for example terpenes, carotenes,
and flavonoids and also to provide a degree of separation/fractionation of the various cannabinoid/cannabinoid acid components of the extract.

In alternative embodiments, the product of the chromatographic step is collected in multiple fractions, which can then be tested for the presence of the desired cannabinoid/cannabinoid acid using any suitable analytical technique.

Fractions enriched in the desired cannabinoid and/or cannabinoid acid can then be selected for further purification. Optionally the gradient elution solution is removed from the selected fractions or optionally additional gradient solvent is added to change the polarity or hydrogen potential of the gradient solvent contained in the selected fraction. The selected fraction can then be subjected to one or more additional chromatographic steps and one or more gradient elution solutions modifications.

In alternative embodiments, the chromatographic step comprises a column chromatography in a fixed or a continuous mode, and is can be based on molecular sizing, polarity and/or hydrogen potentiality. In alternative embodiments, the column matrix materials are, for example; silica (or silica gel) and alumina normal phase and reverse phase such as for example C18, C8, C4, C2, Amino, Cyano, Phenyl, Diol, WAX, SAX, WCX, SCX, thiol; acidic, basic and neutral, styrenic, divinylbenzene, polystyrene/divinylbenzene, brominated styrenic; ion exchange resins such as strongly acidic, typically featuring sulfonic acid groups, e.g. sodium polystyrene sulfonate or polyAMPS; strongly basic, typically featuring quaternary amino groups, for example, trimethylammonium groups, e.g. polyAPTAC); weakly acidic, typically featuring carboxylic acid groups; weakly basic, typically featuring primary, secondary, and/or tertiary amino groups, e.g. polyethylene amine.

In alternative embodiments, various different elution solutions can be used in combination with this type of matrix, for example dimethyl sulfoxide, pyridine, water, dimethylformamide, methanol, saline, ethylene dichloride, chloroform, propanol, ethanol, isobutanol, formamide, methylene dichloride, butanol, isopropanol, tetrahydrofuran, dioxane, hexane, butane, pentane, heptane, octane, terpene, hemiterpene, monoterpene, diterpene, limonene, humulene, pinene, myrcene, caryophylene, carbon tetrachloride, and equivalents, or any combination thereof.

In alternative embodiments, the chromatographic step comprises column chromatography on for example, a silica (or silica gel) or an alumina column, and the step can comprise eluting with a 5:1; 4:1; 3:1; 2:1; 1.9:1; 1.8:1; 1.7:1; 1.6:1; 1.5:1; 1.4:1; 1.3:1; 1.2:1; 1.1:1; 1.01:1; 1:1; 0.9:1; 0.5:1; 0.1:1 mixture of elution solutions such as chloroform, methylene dichloride, ethylene dichloride, methanol, ethanol, propanol and/or water. Any suitable combination of normal phase column packing material and solvent having separation characteristics suitable for use in separation (fractionation) of cannabinoids and/or cannabinoid acids can be used with equivalent effect.

In alternative embodiments, the column gradient eluate is collected in several fractions. The fractions are tested for the presence of the desired cannabinoid and/or cannabinoid acid using a suitable analytical technique, and those fractions containing the highest amounts of the desired cannabinoid and/or cannabinoid acid selected for further processing. Solvent can be then removed from the selected fractions, e.g., by rotary evaporation or equivalents.

In alternative embodiments, the fractions enriched in a given cannabinoid obtained from the gradient elution normal phase chromatographic step are mixed with a solvent of the opposite polarity thereby causing a concentration of the cannabinoids in the second solvent phase. In alternative embodiments, the solvent is then removed.

In alternative embodiments, the fractions containing a product enriched in a given cannabinoid obtained from the gradient elution normal phase chromatographic step or steps are re-dissolved in a gradient elution solution. In alternative embodiments, the fractions containing a product enriched in a given cannabinoid such as mixtures comprising CBD and THC, or mixtures of CBD and CBG or mixtures of CBG and CBC, are dissolved in a gradient elution solution and subjected to a reverse phase chromatographic purification step to produce substantially pure extracts.

In alternative embodiments, the product of the reverse phase chromatographic step is collected in multiple fractions, which can then be tested for the presence of the desired cannabinoid and/or cannabinoid acid using any suitable analytical technique. Fractions enriched in the desired cannabinoid or cannabinoid acid can then be selected for further purification. In alternative embodiments, the elution solution is removed from the selected fractions or optionally additional solvent is added to change the polarity of the solution contained in the selected fraction.

An exemplary embodiment comprises: fractions enriched in a given cannabinoid obtained from the elution of a reverse phase chromatographic step are mixed with a solvent of the opposite polarity thereby causing a concentration of the cannabinoids in the second solvent phase. In alternative embodiments, the solvent is then removed. In alternative embodiments, the selected fraction is then subjected to one or more additional reverse phase chromatographic steps and one or more elution solutions modifications. In alternative embodiments, the reverse phase chromatographic step comprises a column chromatography in fixed or continuous mode, and can be based on polarity. Examples of reverse phase column chromatography include but are not limited to pure silica, alkyl chain-bonded silica, cyano-bonded silica, and phenyl-bonded silica, C18, C8, C4, C2, amino, cyano, phenyl, diol, WAX, SAX, WCX, SCX, thiol; acidic, basic and neutral, styrenic, divinylbenzene, polystyrene/divinylbenzene, brominated styrenic and equivalents and combinations thereof.

In alternative embodiments, various different elution solutions can be used in combination with this type of matrix, for example dimethyl sulfoxide, pyridine, water, dimethylformamide, methanol, saline, chloroform, propanol, ethanol, isobutanol, formamide, butanol, isopropanol, tetrahydrofuran, dioxane, chloroform, dichloromethane, dichloroethane, etc.

In alternative embodiments, the chromatographic step comprises column chromatography using an ion exchange resin such as but not limited to RediSep® Rf SAX, Dowex® Marathon C Na, Marathon C H, Marathon MSC-1 or Dowex Marathon WBA™ column, and eluting can be with a 20:1; 15:1; 10:1, 5:1; 4.5:1; 4:1; 3.5:1; 3:1 2:1; 1.9:1; 1.8:1; 1.7:1; 1.6:1; 1.5:1; 1.4:1; 1.3:1; 1.2:1; 1.1:1; 1.01:1; 1.001:1; 0.1:1 mixture of elution solutions such as chloroform, dichloromethane, dichloroethane methanol, ethanol, propanol, dimethyl sulfoxide, water, dimethylformamide, methanol, ethylene dichloride, chloroform, propanol, ethanol, isobutanol, formamide, methylene dichloride, butanol, isopropanol, tetrahydrofuran, dioxane, dichloromethane, dichloroethane, acetic acid, carbonic acid, glycolic acid, benzoic, methanoic, formic acid, oxalic acid, sodium hydroxide, potassium hydroxide, ammonium hydroxide, ammonium carbonate, etc, and/or water. Any suitable combination of ion exchange phase column packing material and solvent having separation characteristics suitable for use in purification of cannabinoids and cannabinoids acid can be used with equivalent effect.

In alternative embodiments, the column eluate is collected in several fractions.

In alternative embodiments, the fractions are tested for the presence of the desired cannabinoid or cannabinoid acid using a suitable analytical technique, and those fractions containing the highest amounts of the desired cannabinoid or cannabinoid acid. In alternative embodiments, solvent is then removed from the selected fractions, optionally by rotary evaporation.

In alternative embodiments, the fractions containing a product are enriched in a given cannabinoid acid obtained from the elution chromatographic step or steps, and the fractions containing a product enriched in a given cannabinoid acid obtained from elution reverse phase step or steps are re-dissolved in an elution solution. In alternative embodiments, the fractions containing a product enriched in a given cannabinoid acid such as tetrahydrocannabinolic acid (THCA), are dissolved in an elution solution and subjected to an ion exchange chromatographic purification step to produce substantially pure extracts. In alternative embodiments, the product of the ion exchange chromatographic step is collected in multiple fractions, which can then be tested for the presence of the desired cannabinoid or cannabinoid acid using any suitable analytical technique. Fractions enriched in the desired cannabinoid or cannabinoid acid can then be selected for further purification. In alternative embodiments, the elution solution is removed from the selected fractions or optionally additional solution is added to change the polarity and/or hydrogen potential of the solution contained in the selected fraction. An exemplary embodiment comprises: the fractions enriched in a given cannabinoid obtained from the elution ion exchange chromatographic step are mixed with a solvent of the opposite polarity thereby causing a concentration of the cannabinoids in the second solvent phase. The solvent can then be removed.

In alternative embodiments, the selected fraction is then subjected to one or more additional ion exchange chromatographic steps and one or more isocratic or gradient elution solutions modifications. The ion exchange chromatographic step can comprise column chromatography in fixed or continuous mode, and can be based on molecular sizing and polarity ion exchange resin such as but not limited to RediSep® Rf SAX, Dowex® Marathon C Na, Marathon C H, Marathon MSC-1 or Dowex Marathon WBA™ In alternative embodiments, various different elution solutions can be used in combination with this type of matrix, for example dimethyl sulfoxide, water, dimethylformamide, methanol, ethylene dichloride, chloroform, propanol, ethanol, isobutanol, formamide, methylene dichloride, butanol, isopropanol, tetrahydrofuran, dioxane, acetic acid, carbonic acid, glycolic acid, benzoic acid, formic acid, oxalic acid, sodium hydroxide, potassium hydroxide, ammonium hydroxide, ammonium carbonate, etc.

In alternative embodiments, essential features of the process are the same for purification of all cannabinoids and cannabinoid acids. *Cannabis* plants generally contain complex mixtures of cannabinoid acids and cannabinoids, although depending on the variety of cannabis one type of cannabinoid may pre-dominate. The purpose of the elution (e.g., gradient elution) chromatographic steps (ii) is to separate the various cannabinoid and/or cannabinoid/cannabinoid acid components of the crude plant extract loaded in step (i), as described above, into substantially pure fractions or substantially pure mixtures of fractions which are then optionally subjected to isomerization reactions and/or elimination reactions and/or additional gradient elution chromatography comprising normal phase, reverse phase and/or ion exchange.

In alternative embodiments, the product of the chromatographic step is collected in multiple fractions, which can then be tested for the presence of the desired cannabinoid/cannabinoid acid using any suitable analytical technique.

Fractions enriched in the desired cannabinoid/cannabinoid acid can then be selected for further purification. Hence, the same simple process steps can be adapted for purification of essentially any plant-derived cannabinoid or cannabinoid acid.

Selectivity for different cannabinoids or cannabinoid acids may be enhanced by selection of appropriate starting plant material. By way of example, if it is desired to prepare substantially pure $\Delta^9$ THC or $\Delta^9$ THCA then "high THC" cannabis plants can be selected as the starting material. Alternatively, if it is desired to prepare substantially pure CBD or CBDA then "high CBD" cannabis plants can be selected as the starting material. It is to be understood that processes as provided herein are of general utility and are not limited to the use of particular *Cannabis* varieties as the starting material. The precise cannabinoid content of any particular *Cannabis* plant material can be qualitatively and quantitatively determined using analytical techniques well known to those skilled in the art, such as thin-layer chromatography or high-performance liquid chromatography (HPLC). Thus, one may screen a range of various *Cannabis* plants and select those having a high content of the desired cannabinoid acid or cannabinoid for use as starting material in a process as provided herein.

With the use of conventional selective breeding techniques it is possible to develop cannabis varieties (chemovars) having varying cannabinoid content. Select cannabis varieties (chemovars) have relatively high content of CBD, or of the minor cannabinoids $\Delta^9$-tetrahydrocannabivarin ($\Delta^9$-THCV), cannabigerol (CBG) or cannabichromene (CBC). General protocols for growing of medicinal cannabis and for testing the cannabinoid content of cannabis plants are described in International patent application WO 02/064109.

In alternative embodiments, methods further provide for the generation of a substantially pure preparation of $\Delta^9$ THC having a chromatographic purity of greater than about 75%, 80%, 90%, 95%, 96%, 97%, 98%, or 99% or more by area normalization of an HPLC profile. The preparation can be a semi-solid at room temperature. The preparation can comprises less than about 1.5%, less than about 0.4%, or less than about 0.2%; or, less than about 0.1% CBD (w/w), less than about 0.5%, less than about 0.4%, or less than about 0.2%, or less than about 0.1% CBD (w/w) as analyzed by HPLC.

In alternative embodiments, the pure $\Delta^8$-THC and $\Delta^9$-THC provided by exemplary methods as provided herein have utility as an active pharmaceutical agent, and is also useful as a chromatographic standard, particularly as a comparative standard in the qualitative analysis of botanical drug substances derived from cannabis. The availability of highly pure $\Delta^8$-THC and $\Delta^9$-THC will also facilitate studies of the pharmacology of $\Delta^8$-THC and $\Delta^9$-THC mixtures.

In alternative embodiments, an exemplary method for preparation of substantially pure $\Delta^8$-THC and $\Delta^9$ THC comprises:

i) obtaining an ethanol, hexane or terpene extraction solution of a botanical drug substance from cannabis or hemp plant material, ii) passing the solution obtained in step i) through a filter, and collecting the eluate, iii) optionally substantially remove solvent from the eluate by rotary evaporation to give a cannabinoid enriched fraction, iv) optionally adding solvent to the eluate, v) passing a solution of the resulting cannabinoid enriched extract through a column packed with a stationary phase resin such as DOWEX® MARATHON C Na™, MARATHON C H™, and conducting a gradient elution of 50:1; 20:1; 10:1; 9:1; 8:1; 7:1; 6 5:1; 5:1; 4:1; 3:1; 2:1; 1; 1; 0.5:1; 0.005:1; 0.0005:1 chloroform/methanol or ethanol, vi) adjusting hydrogen potential of said solution, vii) collecting $\Delta^9$-THC and CBD enriched fractions and optionally removing solvent by rotary evaporation, viii) mixing the collected $\Delta^9$ THC and CBD with a reaction solvent and a catalyst for a period of time and adding a neutralizing agent and removing catalyst and neutralizing agent by filtration to generate a reduced CBD and enriched $\Delta^8$-THC and $\Delta^9$-THC mixture, optionally removing reaction solvent, ix) mixing reduced CBD and enriched $\Delta^8$-THC and $\Delta^9$-THC mixture with optionally additional reaction solvent and a stabilizing agent, mixing stabilizing agent for a period of time x) optionally removing the reaction solvent, x) optionally re-dissolving the enriched $\Delta^8$ THC, $\Delta^9$ THC and reduced CBD prepared in steps viii) through x) and passing the solution through a column packed with reverse phase resin, and conducting a gradient elution of 10:1; 9:1; 8:1; 7:1; 6:1; 5:1; 4:1; 3:1; 2:1; 1; 1 methanol/water, xiii) optionally re-dissolving the crude $\Delta^8$ THC, $\Delta^9$ THC and reduced CBD prepared in steps viii) through x) and passing the solution through a column packed with an ion exchange resin such as DOWEX® MARATHON C Na™, MARATHON C H™, and conducting an elution of 50:1; 20:1; 10:1; 9:1; 8:1; 7:1; 6:1; 5:1; 4:1; 3:1; 2:1; 1; 1; 0.5:1; 0.005: 1; 0.0005:1 chloroform and polar solvent mixture.

xiv) adjusting hydrogen potential of said solution xv) collecting the THC enriched fractions and removing solvent by rotary evaporation to give a semi-solid preparation of THC.

Example 12: Conversion of CBD to $\Delta^8$-THC and $\Delta^9$-THC

This Example describes an exemplary method for the conversion of CBD to $\Delta^8$-THC and $\Delta^9$-THC.

CBD (1 g) was added to 6.4 ml of reaction solvent and 1% p-toluenesulfonic acid. In this example, the mixture was reacted for 48 hours, although other time periods can also be used, as discussed below. It was then diluted with ether (20 ml) and poured into water, The upper layer was separated, washed with aqueous 5% $NaHCO_3$, then with water, dried over $MgSO_4$ and evaporated. GC-MS analysis on the crude product, showed the presence of 1.1% CBD; 18.4% $\Delta^8$-THC and 80.0% $\Delta^9$-THC. The crude product was then subjected to column chromatography. In the example described above, normal phase HPLC separation is used wherein the column is for example a silica gel and the mobile phase is an organic solvent mixture introduced as a gradient described in the invention. In other embodiments, reverse phase HPLC separation is used.

The p-toluenesulfonic acid is used as a catalyst in the above example. It is of note that boron trifluoride could also be used as a catalyst, as could a number of other Lewis acids or non-oxidizing acid catalysts. The exact proportion is not essential to the reaction proceeding. Other solvents can also be used, for example, benzene, toluene, chloroform, dichloromethane, etc.

In other embodiments, anhydrous $MgSO_4$ or another suitable agents such as $Na_2SO_4$, $CaSO_4$, and $CaCl_2$), known in the art is used in place of the $MgSO_4$.

Example 13: Conversion of CBD to $\Delta^8$-THC and $\Delta^9$-THC

This Example describes an exemplary method for the conversion of CBD to $\Delta^8$-THC and $\Delta^9$-THC.

A hemp extract was obtained by extraction of hemp in ethanol. The hemp extract was composed of CBD, THC, cannabinoids and other components and subjected to conversion of CBD to THC without further purification. The hemp extract and 1-5 mol % p-toluenesulfonic acid were sequentially added to 6.4 mL reaction solvent. In this example, the reaction mixture was stirred at room temperature for 24 hours, although other time intervals, the reaction mixture was diluted with ether (20 mL) and poured into water. The upper layer was separated, washed with aqueous 5% $NaHCO_3$, dried over $MgSO_4$ and concentrated on a rotary evaporator. GC-MS analysis on the crude product showed the conversion of CBD to $\Delta^8$-THC and $\Delta^8$-THC, for example, 0% CBD; 98% $\Delta^9$-THC; 2% $\Delta^8$-THC after 24 hours in the presence of 3 mol % p-toluenesulfonic acid. The crude product was then subjected to column chromatography. In the example described above, normal phase HPLC separation is used wherein the column is for example a silica gel and the mobile phase is an organic solvent mixture introduced as a gradient described in the invention. In other embodiments, reverse phase HPLC separation is used.

The p-toluenesulfonic acid is used as a catalyst in the above example. Boron trifluoride could also be used as a catalyst, as could a number of other Lewis acids or non-oxidizing acids known in the art. Other solvents can also be used, for example, benzene, toluene, chloroform, dichloromethane, etc.

In other embodiments, anhydrous $MgSO_4$ or another suitable agents such as $Na_2SO_4$, $CaSO_4$, and $CaCl_2$), known in the art is used in place of the $MgSO_4$.

A number of embodiments of the invention have been described.

Nevertheless, it can be understood that various modifications may be made without departing from the spirit and scope of the invention. Accordingly, other embodiments are within the scope of the following claims.

What is claimed is:

1. A method or process for obtaining or purifying a composition comprising a substantially pure $\Delta^8$-THC and a substantially pure $\Delta^9$-THC from a natural or a synthetic source, wherein the natural or the synthetic source comprises $\Delta^8$-THC and $\Delta^9$-THC, the method comprising:

(a) obtaining or being provided a first extract, aliquot or sample of the natural or synthetic source, wherein the first extract, aliquot or sample comprises a cannabidiol (CBD) from the natural or the synthetic source;

(b) dissolving the first extract, aliquot or sample in a first reaction solvent;

(c) adding a catalyst to the first extract, aliquot or sample and the first reaction solvent to generate a first reaction mixture, wherein the catalyst includes p-toluenesulfonic acid and the catalyst is free of boron trifluoride and free of boron trifluoride diethyl etherate;

(d) reacting the first extract, aliquot or sample, with the catalyst and the first reaction solvent, under reaction conditions at a temperature of about 5° C. for between about 1 to 30 hours;

(e) adding a neutralizing agent to the first reaction mixture;

(f) removing or substantially removing most or all of the catalyst and the neutralizing agent from the first reaction mixture to generate a first reaction product;

(g) dissolving the first reaction product in a second solvent;

(h) loading the dissolved first reaction product onto a first chromatography column, wherein the $\Delta^8$-THC and $\Delta^9$-THC are reversibly bound to the first chromatography column; and (i) eluting the dissolved first reaction product from the first column with an or at least one elution solution, thereby obtaining or purifying the composition comprising the substantially pure $\Delta^9$-THC and the substantially pure $\Delta^8$-THC.

2. The method or process of claim 1, further comprising dissolving ormixing in or adding the composition in a solvent to make a mixture of solvent and $\Delta^9$ THC and $\Delta^8$ THC, and loading the mixture onto a second chromatography column, and eluting the dissolved composition from the second column with an elution solution, thereby obtaining or purifying a substantially pure $\Delta^9$ THC and $\Delta^8$ THC.

3. The method or process of claim 2, wherein the second chromatography column is the same column or the same type of column as the first chromatography column.

4. The method or process of claim 1, wherein the natural source comprises a plant, algal, yeast, lichen or a microbial material, or a material derived from a plant source or plant, algal, yeast, lichen or microbial material.

5. The method or process of claim 1, wherein the catalyst is added before, simultaneous with, or after addition of the first reaction solvent to the first extract, aliquot, or sample.

6. The method or process of claim 1, wherein the reaction conditions comprise about 4 to 24 hours.

7. The method or process of claim 1, wherein the reaction conditions comprise about 6 to 15 hours.

8. The method or process of claim 1, wherein the reacting converts the CBD to a mixture comprising (unreacted) CBD, $\Delta^8$-THC, and $\Delta^9$-THC.

9. The method or process of claim 1, further comprising removing all or substantially most of the first reaction solvent, thereby leaving a first reaction product comprising (unreacted) CBD, $\Delta^8$-THC, and $\Delta^9$-THC.

10. The method or process of claim 1, wherein the second solvent is the same as the first reaction solvent.

11. The method or process of claim 1, wherein the first chromatography column is a normal phase chromatography column or a reverse phase chromatography column.

12. The method or process of claim 1, wherein the eluting comprises use of a gradient elution process and the substantially pure $\Delta^9$-THC and the substantially pure $\Delta^8$-THC are separately collected in different or separate gradient elution fractions.

13. The method or process of claim 1, wherein the eluting comprises use of an isocratic simulated moving bed (SMB) elution process and the substantially pure $\Delta^9$-THC and the substantially pure $\Delta^8$-THC are separately collected in different or separate elution fractions.

14. The method or process of claim 1, wherein the natural or the synthetic source further comprises at least one terpene.

15. The method or process of claim 14, wherein the CBD is reversibly bound to the first chromatography column in (h).

16. The method or process of claim 15, wherein the CBD is eluted before the $\Delta^8$-THC and $\Delta^9$-THC.

17. The method or process of claim 1, further comprising removing the first reaction solvent after (f) and before (g).

* * * * *